(12) United States Patent
Kaniadakis

(10) Patent No.: US 8,666,772 B2
(45) Date of Patent: Mar. 4, 2014

(54) PROCESS, SYSTEM, METHOD CREATING MEDICAL BILLING CODE LETTERS, ELECTRONIC SUPERBILL AND COMMUNICATION

(76) Inventor: Steven J. Kaniadakis, St. Petersburg, FL (US)

(*) Notice: Subject to any disclaimer, the term of this patent is extended or adjusted under 35 U.S.C. 154(b) by 53 days.

(21) Appl. No.: 13/180,265

(22) Filed: Jul. 11, 2011

(65) Prior Publication Data
US 2012/0010900 A1    Jan. 12, 2012

Related U.S. Application Data

(60) Provisional application No. 61/363,622, filed on Jul. 12, 2010.

(51) Int. Cl.
*G06F 15/16* (2006.01)
*G06Q 30/00* (2012.01)

(52) U.S. Cl.
USPC ............... 705/2; 382/182; 709/206

(58) Field of Classification Search
USPC ........................................... 705/2
See application file for complete search history.

(56) References Cited

U.S. PATENT DOCUMENTS

2004/0122704 A1*   6/2004   Sabol et al. .............. 705/2

* cited by examiner

*Primary Examiner* — Hiep V Nguyen

(57) ABSTRACT

This invention is a method creating a machine readable language of medical billing codes from medical records by artificial intelligence and human intelligence both. The software related engine is achieved by converting difficult billing code numbers into and from easy code letters. Also, this software makes scheduling easier, with reappointments and sends letters by electronic means, messaging, voice over internet protocol and wireless connections using an unique implementation of other applications in combination with this novel medical software operation.

18 Claims, 55 Drawing Sheets

PROCESS, SYSTEM, METHOD CREATING MEDICAL BILLING CODE LETTERS, ELECTRONIC SUPERBILL AND COMMUNICATION

CROSS-REFERENCE TO RELATED APPLICATIONS

This non-provisional utility U.S. Patent Office application claims benefits of U.S. Patent Office Provisional application No. 61/363,622, filed date on Jul. 12, 2010, for the above named titled, the priority of which is claimed, the entire contents of which are hereby incorporated by reference thereof.

BACKGROUND OF THE INVENTION

This invention relates, generally, to implementation of a type of medical computer and machine related method program.

The methodology facilitates a flow of the information to maintain absolute communication in two main ways:
1) Communication between clinical staff and business staff, including their patients. 2) Communication between providers of healthcare.

The following is a tabulation of some prior art that presently appears relevant;

U.S. Pat. Nos. 3,566,365, 4,591,974 simply show renditions from hand held "superbill" implements. Sixteen other patents mention "superbill" implements without present invention's novelty, including U.S. Pat. No. 5,519,607. Clearly patentability is further evidenced in plurality of prior art. U.S. Pat. No. 5,915,241 prior art limitations include a design with reference to relative value units RVU, an actuarial operation opposed to an objective design as in present art to rule out fee outcomes, further this prior art is essentially a design for alternative (medical) practices, opposed to an standardized, acceptable AMA CPT codes. AMA CPT is essentially irrelevant to "alternative" practices and cannot precisely equate in terms of service code and coding or billing code practice. U.S. Pat. No. 5,809,476 emphasis is in reference to a British system, and primarily on ICD, diagnosis coding, "generalized" terms which can be misread or equated to universal standard information and without corresponding an ICD with CPT procedure. Present art is equating to acceptable standardized terms and descriptions. Aforesaid prior art limitations are foreclosed by "correcting" or "supplementing" the "original information". Present invention equates to acceptable terms of AMA CPT or relative to coded data base stored to make uniform billing code practices. U.S. Pat. No. 5,325,293 limitations include change code in terms of "RUV", reimbursement and actuarial billing codes. The said art uses "raw" or standard "correlating CPT codes", appears unlike U.S. Pat. Nos. 5,915,241 and 5,809,476. This said art emphasis is on CPT, and foreclosed limitation on ICD codes. Any listed ICD are not an emphasis on the particular sequence or order of priority. As stated, the first ICD diagnosis is given priority in billing code process and it can delay or cause inaccurate billing codes processed. U.S. Pat. Nos. 6,192,345; 7,676,386; 7,650,291; 7,739,123; 7,613,610; 7,610,192; 7,520,419; 7,233,938; 7,410,955; 6,915,254; 6,850,889; 6,820,093; 6,192,345; 5,483,443; Prior art in latter cases mainly on "extraction", actuarial, and evidence of other limitations stated.

Comprehensive computer implementations or other related applications may show the handling of electronic H.C.F.A submissions. Others may show a way to hide, encode, encrypt or "privacy" design, security and other features. Whereas, this invention's art is providing a means for compatibility providing such other computers, devices and machine implementation thereof. As described herein this invention is to become essentially a tool or instrument, and it serves a function combined with external implementation related packages. Wherein other implementations might very well have implements designed for security, electronic components to process heath care records and "privacy" and things. This invention may rely upon others when serving roles external programs offer, this invention becomes compatible to those programs, and it becomes obviated not to need such other purported superior designs in this invention's application. The idea of Skype®, for instance, as becoming part of this implementation of this present invention was discussed herein. The idea of Skype to implement what might be their purported technology to use their application out of their native implementation method application as a part of another's application method or implementation related program (native or web based), by highlighted phone numbers and their "Click To Call" is a belief of inventor, and his present invention, to have been an implementation Skype had made ex post facto to present invention's art. Wherein, an application, as Skype's, may become utilized on other sites, e-mail and applications like web sites, to have highlighted telephonic numbers Skype subsequently promoted as a feature of their application. Skype® started showing up on Yahoo! ® web sites and other e-mail applications. After this present invention's various documentation and development continued. Most recent history shows Facebook® as joined to add Skype in a manner purported by this inventive technology reported herein and documentation supporting present invention's as believed to have been first to have a click (or touch) and say phone number to call the (patient) from the appointment book implementation described as a part of present invention's art. Although Skype owns a certain application about their "call" and their "instant message" operation or system, the description as a specifications being part of this invention had been believed to have been already documented, including U.S. Copyrights Office. Again, other voice-over-internet-provider and e-mail systems or providers can be part of this inventive appointment book's design. As stated in present inventions aforesaid referenced "Provisional" submitted work. Since, "claims", according to inventor's reading of U.S. Patent instructions, generally are not to be actually stated as such in "Provisional" submitted material. Disclaimer(s), by contrast, have been submitted in invention's Provisional as to that technology. When such technology is not a part of such implements becoming used out of another known electronic or software, implementation and machine method related application. It is claimed in this inventions art, described in present inventor's "Provisional" application, and it was stated in a disclaimer with this specific reference as to what is now claimed versus what was disclaimed and in what way(s). Whereas, this was and it is now articulated in these documentations and others related to present invention art.

Prior art show a plurality of "extraction" methods, systems, schemes and processes using only artificial intelligence, machine readable to review medical records to generate billing codes. This has become essentially the latest ways to present superior art to virtually solve some of the related problems this present invention has solved in actually easier ways. A problem is that machine or artificial intelligence cannot be superior to human intelligence in this billing practice. These variables will be shown distinguishing prior art from this present invention in many superior ways.

Prior art demonstrates other limitations. The information of Current Procedural Terminology (C.P.T billing codes), International Classification of Disease (I.C.D, diagnosis codes) and/or H.C.P.C.S (supply) codes is part-and-parcel set of information to the typical billing process. It is more than data information, since it requires human diagnosis. This data cannot be separated concerning the patient's billing code system. Accurate CPT is needed along there with accurate ICD, and accurate matching thereby is significant. Likewise, the human element of medical diagnosis cannot be negated. The physician and particular patient's treatment, that is, service render therewith the particular primary diagnosis used to delivery said accuracy for the true form of billing records. The machine and the other billers and coders are without first-hand knowledge.

Prior art negates either I.C.D in "extraction" or the "extraction" of C.P.T medical records needed to effectuate this accuracy of this match. The proper primary diagnosis cannot be a factor determined by machine, coders and billers. Since, it is actually human intelligence that provides the needed statements as with reference to primary, secondary, tertiary, quandary diagnosis list, the sequential order, ranking operation, or the hierarchy in this data set specification. When information becomes extracted, the sequential order is not produced once leaving the treating provider's hands. A diagnosis may become inadvertently given a secondary when it should be a primary diagnosis, if stated, intentionally changed automatically by designed machines or other coders and billers.

Therefore, prior art limitations result when all these components are not taken into account, left out of the logic or equation, including the critical element of the human intelligence and human knowledge base. Prior art's data bases cannot reproduce this retroactively or otherwise be predictive of this "face-to-face" human input part of the billing code process.

Present art is designed to be non-transitory machine readable and human intelligence is required. These components are all in present invention's art, CPT, ICD, HCPCS and other billing codes needed to be precisely matched. Also, the present invention has a method to produce an artificial intelligence with a machine and human stored readable database. Present invention enables users to create code letters which are utilized to equate with code numbers, which in turn equate with code descriptions, which further becomes set in computer readable storage and enabling the this data to be extracted from in medical records in this process. Extraction machines can readily be used to read code letters entered by physician's artificial intelligence data base and (his or her) human knowledge base. Although, the novelty hereof this invention's super biller is essentially the instrument as s method in this process, and extraction may be still become used by other implementations in prior art. To make prior art's limitations whole, where identified as discussed in the following prior art references reviewed. Virtual diagnosis code selections are replaced by actual selections in the present invention's art. Likewise, virtual service codes become validated by actual provider's account of events in treatment, after review of machine or other billers and coders change records and medium. It is more than pushing a button or a click. However, some things are just inescapable in the arena of health care quality assurance.

Prior art is essentially actuarial in context. Prior art is essentially geared as a means for producing an outcome which may favor either the most or least reimbursement depending on the known type user. Opposed to a method of the current art having accuracy with reference to the actual account of input from treating providers with reference to medical knowledge and the proper first-hand knowledge including the actual goods and service rendered and each the actual listed corresponding sequence thereof primary, secondary, tertiary, quaternary diagnosis(es). Present art thereby further enabling a method, for the user uncertain about reimbursement billing codes, to use their own customizable in-house code letters and not primarily based upon computing maximizing or minimizing reimbursement. In the alternative, present art's superior design benefits those ordinarily skilled in the art in light of changing codes causing confusion and delayed healthcare benefits.

Prior art limitations also noted are deviations from standardized and acceptable practices by American Medical Association, the body that created C.P.T, and what A.M.A calls certain "cleaned up" versions of I.C.D and HCPCS to correspond thereto. Again, history will show that prior art compromised essentially by the use of actuary algorithms, billing codes logic that work for the pool of patients. Opposed to the present invention that uses each particular patient's actual treatment and/or services rendered and face-to-face encounters in a relatively real time operation.

The present art takes values of face-to-face encounters rather than prior art that essentially uses actuarial billing code generation in terms on monetary interests alone.

The present inventions can be distinguished from prior art by allowing provider select customized in-house customizable code letters that they create, with human and computer stored readable databases. This design helps providers avoid pre-selection criteria in prior art limitations and the selection of or generation of incorrect billing code accounts. Code letters that can become dictated into medical records and extracted by means that may become part of the improvement prior art, to make prior art superior.

The ultimate superior art would take into account the following; the significance of the actual face-to-face patient encounter information of each diagnosis (ICD) to be listed in a sequential order by the significance of priority ranking and the actuary importance, typically an ascending order, with ICD listed as primary, secondary, tertiary, quandary; such ICD to become matched to each and every particular CPT service on a superior instrument or superior Superbill; include a means for extracting medical related data by human and by machine both, CPT and ICD both; include typically up to four (4) fields for ICD given in standard practices by convention as prescribed by the Health Care Finance Administration (H.C.F.A) standardized implementation forms and process by design, a body known to have the acceptable instrument used to properly submit billing codes; computer storable data base of ICD and CPT history; means to account for medical and actuarial significance to review the billing codes created before and after submissions, to change ICD and/or CPT; a means to account for actual and virtual service and/or supply codes (CPT and HCPCS codes), by systematic mechanical intelligence along therewith by human knowledge and intelligence both; means to utilize primarily reproducible, uniform, with acceptable the A.M.A's C.P.T billing codes and coding practices; means to provide objective and subjective billing and coding practices for each particular patient encounter on a given date of service, reflecting the actual care rendered in the date of service proximal to the actual date, in retrospective reviews by any given subsequent billers and coders; method to help take relatively un-skilled providers and those users that find themselves having less than ordinary skill in the art out from the loop by a system or operation that allows a subjective place holder code, a transitional code, until the relatively skilled people, and their computers, may produce accurate billing codes and their opinions from retroactive reviews of physician's orders and medical records and/or implementations; by contrast, means to help skilled providers, billers, coders, a neutral code, a subjective, generic code, and transitional code which could be implemented until specific accurate codes are presented, until updates that need to arrive or until staff needs to become updated by the learning curve of new changes in billing code material (errors and omissions avoided by selection of outdated billing codes); by contrast to above also means to help maintain treating providers in-the-loop (computer and human loop created billing code scheme) by allowing a subjective place holder code (code letters) until machines and staff become updated; a neutral code that can become the Olympian acceptable and convertible to acceptable standardized coding and billing practices in the international arena (European's and American Medical Association codes).

Medical and surgical procedures are billed using uniform practices and codes to assure that similar procedures are billed or coded consistently from procedure to procedure. Various other providers including, facilities, hospitals, physician-to-physician, allied medical related providers, and providers of insurance or healthcare payers rely on a given data set to communicate goods and services provided to patients. These instances of services, procedures, supplies, evaluation and management codes are identified by The American Medical Association's® Current Procedural Terminology (by acronym hereafter as, "C.P.T"). C.P.T is essentially a standardized system of five-digit code numbers and descriptive terms used to accurately report the medical services and procedures performed by these healthcare providers. C.P.T was developed and the system is essentially updated and published annually. C.P.T is changed periodically by the American Medical Association (hereafter, A.M.A®). C.P.T codes are vital to communicate to providers, patients, and payers the procedures performed during a medical encounter. Accurate CPT coding is crucial for proper reimbursement from payers and compliance with government regulations. Other codes are used referred to as Healthcare Common Procedure Coding System (H.C.P.C.S, pronounced as "hick picks") codes and Center for Medicare Service (C.M.S) codes.

A second component to the aforementioned accuracy is a requirement to properly assign an International Classification of Disease commonly called, "I.C.D" (hereafter as, "I.C.D."). For all intents and purposes this I.C.D code is the most important data component to the data set to correspond to certain C.P.T as mentioned above. Needless to say, a "diagnosis" is the cornerstone thereto rendering any coded provider healthcare.

For all practical purposes, and the scope of this disclosure, I.C.D diagnosis codes are akin to another component of codes used and developed by The A.M.A®. To help translate or to help justify said C.P.T or related goods and services performed.

Methods of Coding

Procedural coding for a physician can be done by various methods. One way is coding from the patient's records by billing-office personnel. Therefore, by human intelligence these business and administrative people (non-health practitioners) take a stab at converting medical records into billing codes. These people also take a stab at making determinations about the providers' primary diagnosis codes from the records. This method maintains consistency of coding and also helps in keeping records current. An alternative is for the physicians to do their own coding, or for a designated physician to do the coding for all physicians in an organization. This has the advantage of the physician's insight and expertise. However, due to time constraints, it is often difficult for the physician to keep current with the charting responsibilities and changes in coding practice or code numbers. This is compounded by the absolute need to match C.P.T with I.C.D in some process before patient records can be accurately submitted. Regardless of the coding option chosen or process to submit vital patient records, all these cases are involving multiple codes, CPT procedures, ICD diagnosis codes and this process essentially rests and should rely upon the physician's expertise when code assignments of claims are made to other in this healthcare system of communication.

Therefore, when there is an inferior process for communication between required C.P.T and I.C.D codes then causes a broken system or miscommunication about vital data set. The superior art of this invention is to control the mismatch from being passed along in a process of communication as mentioned above to various providers that relay upon this data set to examine the statements or claims made therein claims process medical computer programs or by any manual means to examine the same data set in records at any point such information is transmitted to another person or entity.

Many codes are incompatible and cannot be billed for the same encounter. This invention has a mechanism to flag and to block certain double/duplicate billing or coding practices. To help avoid delays from inadvertent codes that is billed together. For example, this invention features a system to alert user/providers when two so called Evaluation & Management (E&M) C.P.T related code are stated on the same date of service. A coding practice that is not generally acceptable. Although, this is a feature of this invention, the superior art of this invention demonstrates novelty in additional ways. The superior art and method is more specifically described in disclosures of this invention. Problems like provider "unbundling" and the practice of provider "bundling" are coding business practices that bring heated debates in an otherwise standard system with reference to the use of C.P.T combinations.

Some claims are delayed from questionable coding practices effectuated by "unbundling" the billing code for certain A.M.A® C.P.T codes. "Unbundling" occurs when a medical or surgical service, procedure, evaluation and management is said by some to be described by a single CPT code and it becomes broken down by providers into purported components, and a bill is then submitted for each component and/or several related components instead of the C.P.T which describes the total code. A problem exists where different allied resources purport other coding practices that differ from The Authoritative Source, The American Medical Association's Original Article, like The United States Constitution, A.M.A describes the intended C.P.T, as it represents their "C.P.T" invention.

Not with standing, there is an extremely component to C.P.T, it is called the I.C.D or diagnosis codes intended to directly correlate to and to correspond to particular C.P.T. Otherwise, the process to prepare and submit patient's records breaks down. Irrespective of other aforesaid mentioned C.T.P people coding in a process assisted by computer programs or not. Therefore, a key component is the way ICD relates to each CPT code.

It is common practice for providers to use such codes to bill patients and other payers such as insurance companies on a common uniform billing form called a Health Care Financing Administration form (HCFA form) sometimes called a Health Insurance Claim Form. A HCFA form typically requires-C.P.T related codes to become matched to I.C.D related codes. The HCFA format has a standardized format in several ways. Accordingly, any discrepancy, incomplete data point and data set, or mismatch identified could cause delay in this claim process. For example, it is more accurate to submit a HCFA claim that represents that a C.P.T procedure for taking "X-Rays" is represented by a corresponding I.C.D diagnosis code that relates to a finding typically viewed on X-Rays, such as bone. By contrast to any healthcare provider submitting a HCFA claim wherein the I.C.D diagnosis code represents a soft tissue condition. Generally, soft tissue conditions are not viewed by standard radiographs or an "X-Ray" C.P.T procedural service code for the technical (to take X-Rays) or professional (to read X-Rays) components of this billing and coding process.

Clearly there is a need for the reviewing process to have a programmatic method or process to create a mechanism to allow a distinct match for each C.P.T with each I.C.D code. Moreover, some payers will require that I.C.D diagnosis codes be listed in a sequential order of importance. For example, the first I.C.D diagnosis code is generally the most important corresponding I.C.D to match up with each C.P.T service or procedure or evaluation and management code. The second I.C.D listed is next important, third next important I.C.D and forth I.C.D last important, respectively. Importance is how closely the I.C.D relates to the C.P.T and in some cases the first I.C.D is the only one that payers look at-in the process. This emphasizes the importance that the first I.C.D be the most accurate one to avoid delays in the process of claim submissions. Currently these decisions are made by people that are simply attempting to second guess what diagnosis the practicing provider licensed to make the diagnosis considered the most important one (primary or first significant) to justify the particular C.P.T code.

Clearly, there is a need for a process including a method and implementation in order to command communication in this process to assist treating providers.

Accordingly, there are basically three broad steps which can be implemented in the handling of medical related data, coding, billing and processing. 1) The "Superbill". Generally this consists of a hardcopy check off list of C.P.T code numbers and descriptions abbreviated one a single page. There is essentially no particular direct matching process or other system about this document. A mismatch of C.P.T and or H.C.P.C. therewith I.C.D code numbers remains left to human error. Often this page is handed to other administrative staff to determine ways to submit this data that provider may have completed on this format. Computer generated models essentially re-create the same model and the resultant is the same sorts of mismatching and other errors with code existing numbers. 2) The "H.C.F.A Form". This is a standardized billing format form developed to list information including C.P.T and I.C.D data. Past history will show that this form has been submitted more regularly by way of handwritten entries. The necessity to submit this form in electronic format and by computer in more recent times has been implemented. This form sorts out C.P.T and I.C.D in order to list a C.P.T and or H.C.P.C. to correspond to typically one of four (4) I.C.D codes. However, a drawback is that this form is recreated in an ex post facto sort of manner. Staff without first-hand or direct knowledge must make attempts to match up C.P.T with I.C.D, and they furthermore take a stab at attempting to make a first-hand determination exactly what diagnosis or I.C.D codes the provider's most important or "number one" diagnosis (representative by an I.C.D code) to list in priority, then number two, number three and number four (least relative importance). Whereas, this C.P.T and or H.C.P.C. to I.C.D matching method in the process is a key component. to make particular C.P.T and or H.C.P.C. correspond to I.C.D. In addition, it becomes necessary to list I.C.D assigned to each particular C.P.T in particular order as well. Any mismatch creates disorganization, havoc, and even life changing events to happen. Further aggravating this problem becomes evident when there are changes in healthcare practices, to code practices and staff that are not yet trained to up dated changes. Even when staff is intact, another event that causes chaos from small medical staff practices to hospitals, to other facilities, to very large healthcare organization and other providers of healthcare governmental regulators thereof. 3) Other Elaborate Computer Software Models. Although elaborate models have been used in practice, their drawback continues to be omissions of a system that demonstrates design implementation to create a match system for C.P.T and or H.C.P.C. therewith I.C.D. Again, a mismatch remains left to human error akin to afore said mentioned methods in disclosures. In fact, even providers with elaborate disclosed computerized implementation, related methods and systems, defer this process going back a (hardcopy) "Super Bill" method. Even with elaborate software related packages another drawback becomes the fact that code changes and staff changes. In such events, providers are left with a so-called "learning curve". Nonetheless, there needs to become a more superior "interim" method. The implement of this invention provides a superior method to re-create different codes that match code(s) typically used by a particular provider to describe the same goods and services. Whereas, certain components of this invention's code provides the same elements necessary for providers to function the same, even when changes take place around them. Elaborate database models can be up dated. However, this invention's model remains intact, even when it may become uncertain what changes in the code might become implemented in updated database. For example, providers using this application continue to virtually be using same codes, as the provider has become accustomed to learn and to use in practice to describe ones goods and services provided.

The so-called "Super bill" is an archaic method. Medical software related programs have been designed in very elaborate and variety of ways on the high-speed-internet highway. Not with standing, people using theses sophisticated programs continue to use the hard copy or even an electronic rendition or version of a "Super bill" in this aforementioned process to submit to payers. The Super bill method in this process is essentially a check off list. There is not a one-for-one matching process for each C.P.T and or H.C.P.C. checked and each I.C.D. checked on the paper form or even disclosures in computerized renditions of the same. In fact, some reviewers may actually discard one or the other codes. Without being absolutely certain heretofore with a reliable method and process that the more important code(s) set was not used, even discarded, in matching before claims are submitted to payers. The superior art allows this cross check and communication process using a method by the invention this embodiment created to be relatively certain. Billing and coding people play a role in the process. Regardless the various Methods of billing and coding people participating in various roles as discussed in the section herein. Medical providers need this reliable process, since licensed medical providers are legally known to be ultimately responsible for submitted claims in this process. Licensed medical providers make the diagnosis, and they cannot be second-guessed as to what diagnosis is more important than another diagnosis. This is an inextricable process that requires exact matches.

Moreover, codes change. This presents an even greater draw back to a process designed for billing and coding practices. This is most evident from unknowns about the test of so called "National Health Care" changes healthcare providers and the public at large shall be experiencing. When codes change there is confusion about accurate code numbers. The process faces yet other hurtles. This underscoring the need for a method in this process that will be superior over the art and standard billing or coding practices. This emphasizes the superior method of this embodiment in helping to execute the coding and the billing process that this invention demonstrates.

A five number code system is one difficult to remember. Given the fact there are literally thousands of C.P.T and I.C.D code numbers. One can recall many, until the system or process changes. This causes another delay in the delivery of healthcare goods and services, procedures, evaluation and management or C.P.T codes by numbers. Disclosures identify typical five number (or longer) codes, and some are even mixed in complicated ways with abstract letters or modifiers in the case of C.P.T codes and even I.C.D. codes.

Therefore, there is a significant need for a relatively affordable, light weight, faster and more adaptable to change type of implementation which shall greatly improve and promote communication among health care providers, treating providers, their staff, patients and others in a world of other busy life styles and domains.

SUMMARY OF THE INVENTION

This Invention's Routing Template (RT) Part

This invention created a method used in the coding and subsequent billing process that is novel in several ways to change the code numbers into easy to remember code letters. Typically only three or less letters are used to replace code numbers. More specifically, the simpler letters are in the form of a method inventor is calling a programmatic mnemonic texting technique and aspect, respectively. For example, the C.P.T code number "99213" is a C.P.T code number to represent a certain level office visit. The number has a very long CPT description to specifically describe the CPT codes even more. Each CPT Category often consists of a long series of additional similar CPT code numbers that can be used. This novel invention has a method of programmed and programmatic mnemonic recognition and a method to convert the long complicated code to simply "OV", a two-letter code. Hence, the busy medical provider concerned with delivery of healthcare can simply enter the code letters "OV" in this program. Physicians are less concerned about the changed C.P.T and or H.C.P.C. code number descriptions. The provider will thereby programmatically always recognize "OV" as "Office Visit", when stating the services for accurately submitting the claim in this process. Whereas, administrators or office and business related billing/coding people make the necessary changes to the computer program behind the scenes. Perhaps the greatest novelty that this application method is designed with functionality to convert and correspond CPT and or H.C.P.C. to any of the changed or updated C.P.T and or H.C.P.C. number and description codes. More specifically, by allowing users/providers the method of assigning an easy mnemonic code letter series. Typically, only three letters and sometime fewer letters. Doctors need not agonize over entering wrong numbers and long changed code numbers. "IOV" for "Initial Office Visit", by contrast to separate series of codes for those types of Evaluation & Management code numbers. "I&D" for Incision & Drain replaces a long complicated abstract procedure code number, and the letter code is entered into this novel computer program application invention. By contrast to a long code number and a code number that may have implemented changes in the healthcare system, and so forth on. Providers could even customize code letters that help them more easily recall the service, instead of long complicated and even one implemented by changed coding number system, such as National Health Care or any other recreations to change standard uniform coding system used by the professional community to communicate vital healthcare information to other providers. In short, the end user virtually always will use the same house code, "OV" for example, even when numbers and other changes become effectuated around the provider. Even when staff leaves. The provider can continue due course of business. Until the appropriate administrator can make changes to correspond to the code letters provider becomes more accustom to utilize by this novel computer method related machine application of the invention.

The codes submitted to payers are translated and sent in the updated code number form and as the code numbers have been universally standardized, accepted or changed. This method is essentially an in house system and process personalized by this novel computer application methodology.

This Invention's Scheduling Part

Another element is a method to provide communication from the provider to the patient and to people scheduling follow up or return visits for patients. This invention's superior art has a programmatic method to maintain a connection or flow from treatment or "back" clinical area to business or "front office" appointment desk. Furthermore, a Patient Appointment Card ("PAC") is printable to provide a convenient and reproducible method to insure patient-provider communication with reference to recommended return visits. Although, these related "scheduling" features taken alone might be obviated heretofore disclosures for elaborate medical machine programs and implementations lack processes that incorporate this communication method. Once again, and as with the routing template part and as mentioned above, client users implement this novel computer method related machine application of the invention. Although, this is a superior feature of this invention, the superiority of this invention demonstrates novelty in additional ways. The superior art is more specifically described in disclosures of this invention. The application further allows user to touch/click patient's contact information in order to directly contact or notify the particular patient. For instance, by e-mail or by a pre-scheduled or instant phone call directly from the application on a phone or computer able to make "telephone calls" or what might be referenced as an "Internet Phone System" or form of "Voice Over Internet Protocol, VoIP" system.

BRIEF DESCRIPTION OF DRAWING

The above and other advantages and features of the invention will become apparent when the following description is read in conjunction with the accompanying referenced drawings, in which:

FIG. 1 is an embodiment of routing template and scheduler parts;

FIG. 2 is an embodiment of routing template and scheduler parts;

Figure 4:
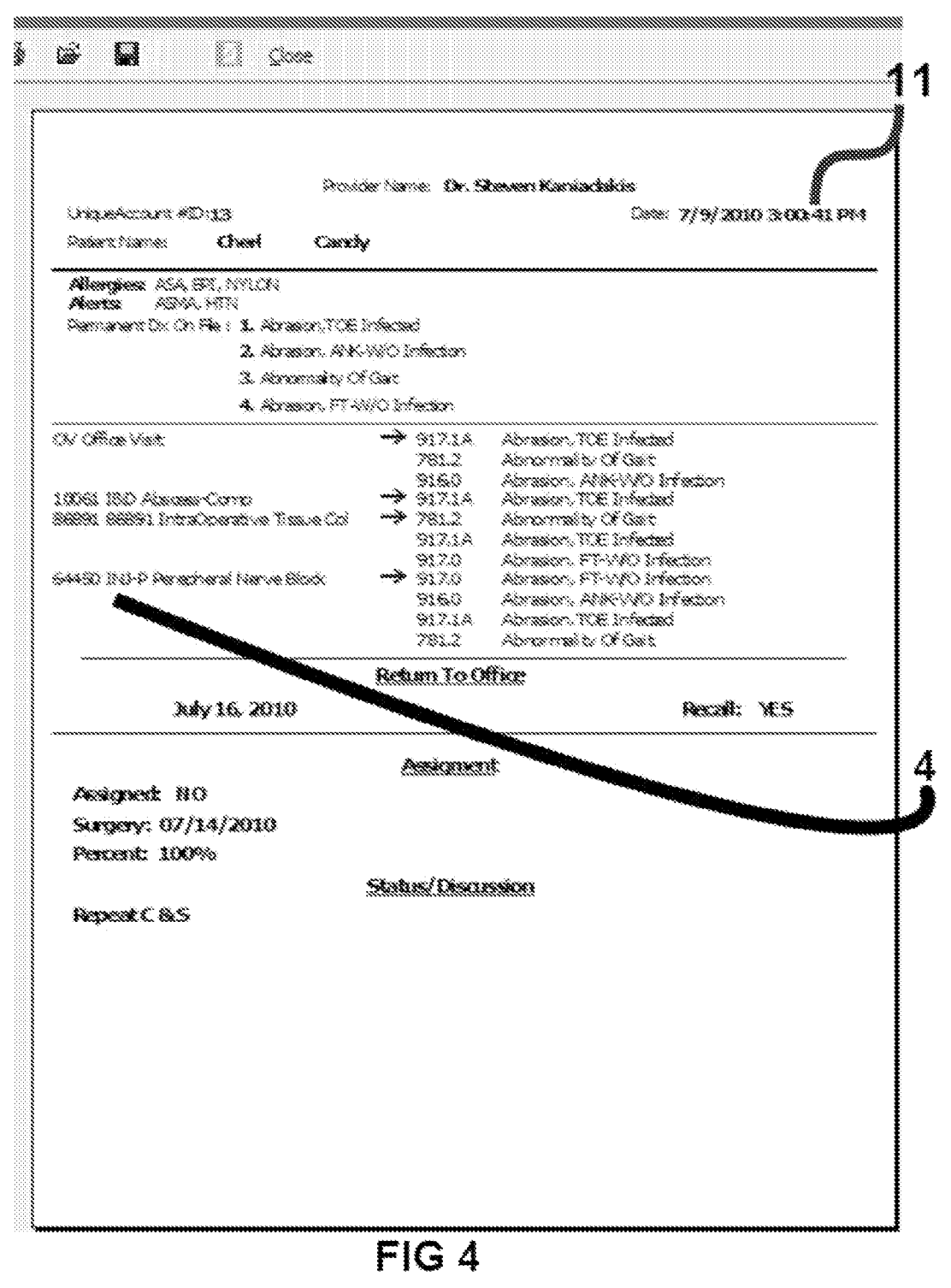

FIG. 4 is an embodiment of Preview page. Novelty code numbers/code letters, part 4. With inventive face-to-face encounter counter, upper left static time/date captured. See FIG. 32;

FIG. 8B top, is showing first embodiment contacting and calling patients from upper part of Main Appointment Page (MAP screen), 1, 2, 3. Lower is showing, display screen from first embodiment with invoked Patient command graphic, and the symbol to add the contact and account data;

Figure 13:
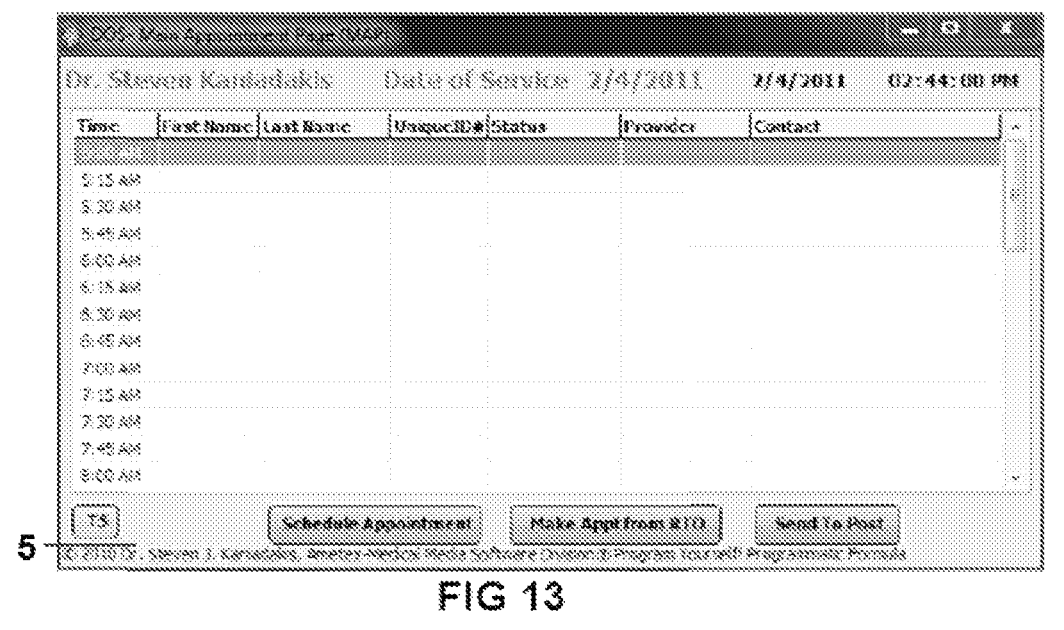

FIG. 13 displays upper part of Main Appointment Page (MAP screen). Scheduled appointments, unique chart identification system, to invoke contact section implementation, to invoke touch screen (TS) command implementation, to invoke send to post (STP);

FIG. 5 is implementation of touch screen for RT and Main Appointment Page (MAP);

FIG. 26 displays the invoking of the Return To Office/Assignment field (foreground) by respective command graphic acting as a button at distal and inferior most aspect of Routing Template (RT) page (background). Data sorted and sent to Main Appointment Page (MAP) screen to be sent to post. See FIGS. 11C through 11F, FIGS. 34, 36." See FIG. 27;

FIG. 28 shows first and practical embodiment with a field for converting code letters into code numbers 4. This is showing a CPT related field for information and data. The command controller, cursor, or arrow pointer is shown. Programmatic texting aspect text and anticipating some results immediately inferior 6 to the box as letters, code, or description is entered into this field or box (superior). See 39;

FIG. 29 shows each diagnosis in reference to the fields as mentioned and illustrated in FIG. 9;

FIG. 31 shows ICD (diagnosis or Dx) can be added or removed from fields 10. See position number four in Add To field. Note CPT in the CPT/Dx housing field 7 is only related to diagnosis in permanent diagnosis field position number one (1.) at this time. First diagnosis (any Dx number assigned) is placed into first place after CPT in CPT/Dx housing 7 field It can be Dx1, 2, 3 or 4 8;

Figure 34:
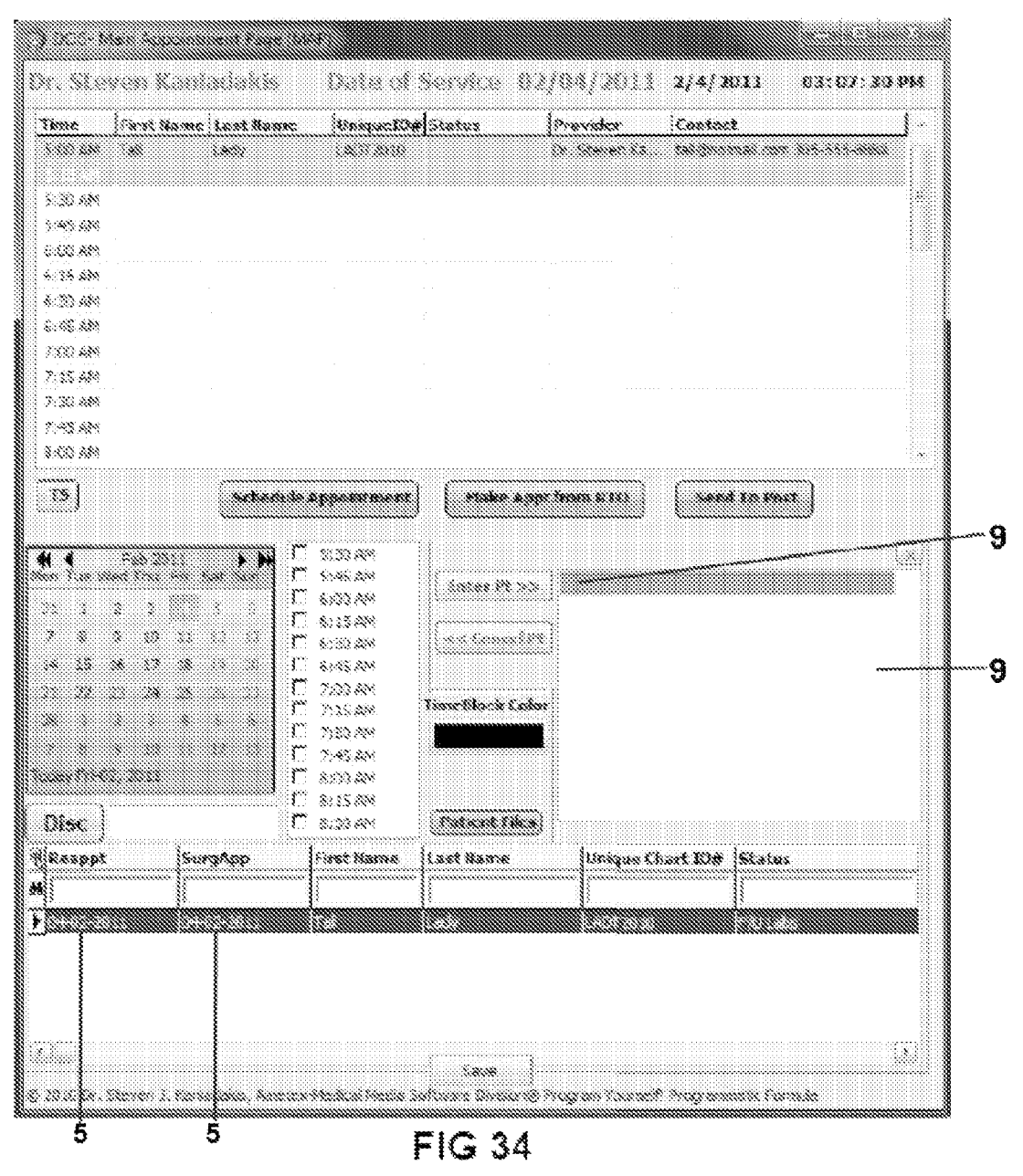

FIG. 34 shows a scheduler, lower part of Main Appointment Page (MAP screen) 5 shows data sorted and date and reason for return ("status", event, task, reminder), surgery date and regular appointment date. See FIG. 36;

FIG. 40, showing how to send e-mail (foreground) directly from the appointment book (shown in background). Just invoke command graphic, or say 12 FIG. 5 call and phone the client or patient right from the 5 appointment book;

FIG. 44 touch key board. FIGS. 45, 46 takes audio commands, saying house code letters "OV" will display. Clip board hook feature and pointer controller 12 moves in a touch-less action via audio commands and speech;

DRAWINGS REFERENCE NUMERALS

Figure 3:
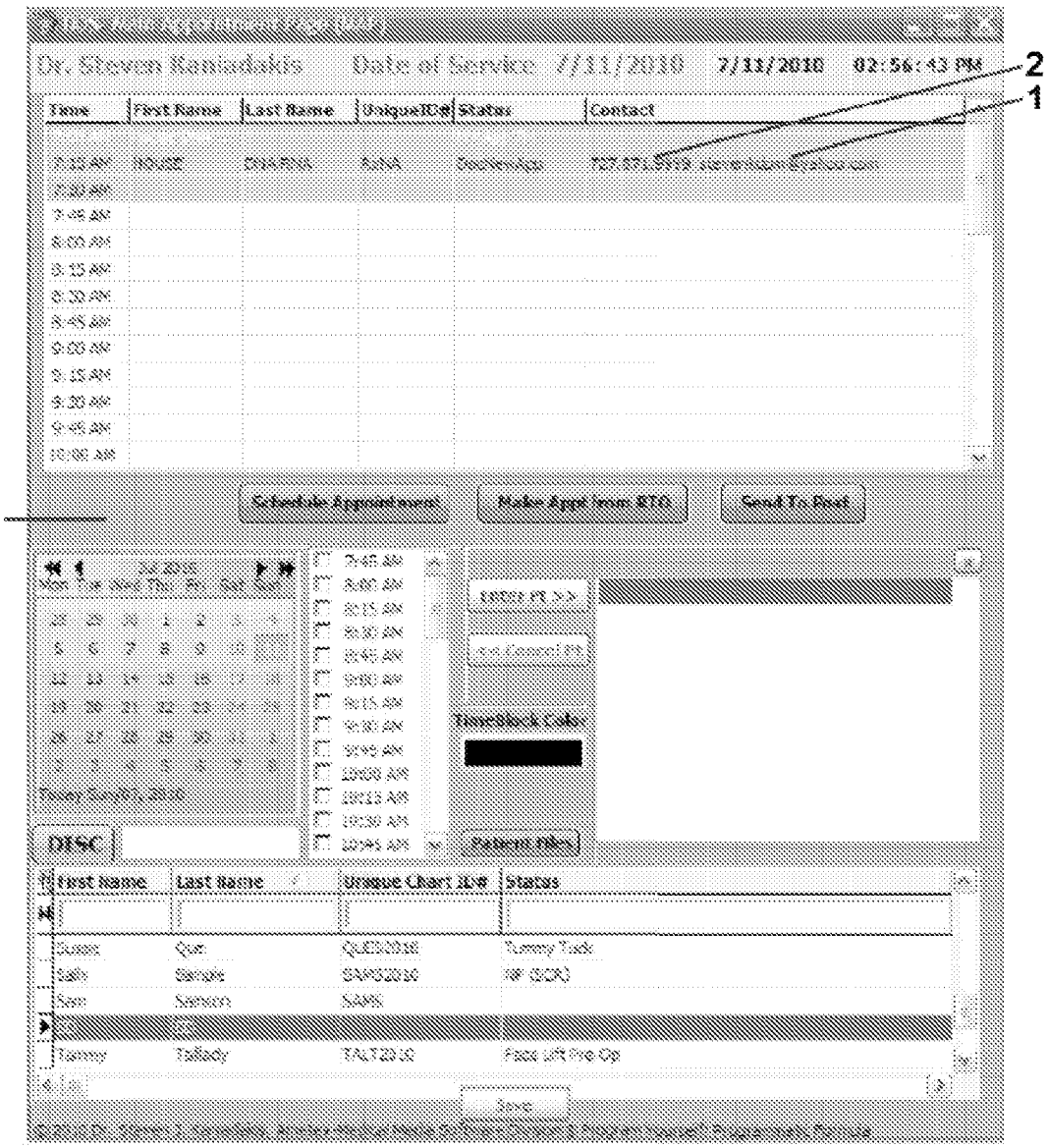
FIG. 3 is an embodiment of routing template and scheduler parts.

4 an in house code conversion field 5 a dynamic calendar and appointment 9 appointment card 2 interactive phone command graphic 6 a programmatic mnemonic texting field 1 interactive e-mail command graphic 10 command graphic 12 controller 3 a database table 7 housing field 11 a time date docket 8 drop down diagnosis selection box

DETAILED DESCRIPTION FIRST EMBODIMENT

This invention essentially co-ordinates flow of information from clinical staff to business staff in a bi-directional manner in order to allow a more exacting communication about patient's healthcare related information. This invention conducts this process by essentially one general way. The use of a unique "Routing" Template is a method utilized, and this part of this invention is described more specifically herein.

This invention utilizes a patient scheduling method that is closely related to this embodiment's Routing Template page or screen as presented more specifically herein.

Although this invention's automated scheduler part is unique and superior and especially adds to the flow as part of the Routing Template part, this invention works apart from this scheduling device that is more specifically set forth later.

Figure 1:
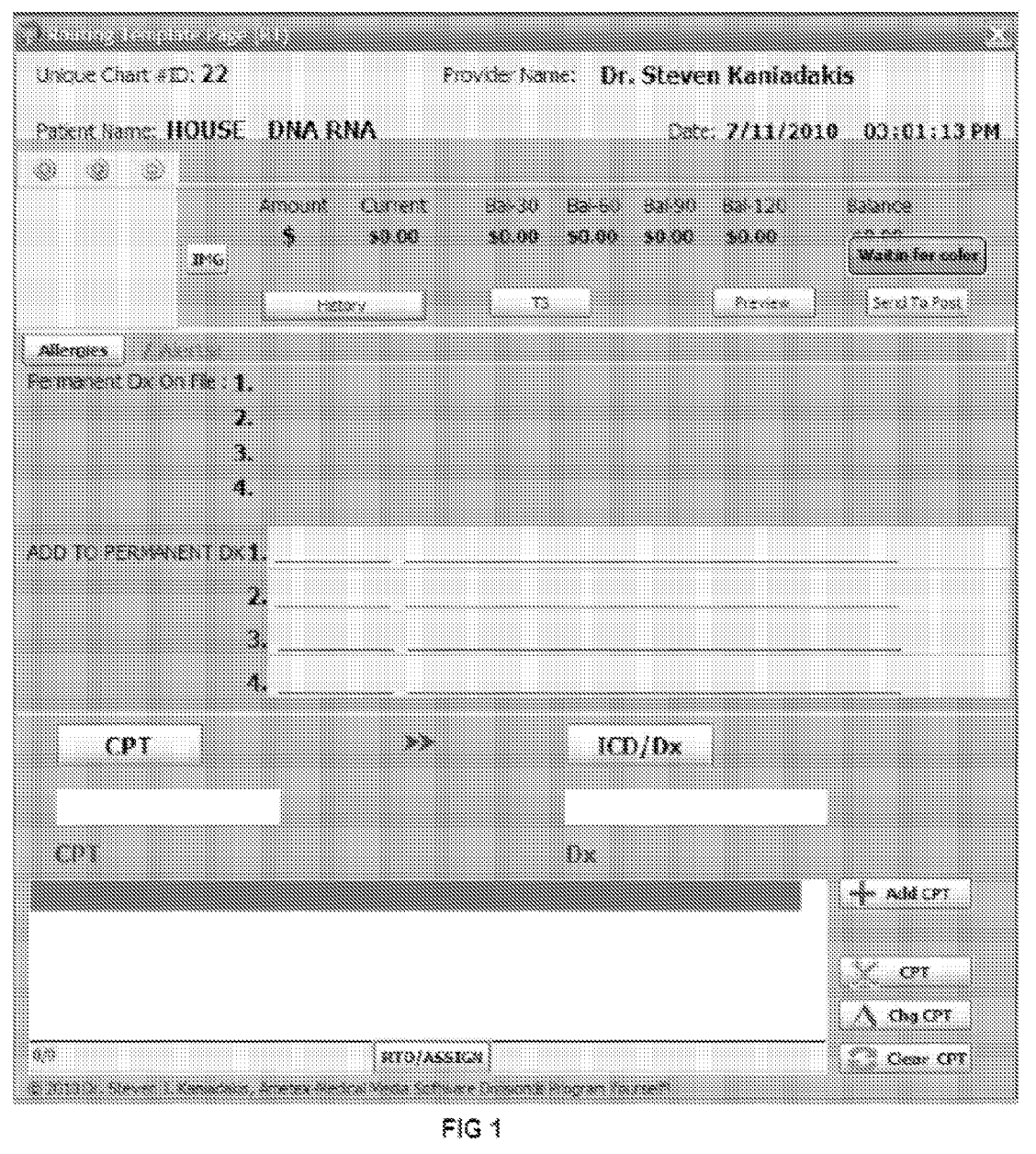
Figure 2:
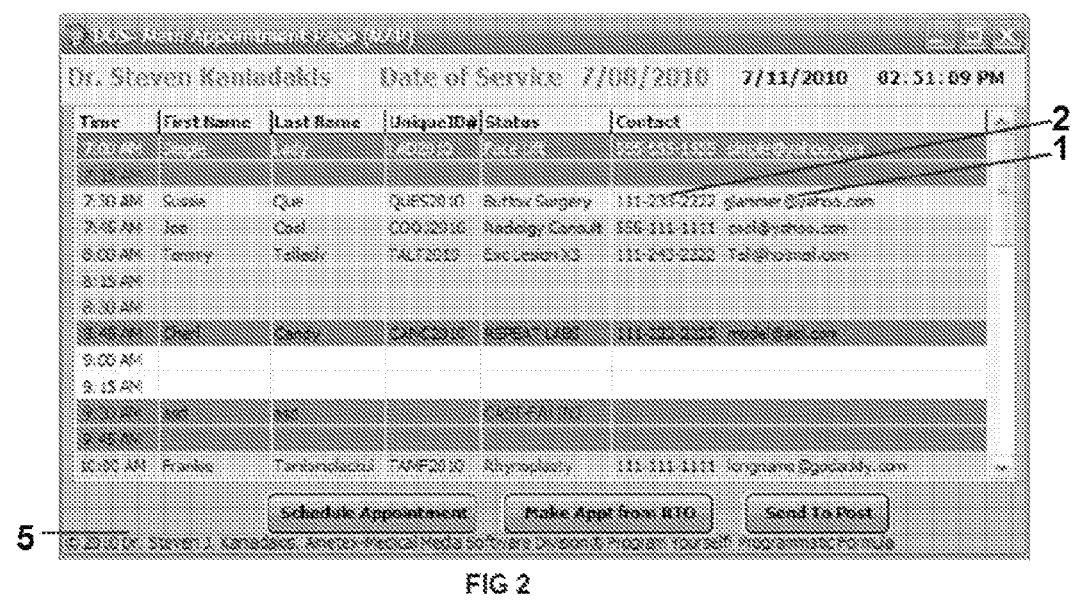

Although this invention's Routing Template page or screen is essentially central to superior art. Therefore, the anatomy of this invention's Routing Template page or screen is described first before (FIG. 1) this embodiment's scheduling art (FIGS. 2 and 3). Tools that drive the machine and executing logic and functionality that may become obviated by the logic and this invention's art is detail to be discussed later.

This invention acclaimed unique design implements a simpler code translating more complex code as mentioned first in the "Abstract" hereof. Therefore, this invention introduces and utilizes the use of an application as an instrument or model for implementation of a unique superior art to create a process of communicating very complicated issues involved with medical records and this is now more specifically described.

The customary code remains unaffected by this invention when communicating to others unfamiliar with the ease of this application. Typical code practices are known to cause confusion when changes are implemented beyond the control or providers of healthcare. This obviates a need for a system that serves a role until changes are implemented and everyone comprehends matters about the changes made to common code. This invention offers a synchronized effort to place users on the "same page" in the meantime, until mayhem is organized.

Figure 20:
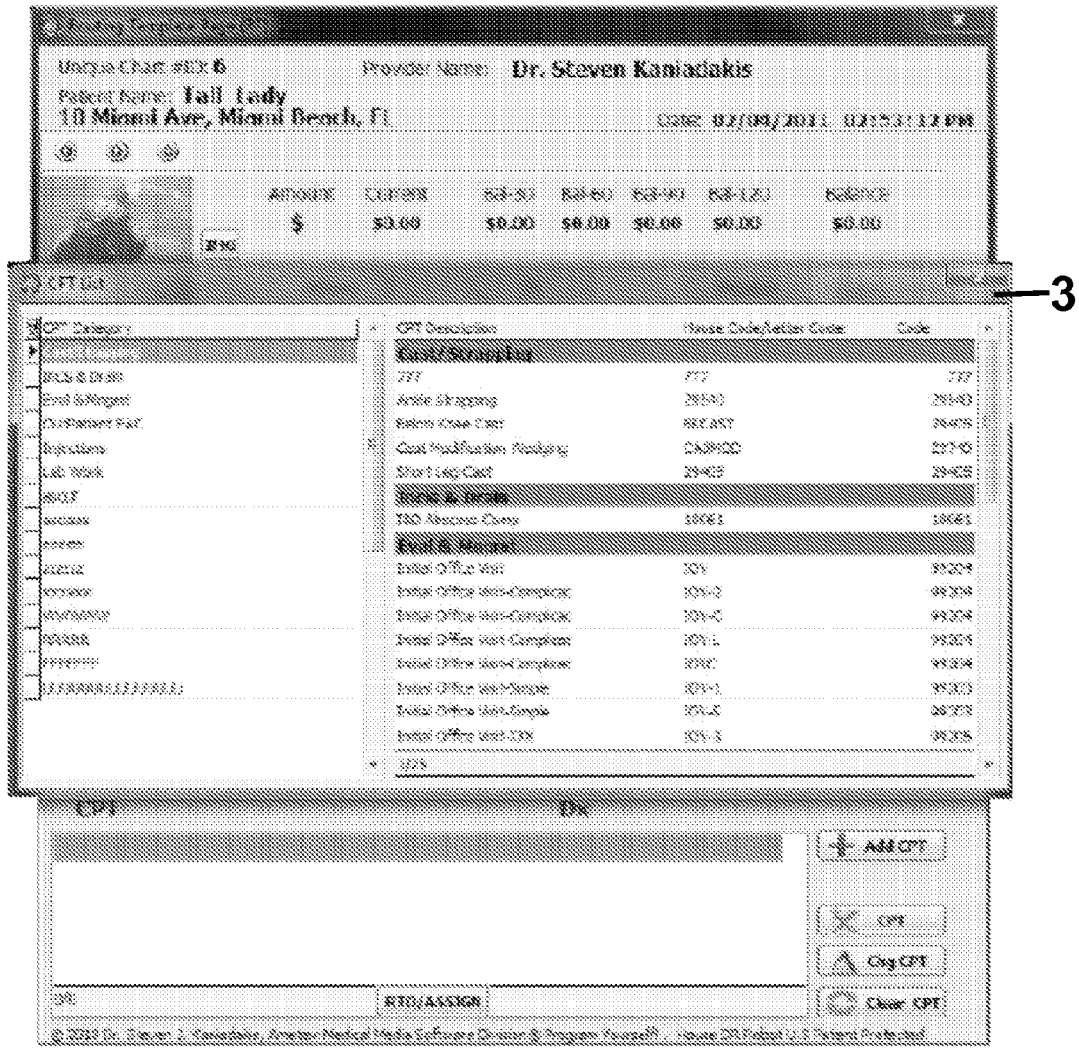
FIG. 20 displays first embodiment of a Routing Template page screen component. Compare to FIG. 1/FIG. 10. CPT data base 3 pop up (foreground) with invoking reading CPT command graphic action acting as a button on Routing Template page (background). Compare and contrast with FIG. 28/FIG. 39, programmatic mnemonic texting aspect acting as a predictive code field box, using code numbers or code letters or code descriptions.
Figure 28:
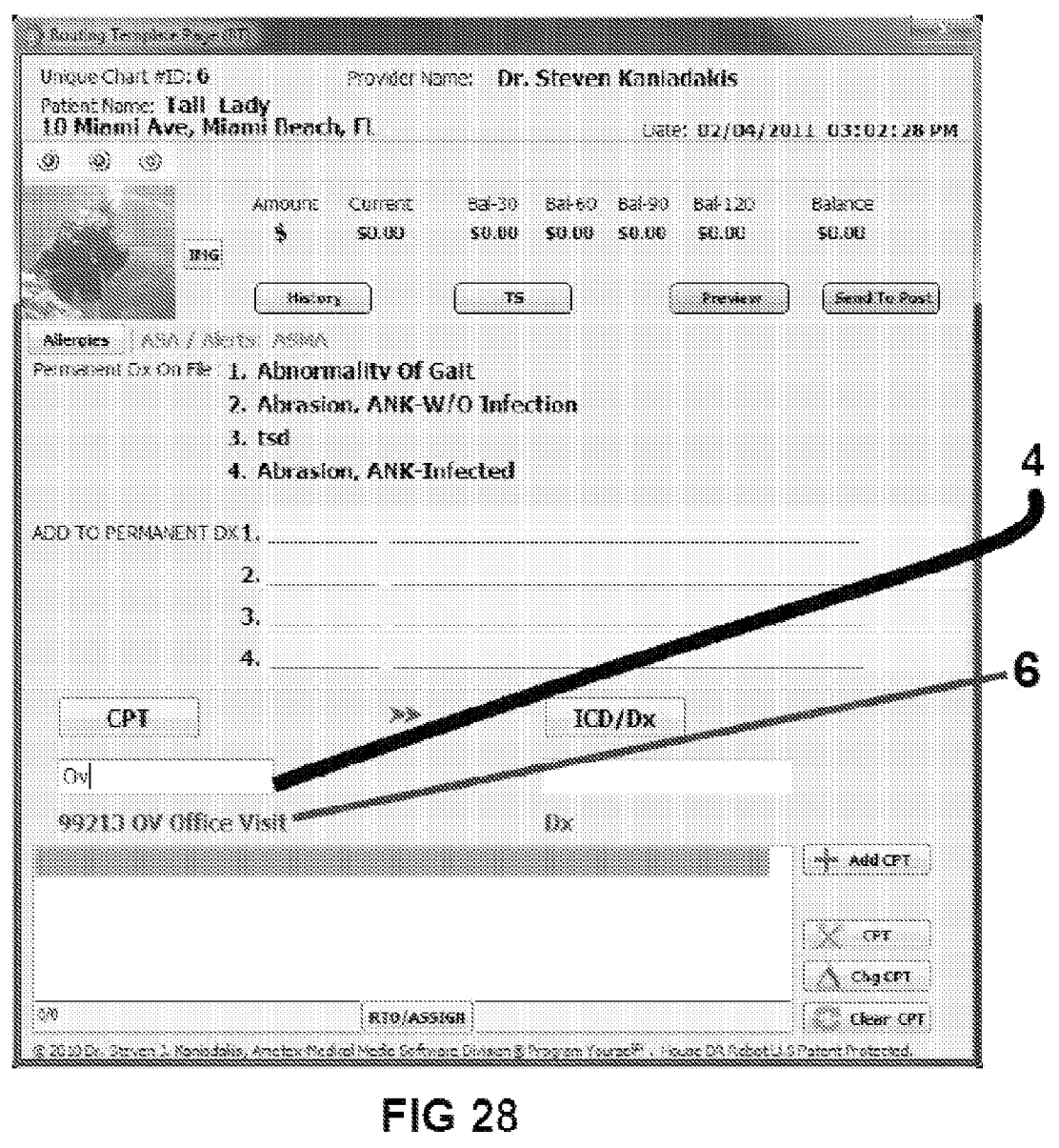
Figure 35A:
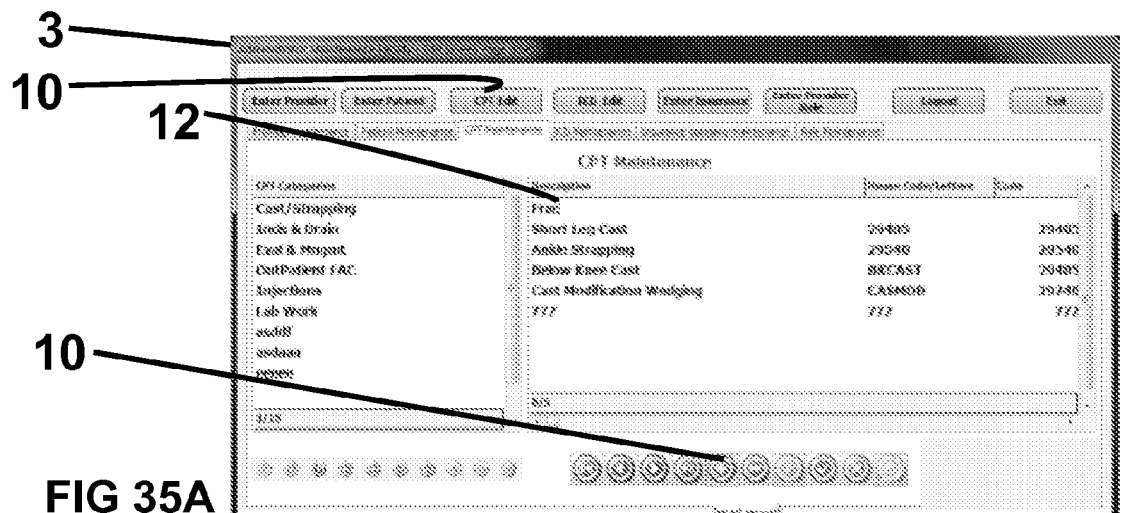
FIG. 35 shows a the first embodiment's display screen invoked, called the Edit Screen Page (ESP) FIGS. 35A CPT, 35B ICD.
Figure 39:
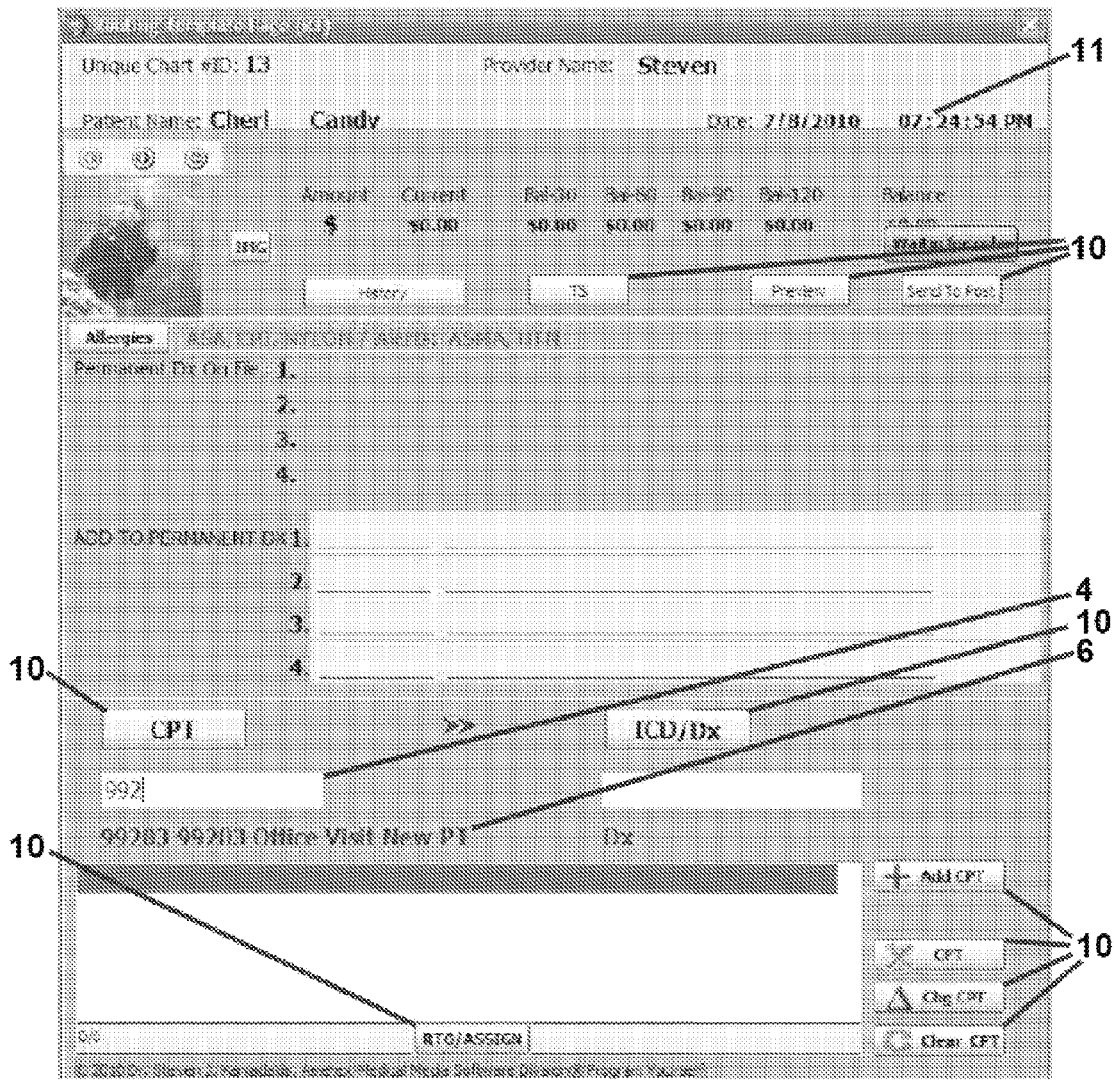
FIG. 39 is a previous embodiment of Routing Template page. Programmed texting moving action 6 called programmatic mnemonic texting field. The command controller, cursor, or arrow pointer 12 is shows fashioning code 4 and the Programmatic texting aspect 4, 6.
Figure 48:
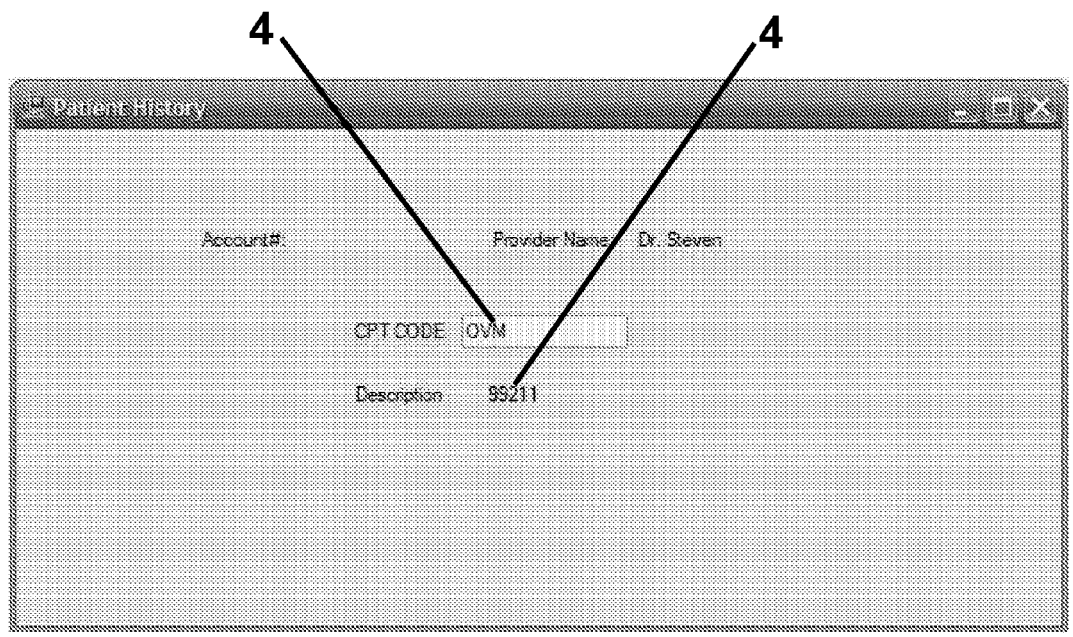
FIGS. 48 and 49 shows a simple demo/model. Displays a screen view. Previous embodiment showing the part that converts code number descriptions.
Figure 49:
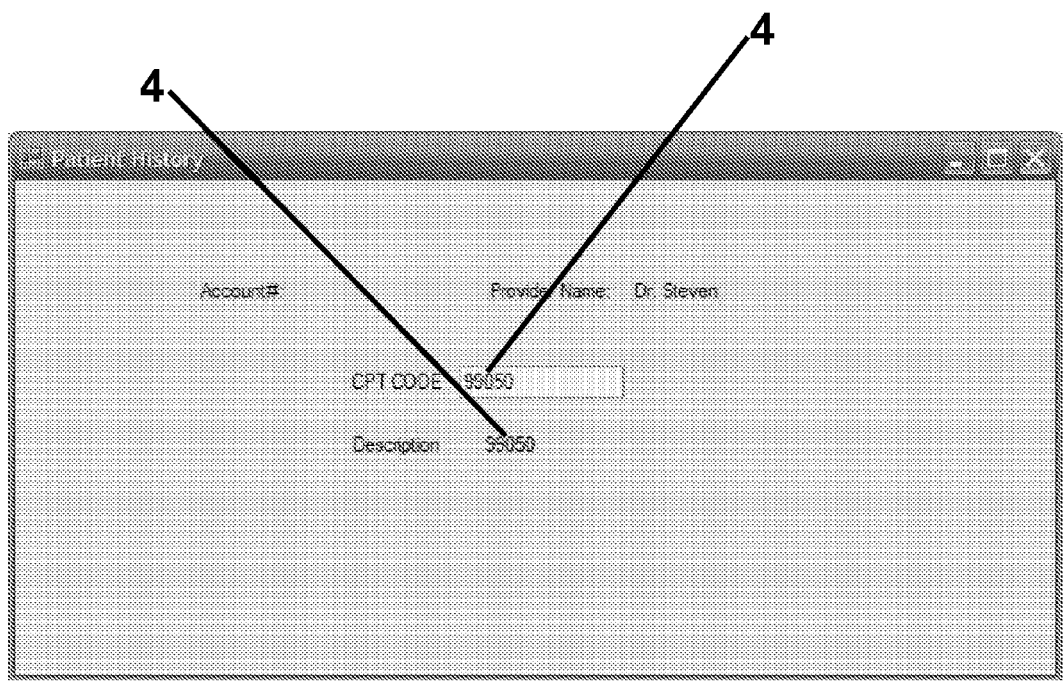

This application is essentially designed with a method for each end user to accordingly create their own unique simplified said mnemonic code, words or letters, anticipating each textual input from user's database tables and in order to translate a relatively complicated code system utilized in common practice by providers of healthcare. FIGS. 35A and B. FIG. 35 shows the first embodiment's display screen called the Edit Screen Page (ESP) FIGS. 35 A CPT, B ICD, showing command graphics 10 with controller 12 for editing and invoking respective database 3 data points and data point sets and synchronizing data on routing template and calendar contacts. Therefore, a central figure and component part and heart vessel of this invention can be illustrated with screen views shown as representative by FIGS. 48 and 49. This invention shows for illustrative purposes a fundamental working element and a part of the driving force of superior art of invention's Routing Template (at FIG. 1.). This invention's embodied model at FIGS. 48 and 49 shows two (2) screen shots for illustrative purposes a fundamental working apart; Namely, FIGS. 48 and 49 show a way art translates any code number(s) to virtually any said mnemonic code. This invention described typically uses code letters as representative in FIGS. 48 and 49, representative code numbers and vise-a-versa action. FIG. 28 shows novelty of the present art which is including into convert code letters into code numbers. Here this is showing a mnemonic field which is acting as a predictive value text box field for CPT and or H.C.P.C. related information and data. The action of a command controller, cursor, or arrow pointer is shows fashioning code. FIG. 28 and FIG. 39. Programmatic texting aspect acting as predictive text displays results immediately inferior to the box as letters, code, or description is entered into this field or box (superior). Data is extracted from FIG. 20 related fields, patient files and/or administrative super user screen fields that are synchronized. Patient history and progress notes in fields of touch screen, FIG. 5. See FIG. 10, Part 4 and FIG. 39. Whereas, this invention's method and things are more specifically described herein. Refer to each disclosed embodiment of this invention herein. Whereas, FIGS. 48 and 49 are illustrative as an essential element or component. FIGS. 48 and 49.

Material previously filed as "Unpublished" with U.S. Library of Congress including FIGS. 48 and 49 are hereby submitted herewith; FIG. 28 and FIG. 39. These aforesaid mentioned drawings are illustrative of an in action view and screen shot showing code numbers and the client's code letters being converted 4 such that "OVM" data point yields "99211" data point and "99211" yields "OVM" 4. Data entry of customizable or unique code letters "OVM" for a code description as an "Office Visit Minimal" level of service evaluation & management code becomes easily converted to standard code number typically representative of one of the same in a universal coded language employed by providers of healthcare professionals and industry. A data point set is created when the client may create an in-house code letter series data point to correspond thereto a data point of a code number and a description thereof. The reverse action and code works to translate back to the first code. Enter a number function into the programmatic mnemonic texting field aspect, and a code number entered in pure form yields code number 4 and code description. "99050" yields "99050", thereby original article remains intact. To maintain traditional code language generally by convention. FIG. 28 and FIG. 39.

Thus, this invention's most simplified statement is described as illustrative in FIGS. 48 and 49. "99211" yields "OVM" and "OVM" reverse yields "99211" 4. The first code number is changed to code letters in this instance, and the second code that becomes representative by code letters 4 is created by user or part of database 3 in converted form. FIGS. 35A and B. Whereas, this invention's superior art involves more parts to this modification than as shown from FIGS. 48 and 49 as it will more specifically be described herein. There was not a mechanism to perform this in a consistent manner, to maintain and restore the pure form of the code, and to process accordingly other medical records and medium existing before this invention as more fully described herein. The belief is that The American Medical Association "C.P.T" code and related codes are in fact intended to be the original article for communication, and this is described more fully later. Therefore, this invention is not intended to make merely renditions or versions of bundles or packages of the same code in other modified ways.

A key component of this application method is that the first code number as defined by a universal standard remains in database to be utilized when communicated or when transmitted to other parties outside the domain that this invention is employed. For example, although the first code, initial or original code representative thereby "99213" FIG. 39 has become converted 4 becomes created by the next user of this application to "OV" FIG. 28. as a second code (a changed code) 4 it remains the instrument to communicate by necessity the first code to other providers. Therefore, the communicated standard code (language) is the first code. Wherein the next user of this application second code (or changed code) becomes a sort of proprietary code for the provider's domain. The underlying principle is that the first code represents a set of codes that remains the trade or professional communities' code and language.

Prior examples of inventor's own art exist showing as other embodiments thereof. Invention akin to those described by "Morris Code" communication by wire, except this invention submitted herein is to allow the code to remain decoded unlike "Morris Code", when this invention application becomes sent, and this is novel to this invention submitted. Whereas, this present invention is a method for producing and for changing a machine including non-transitory machine readable storing and changing a computing system, The invention is not a signal and per se a code itself. Furthermore, the present method is a customizable code which is corresponding to a standardized decoding method for different user clients. Whereas, the first code may indeed be a code that is used by tradition, convention, universal, or standard, the first code may not be limited to any standardized code, and the first code may indeed be a customized or code designed by another party other than example given herein with The American Medical Association. This example is not intended to limit the scope of variations in code, it is the mechanism to convert a code and when used in combination to an instrument akin to a Routing Template page or system described herein. Whereas, this invention disclaims property of database owned by the first code, such as The American Medical Association "C.P.T" code.

This invention does not claim to be making a change to American Medical Association's C.P.T apart from this invention's use of C.P.T as an example for medical records.

This invention disclaims exclusive use of C.P.T, I.C.D., H.C.F.A, C.M.S., H.C.P.C.S, and others that may become used for demonstration purposes apart from this invention. Ironically, three letter or four letter codes to describe these codes, such as "CPT" or "HCFA" heretofore, this invention takes actual code numbers therefrom "CPT" and "HCPCS", for instance, and this invention actually makes these code numbers simple to abbreviate as part of this invention's method. Therefore, this to clarify that said code is often referred to by a three or four letter code or abbreviation acronym. In practice the respective codes are not as easy as three or four letters. This invention beyond the task of producing mere acronyms or simple manipulation of existing data, as set forth.

The American Medical Association's Current Procedural Terminology is represented by the acronym "C.P.T". The C.P.T typically consists of a set or a series of sets of long code numbers. These numbers are harder to remember. A short hand method is described by this method that becomes reproducible to the original code and to a user creating a short hand note for such code numbers in practice. This application makes reference in citations sometimes only as to CPT, however, in these cases applicant's intent is including and or H.C.P.C. code number descriptions as well.

This invention created a method novel in several ways. The embodiment is including, among other things to be described, a method providing a computer or computing device and a means for converting difficult or long and complicated billing code numbers into easy to remember code letters. Typically only three or less letters forming a data point are created by a client FIGS. 35A and B and subsequently used to interchangeably and automatically replace billing code numbers as another data point. More or less code letters can be implemented, and the use of symbols may be utilized. More specifically, the simpler letters are in the form of a mnemonic method and technique. This is a distinct design superior to prior art, since human intelligence could easily recall this information. The method makes reviewing medical related data for examination of case records becomes easier for the client. For example, the billing code number "99213" is a data point used to represent a certain level office visit, a code description data point. This novel invention has the special Programmatic recognition method to convert the long complicated code to simply "OV", a two-letter code data point. Any code letters can be used by the health care providers rendering care, coding, or in the billing process.

Hence, a busy medical provider concerned with delivery of healthcare can simply enter the code letters "OV" into this program. A medical provider is less hampered about as much by and concerned about by any effectual changes in billing code numbers. Therefore, the provider will always recognize "OV" data point code letters as "Office Visit" data point code description when stating the services for accurately submitting the claim in this process. Whereas, administrators or an office and business related billing/coding people make the necessary changes to the provider's computer or device's operation. This is generally performed behind the scenes by business related staff and administrative staff. Physicians and other health care people need not agonize over entering wrong billing or code numbers and any "change" thereof any of a data entry involving medical related information, including the medical code numbers.

Human intelligence can easily ascertain what each of these mnemonic code letters mean as the invention's method is automatically texting and using a programmatic aspect causing a mnemonic texting feature. This method shall replace a long complicated, abstract, difficult procedure code number, or other billing code numbers that have changed via providing a programmed texting anticipating the next letter, descriptor, character, number, word including anticipating the medical code sequence series and description. Change typically causes errors and omissions, even bad results punishable by law. Whereas, in medical records the method of using letters instead of numbers to depict procedures, supplies (typically given as HCPCS code), evaluation and management billing codes become an easy task for machine readable information in extraction from medical records. For instance, in the medical record "INJ-C" dictated and transcribed in the medical record or progress notes equated to "injection of cortisone" by another method of the elements to the method using an artificial intelligence operation, including afore said programmatic mnemonic texting and the programmed texting aspect.

This present invention's method is producing an artificial intelligence for performing this machine method providing computer and computing device readable program instructions and non-transitory computer readable storage in the client's memory and in each the clients' data base for the code number descriptions and for the client using any created code letters (descriptors and phrases). FIGS. 35A and B. A data base with human intelligence creating artificial intelligence, converting billing code language, and machine that recognizes the language in terms of letter used in the billing implements (such as, what is called a "Superbill") as the complicated code numbers or symbols or coding descriptive phrases, "injection steroid was performed" in extractable medical records will become equated to the specific acceptable standardized billing code number before sending to third party payers that recognize standardized billing codes as these are converted from code letters or code descriptive phrases back to the difficult code numbers.

This present invention allows superiority over the plurality of prior art. There is human intelligence in making the medical record. This present invention is using an artificial intelligence process produced via method, and a non-transitory method using machine readable set of instructions. A product of this invention's method is including human readable billing codes.

Whereas, the creation of code letters can be considered as the primary fundamental design for operative implementation in this present art. The ideal method, operating this system for billing codes and medical record extraction would have a plurality of this prior art and be superior in other design to overcome limitations of prior art identified. Accordingly, prior art has limitations in a plurality of ways as it will be shown herein.

The present design utilizes an unique method to apply and help process typical medical related code, medical terminology and other descriptions, utilizing a unique medical implementation related application program to perform this method. A machine related application program created a method to help process and to facilitate processing of medical information with a more exact method for tracking or routing of patient's medical information.

Routing Template (RT) Page Screen Part

This invention's Routing Template page or screen is essentially central to superior art as it has been mentioned herein. Therefore, the anatomy of this invention's Routing Template page or screen is described first before embodiment's scheduling art. Tools that drive the logic and functionality that may become obviated by the logic and this invention's art is detail to be discussed later.

FIG. 1. A Routing Template (RT) page screen view. Anatomy from superior to the lower aspects opposing caption.

Figure 10:
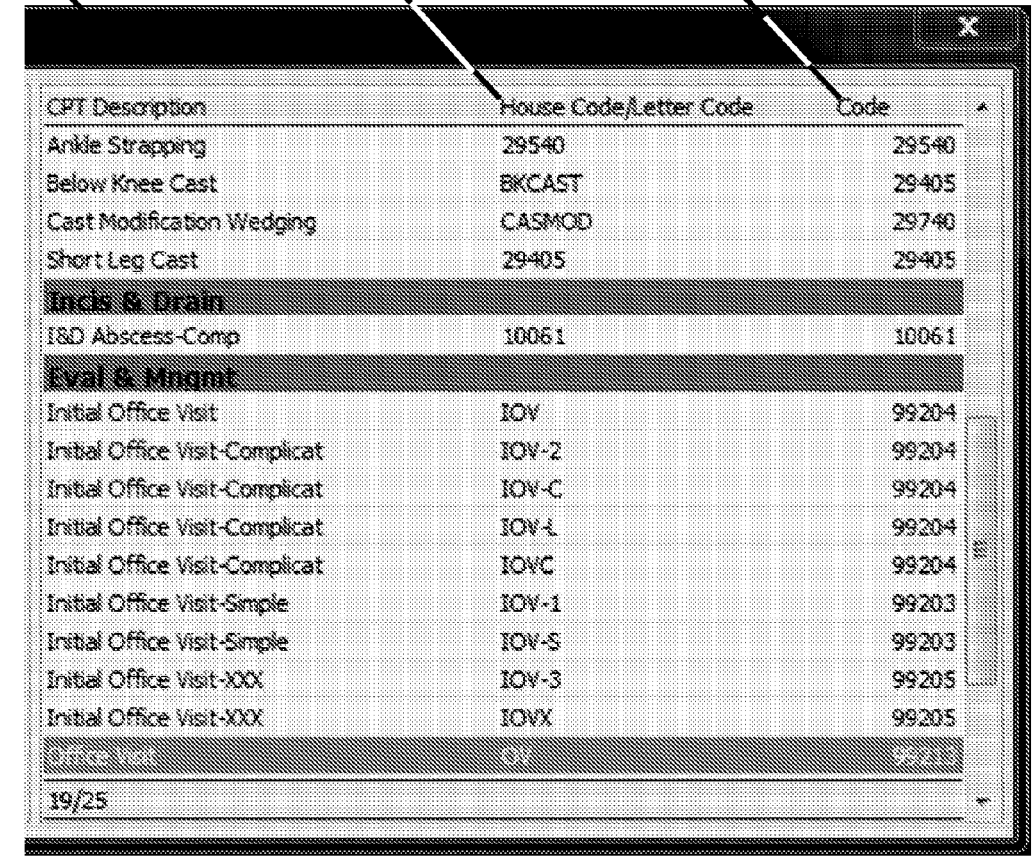
FIG. 10 is first embodiment shows CPT databank corresponding code descriptions, code numbers and code letters, 4. Compare to and FIG. 20.
Figure 21:
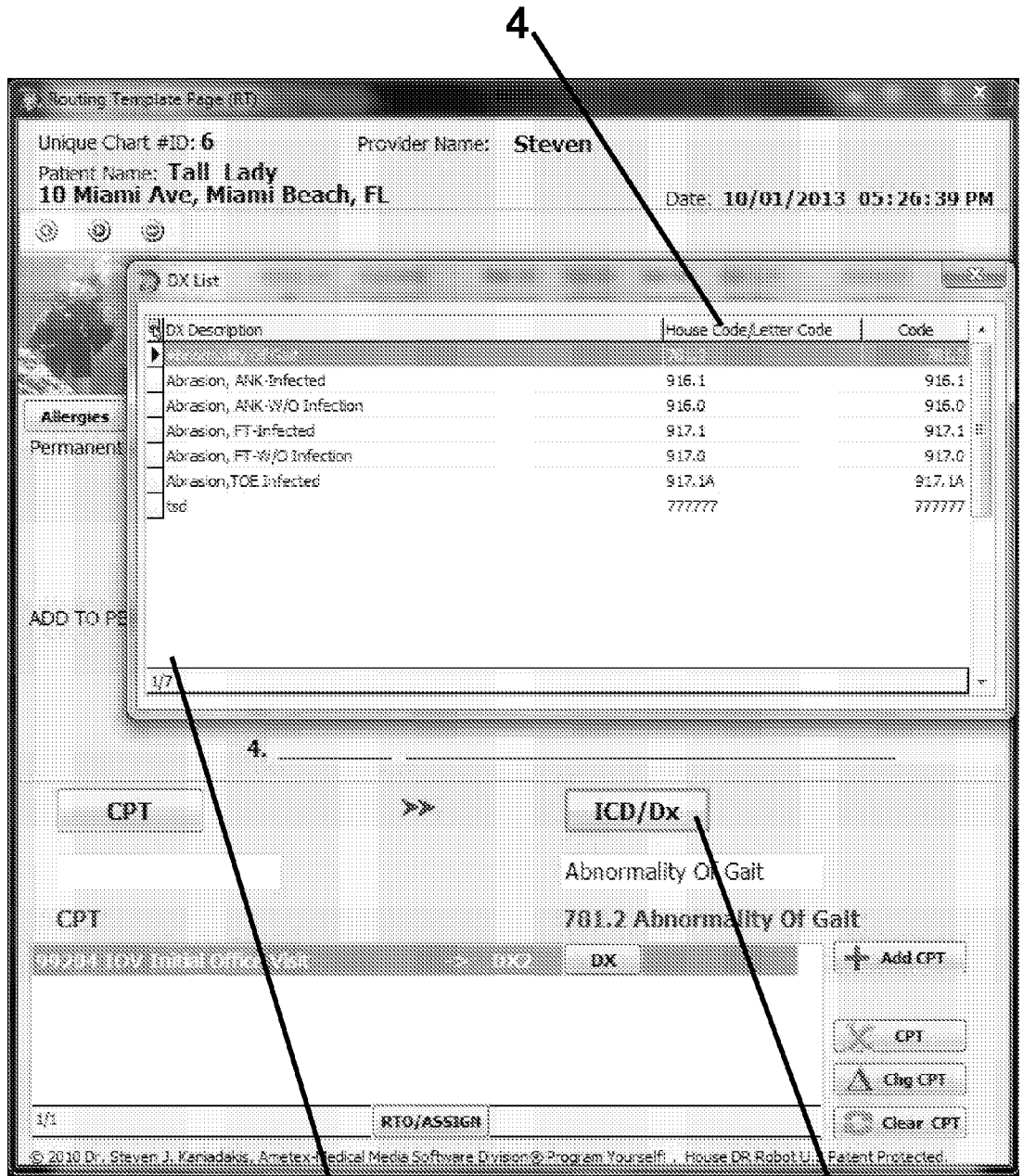
FIG. 21 displays a Routing Template (RT) page shows an insertion of any record or image with (IMG) command graphic FIG. 20. Also, reading ICD diagnosis 3 database and house code invoked by corresponding command graphic text 10. Contrast FIG. 20 CPT.
Figure 30:
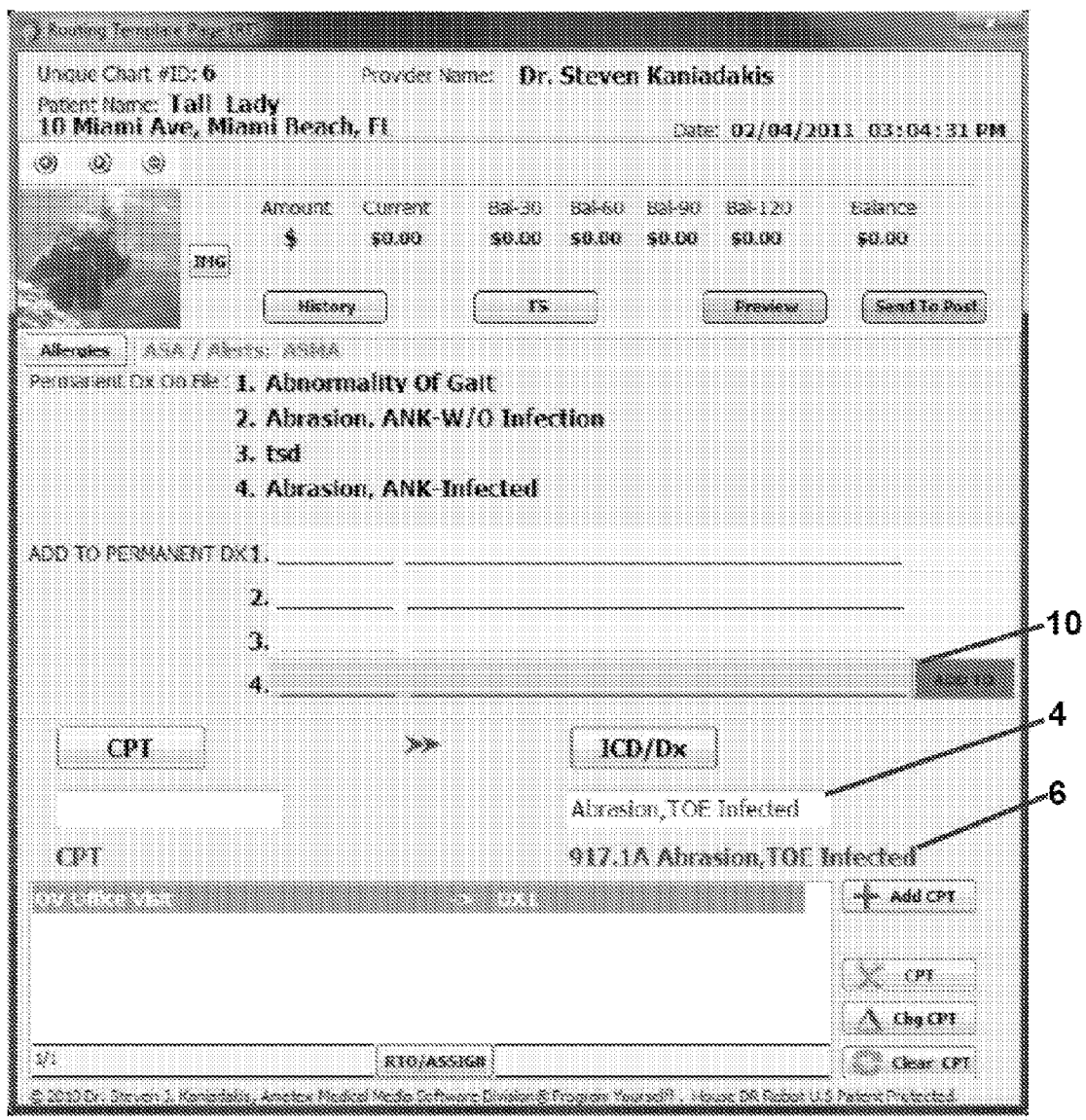
FIG. 30 displays diagnosis information 4, 6, 10, is entered as mentioned for CPT. See FIGS. 20/28 for CPT, and add to the fields, as related in FIG. 29. ICD (diagnosis Dx data) as with CPT data bases can be populated from external or third party programs, customizable. A remove option is likewise on Add To 10 field, see FIG. 31.

This invention's Routing Template page of information is described from superior aspect to its opposing end. This Routing Template is organized in a unique and purposeful way. In any case this invention includes a Routing Template that essentially consists of Provider's Name, demographic data, identification and/or profile, actual Time/Date lapsing action 11 docket (representing actual Date Of Service-DOS), Patient's Name, profile demographics, Patient's Images "IMG" (clinical, face, condition view), corresponding image "IMG" controls, Account data, a History review, Touch Screen "TS" option and expansion FIG. 16 10, patient's Preview (printable preview and history thumbnail history generated FIG. 32 on next page from Routing Template results), Send To Post (STP), "Allergies/Alerts", a Permanent Diagnosis (Dx) On File history field, a field or section to "ADD TO" aforementioned Permanent Dx On File section in record, "CPT" and "ICD" windows or sections represented by invoking respectively each command graphic 10 each acting as described textual buttons to view C.P.T and or H.C.P.C. and I.C.D related data, "CPT" and "ICD" field said programmatic mnemonic texting and the programmed texting aspect 6 or interactive field acting as predictive text field(s) 6. FIG. 28 and FIG. 39. Also, referred to the programmatic mnemonic texting box represented by anticipating entered data into each of the fields or box(es) which will automatically start displaying the data called from database information, in each field box, respectively as "CPT" and "ICD" (Diagnosis or "Dx")* and the data displays in areas subjacent to these aforementioned fields. FIG. 30. This aspect of programmed texting is anticipating the next letter, descriptor, character, number, word including anticipating the medical code sequence series and description stored in the memory or stored in said subsequent database table location, and extracting the client's data in the database. This data displays 6 selected therefrom each of the results entered by user into programmatic fields acting as predictive boxes. This allows the user a final conformation before invoking an action to display each data entry into each display (as described below). FIG. 10 is an embodiment shows CPT [database] invoked from the embodiment having corresponding code descriptions, code numbers and code letters, 4. FIG. 10 shows novelty of converting code numbers into code letters and vise-a-versa 4. Compare to and FIG. 20. Distinguishing from FIG. 21 reading ICD diagnosis 3 database and house code invoked by corresponding text on interactive command graphic. Dx is shorthand designation for diagnosis ICD. 10 Database also corresponds to said programmatic mnemonic texting aspect acting as predictive text value box on Routing Template screen, FIGS. 28, 39 and FIG. 30 for ICD database reading and extracting respective output and input data.

Figure 29:
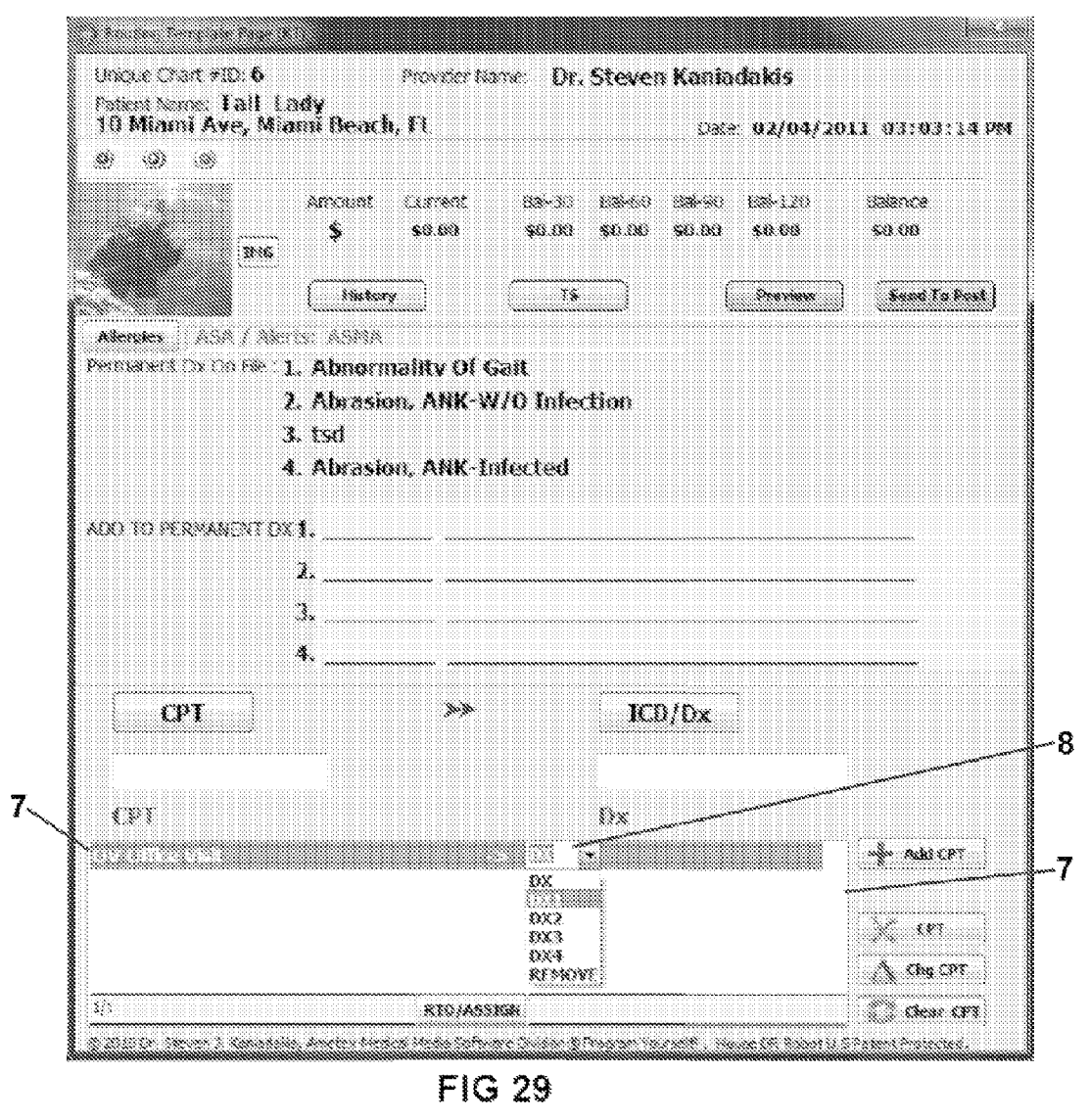

As it was mentioned above CPT and ICD results selected from respective touching command graphics 10 acting as interactive buttons in respective database windows displays in the same subjacent location, once again in order for user affirmation of selection. Next, CPT and ICD data selections obtained from each respective database displays in another field at an area about the distal one-third of said Routing Template in a housing field 7 hereafter called a housing thereof "CPT/Dx field". FIGS. 9A and 9B-C, FIG. 29, FIG. 31, FIG. 33. Wherein, aforementioned housing field will become a method of assembling to organize and a housing field to display CPT and ICD data point set selections from aforementioned CPT and ICD command graphics 10 acting as buttons and programmatic mnemonic texting aspect 6 acting as predictive fields and boxes. When CPT and or H.C.P.C. data is affirmed in the above mentioned displayed area then the CPT and or H.C.P.C. is transferred to collect in a highly sophisticated method, organized fashion, and using the Programmatic 6 method more fully described below. When the user selects an "Add (+) CPT" button command graphic adjacent to aforementioned 7 CPT/Dx housing field (as described below). When data appears in "ADD TO Permanent Dx" and/or "Permanente Dx On File", the said "CPT/Dx" field displays a means for user to make selections of ICD (or "Dx) diagnosis data from results displayed in "Permanente Dx On File" and "ADD TO Permanente Dx" fields. This invention's "ADD TO Permanente Dx" field has a "Remove" (red) and "ADD" (typically as a green color) command graphic FIG. 30 acting as a button or switch, wherein user can change data in this field at particular ascending field typically given as line numbers in these aforesaid field, and repeat steps to for data entry as mentioned above to display with each action. This invention's aforementioned housing "CPT/Dx field" 7 has a means for user to select a "Dx" that corresponds to particular line numbers in "Permanente Dx On File" diagnosis data point set and "ADD TO Permanente Dx" field diagnosis data point set. This is to co-ordinate particular "Dx" selections from ICD with CPT in the housing "CPT/Dx Field". Selection for each "Dx" is made from the "Dx side" 8 FIG. 29 of the housing thereof "CPT/Dx field" 7 with a switch or command graphic FIG. 30 acting as an interactive button image that will flash or display 10 upon a pointer controller "mouse over" (pointer, stylist, cursor, mouse over) or touching 10 adjacent Dx site 8 on "Dx side" of each CPT/Dx set. Dx are displayed 8 FIG. 30 in a horizontal 10 and sequential manner adjacent each selected CPT and or H.C.P.C. in "CPT/Dx housing field". Dx command graphic acting as a button has a vertical display invoked drop down selection box field 8 to reveal a list as, "Remove (Dx selecting one as), Dx1, Dx2, Dx3, Dx4" 8. FIG. 29 and FIG. 30.

Figure 9A:
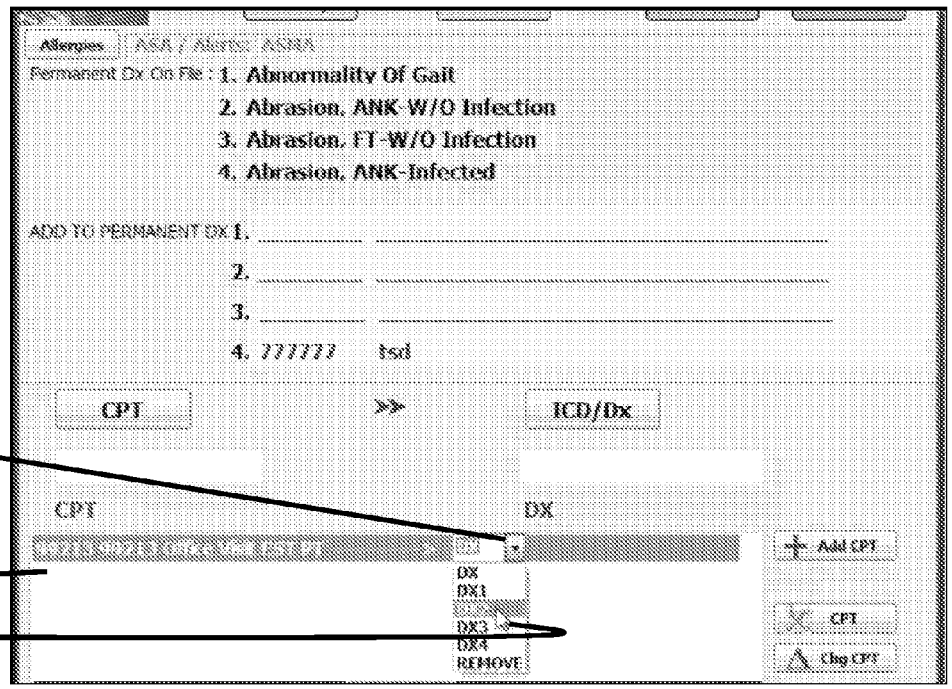
FIGS. 9A, 9B-C is first embodiment of Routing Template page screen. 9A CPT data matches up with ICD (diagnosis or Dx) data fields and housing field 7. 9B diagnosis data in CPT/Dx housing field matches with "Add To" and/or "Permanente" diagnosis fields. 9A, 9B-C diagnosis values displayed in "Permanente" field.
Figures 9B, 9C:
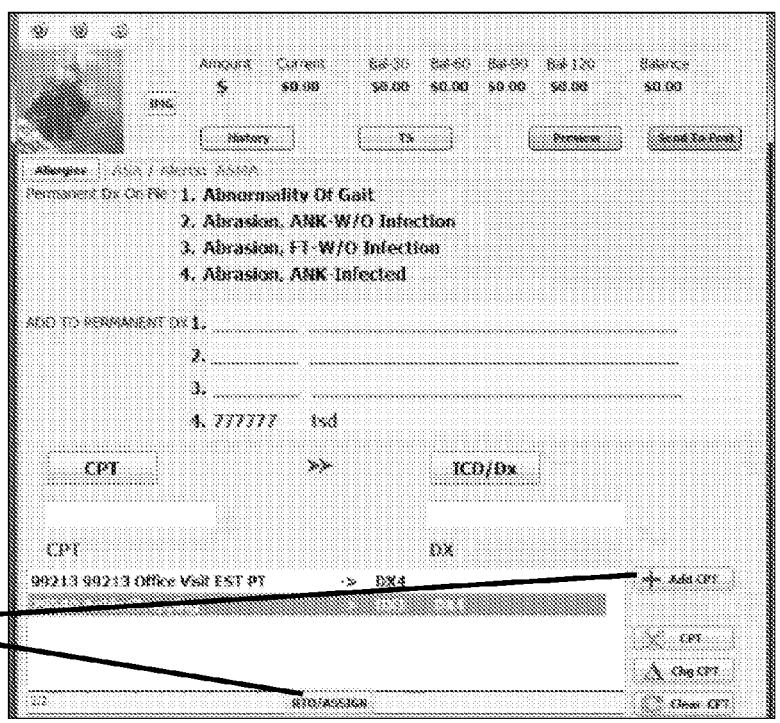
Figure 31:
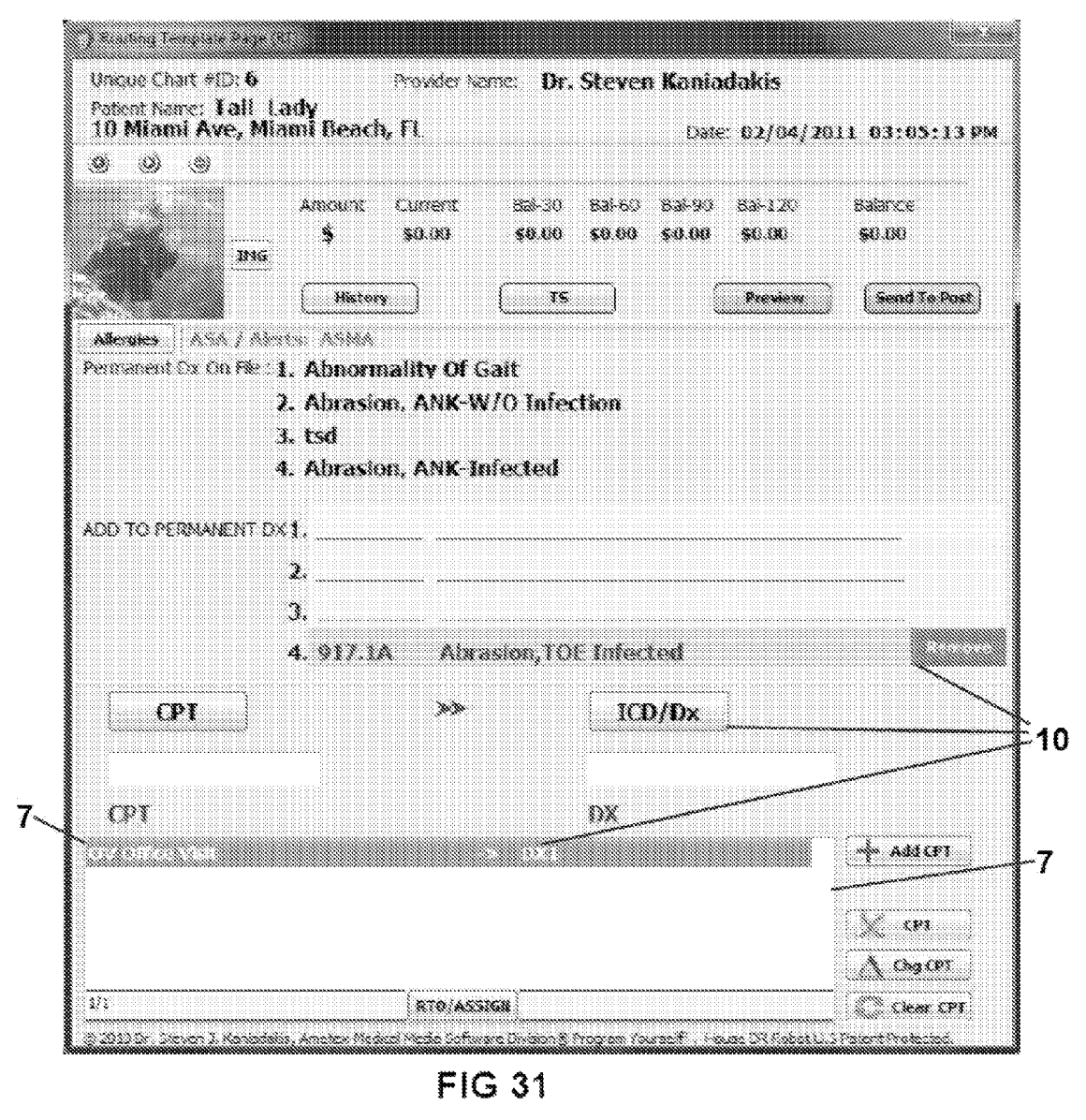

Therefore, each the particular selected CPT or HCPCs code number description corresponding to particular selection(s) of "Dx" or ICD via selecting at least one ICD diagnosis data point from said fields reported in enumerated lists of "Permanente Dx On File" or "ADD TO Perm Dx". FIG. 9A and FIG. 9B-C. Each aforesaid enumerated field correlated to entry, such as, an ascending line number "1." shall display an ICD code number and description represented by "Dx1" 8 in the drop down selection command graphic FIG. 30 on each the subjacent "Dx side" 8 of "CPT/Dx housing field" 7. This invention's mechanism allows a highly sophisticated means to remove and replace ICD from the "ADD TO Permanente Dx" field to replace line number "1." (any ascending or descending field) therefrom "Permanente Dx On File". FIG. 9B-9C. This application will allow the in the "Permanente Dx On File" spaces to report upon application viewed (and reviewed) at next visit. There are mechanisms in this invention's design to report a more recent "Dx" (i.e., ICD filled in on "ADD TO" field) to become accurately placed in order to correspond to the respective selected CPT and or H.C.P.C. This is reported in progression in a "CPT/Dx housing field" as mentioned herein forming data point sets populating said housing for a given named account. Adjacent to "CPT/Dx housing field" 7 are interactive command graphics controls that essentially used to Add (plus+symbol), to Remove ("X" symbol), to Change (delta or Δ symbol), or to Clear (double arrow) "CPT/Dx field" 7 particular selections. These allow user to channel data in fields, from "CPT" command graphic images acting as buttons and CPT mnemonic texting feature for acting as a predictive box field on the "CPT side" of this art's CPT/Dx aspect, space or field 7 described. When user presses described "Clear CPT" command graphic switch then the entire CPT/Dx field 7 typically becomes another action to "Remove Dx", since all CPT and Dx data sets become removed or "cleared" from this CPT/Dx 7 housing field space. Therefore, the set or CPT Line Number item is removed. Whereas, "ADD TO" field, as mentioned above, can be invoked as separate action to "Remove" (typically as a red command graphic pop-up) particular ICD selection(s). FIG. 31. Functions of ways that these channel data related to these respective command graphics adjacent to a "CPT/Dx housing field" are evident by command graphic text and respective said command graphic symbols used to be graphics of actions switches or command graphics acting as buttons perform. FIGS. 9A, and 9B-C is an embodiment of Routing Template page screen. FIG. 9A CPT and or H.C.P.C. data matches up with ICD (diagnosis or Dx) data fields and housing field 7. A specific sequential order for diagnosis listed, listing first (important) position, second, third, etc. (primary, secondary, tertiary, quaternary, etc.) and each diagnosis is corresponding to a particular CPT and or H.C.P.C. FIG. 9B-9C diagnosis data in CPT/Dx field housing matches with "Add To" and/or "Permanente" diagnosis fields. FIG. 9B-9C diagnosis values displayed in "Permanente" field from previous entry, and diagnosis data may be removed from and added to Permanente field.

Expressions such as ICD and Dx are described in an interchangeable way periodically in descriptions herein. These designations both refer to diagnosis, as it is well known in professional communications and people of ordinary skill in the art.

Each entry in a CPT/Dx field for housing the medical related data is typically referred to as a CPT and or H.C.P.C. Line Number. Although at this location of the interface any such other designation for position and identification of the data entry can be used without posing limitations on the art. This line number reference for a purpose of description thereof each position of each respective CPT or H.C.P.C. data point and each the data point set is corresponding to each diagnosis selection, and the user client is further forming a data point set by way of including the ICD diagnosis data point and data point set. And each CPT or H.C.P.C. Line Number will become affected by aforesaid adjacent command graphic switches to channel data entry. Although logic essentially dictates items as "line numbers" in CPT/Dx field, there are not actually enumerated as with other described fields. Hence, this art may make reference to "line number" in CPT/Dx field. ICD or "Dx" representations are made in invention's "CPT/Dx" housing area on Routing Template page or screen. CPT and or H.C.P.C. code number(s) and/or code description(s) become followed by diagnosis or "Dx" representations.

Therefore, the general flow may be described as selecting CPT services from database field(s) described above. The CPT and or H.C.P.C. is gathered by (invisible) line numbers on the "CPT side" of a "CPT/Dx housing field". The user can next select "Dx" number from a sequential lists called, "Permanente Dx On File" and/or from "ADD TO Permanente Dx", and/or select additional ICD from database field(s) described above. Alternatively, the user can select a CPT and or H.C.P.C. then a Dx, and this data is formatted essentially by line number or item as a data set displayed in a CPT/Dx housing field. In either approach mentioned above, the user must select at least one CPT or one H.C.P.C. and one Dx for each CPT/Dx line number. A selection method FIG. 29 on the "Dx side" thereof a "CPT/Dx field" housing part 7 which allows user to readily choose ICD or Dx from existing records and medium. A feature that makes this application superior is for the client user to see last several Dx at a glance, and with finger-tip-control access a drop down 8 selection field box and touch the diagnosis to display each in order and in conjunction to a given CPT or H.C.P.C. Application has many safe guards and cross-checks given by message alerts. Alert messages make this invention safer to prepare patient records more specifically described later. This application offers alerts to identify some common pitfalls in coding, such as duplicate or double entered data when particular events are generally unacceptable practice to submit in virtually every instance. More is described about this invention's designs later. The so-called "red flags" as purported established by Federal case law is not actually existing as providers might think exist to help providers in this communication.

This lack of flags or alerts can cause providers grief, costly, life changing vital errors. Thus, some of these most obvious and agreed upon alerts have been in programmed accordingly. Balanced carefully so as to respect imposing limitations upon professional practice judgment and what might be regarded as merely differences in practices.

Figure 45:
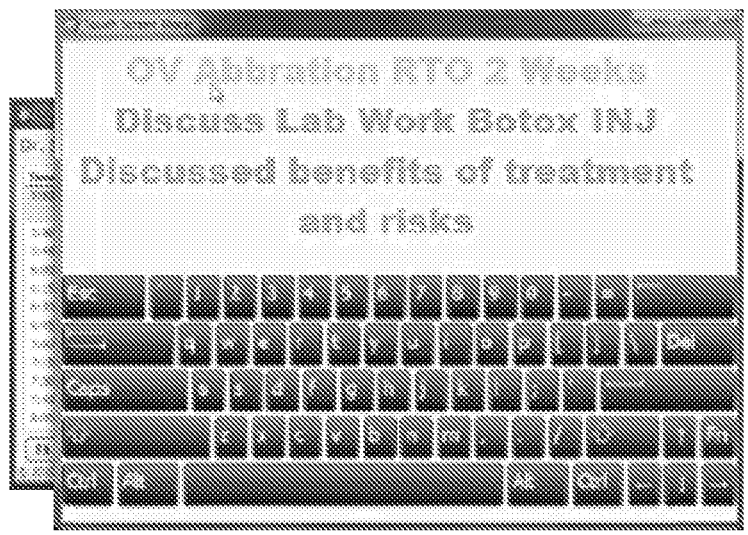
Figure 46:
Figure 47:
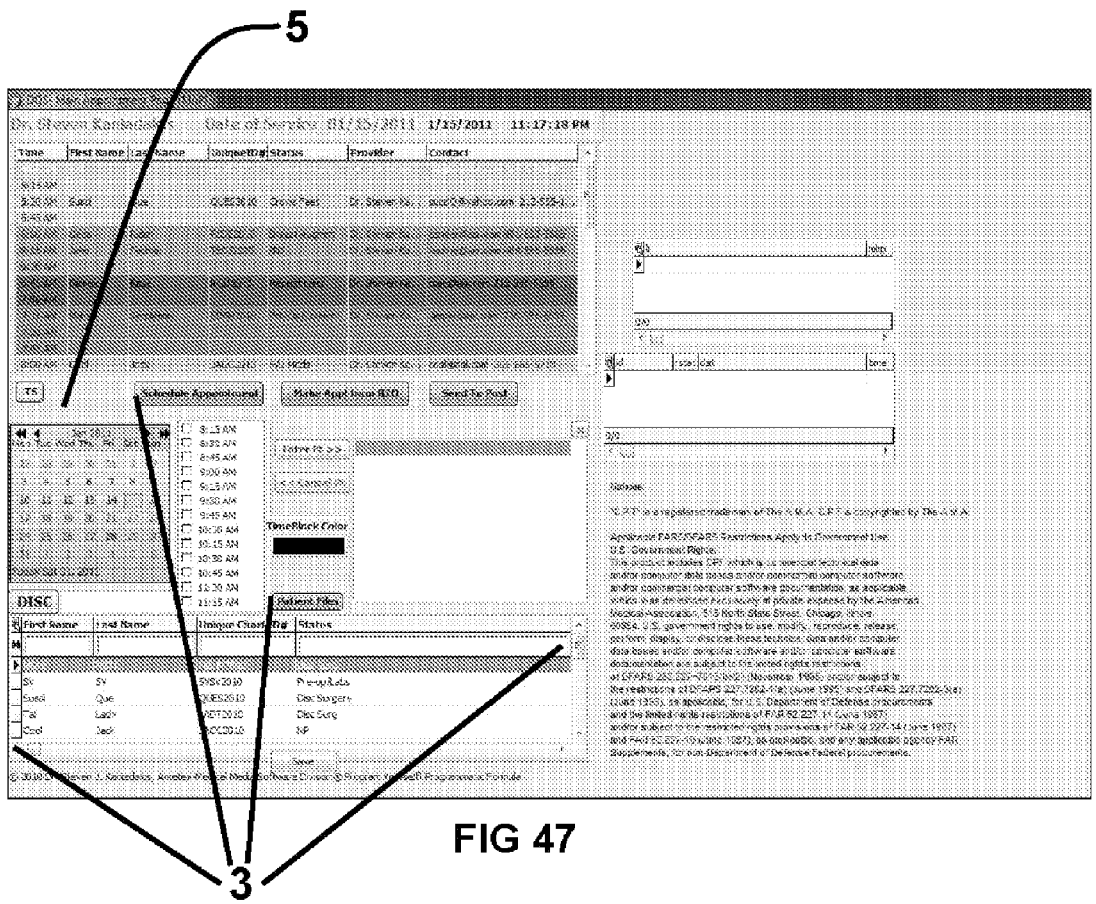
FIG. 47 shows adjacent main appointment page a comparison and contrast with FIG. 5. This part of the embodiment can be configured to show a logo graphic, links and a company name. Command graphics invoke corresponding database fields 3, here expanding lower part patient appointment page and synchronized patient database.

The aforesaid mentioned "Allergy/Alert" command graphic switch or button is employed to switch, to add and to remove, this data as necessitated for each patient's account, current and past history. This information or data becomes displayed near the superior one-third of this invention's Routing Template part page or screen. Certain data or medical information displays as a template or guideline for any end users later supplement, amend, or replace any/all general medical terminology presented initially with this application. For instance, a user may change, add or delete particular "Allergy/Alert" database installed for this invention's customizable template like model. Likewise, this invention's model contains template data virtually all other database, C.P.T, I.C.D, H.C.P.C.S, C.M.S and other database may become installed hereto invention's art and become unique to end user's professional community or end user's intended purpose for use of this application as an instrument. In short, this invention's design therefore, allows compatibility in these ways as well. A portability with respect to invention's template nature and portability with reference to application being utilized as a device, such as therewith Apple®, iPhone®, iPAD®, Windows® or Microsoft® (MS) or any others, and so as to not become limiting factors to use of this inventive characteristics therewith other mobile devices, operating systems and things. Evolution of technology should be allowed to limit compatibility of this invention's originality. Variations obviate need to make update versions and/or renditions still representative of this novelty. This invention disclaims use of such other devices and/or programs when not combined with this invention's art. The afore said fields are implemented in fields that can become reduced to hardcopy forms, "fill-in-the-blank", fields that are on typical computerized keyboards, touch screen technology or "write-to-text" pad fields. FIGS. 45 and 46. Whereas, technology such as "write-to-text" technology is a disclaimer as to this particular creation, the combination of this invention together with such other technology is included in this invention.

CPT and or H.C.P.C. programmatic mnemonic texting aspect text 6 value box and CPT interactive command graphic text responding like a button allow this invention's superior art to enter typically a unique and relatively simple three or four letter proprietary code letters or code designations thereby invention's design to allow complicated or long CPT and or H.C.P.C. code abstract code numbers to become essentially preempted. Although, this invention allows the user to enter two-letter code as, "OV", for example, each the CPT fields will display appropriate and traditional C.P.T. and or H.C.P.C. code number FIG. 28 parts 4 6 versus FIG. 39. FIG. 39 is an embodiment of Routing Template page.

Figure 35B:
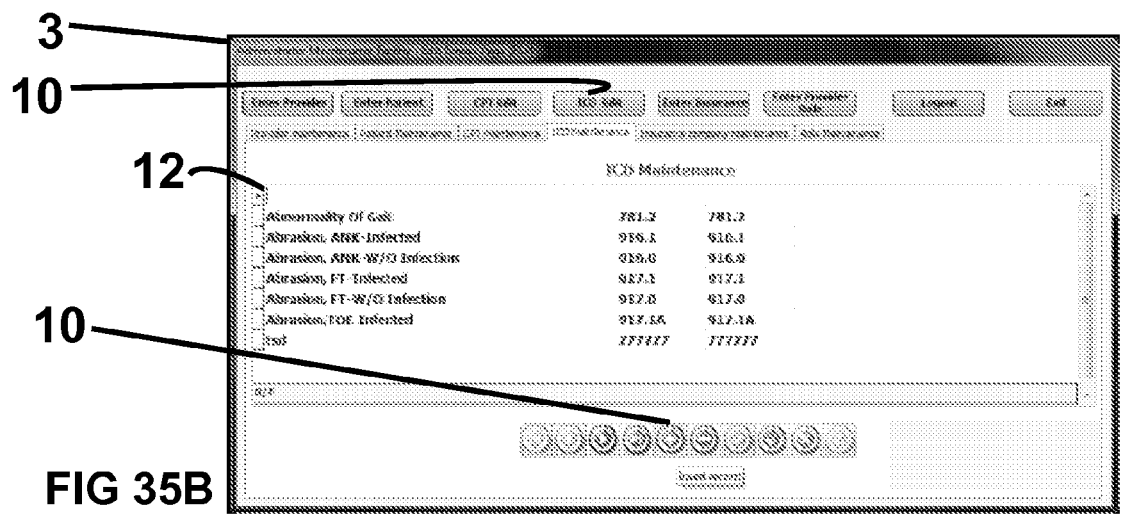

Programmed texting acting by way of each the predictive text box fields shown using code numbers with results of programmatic mnemonic texting field appearing immediately inferior to box or field for CPT and or H.C.P.C. data values. The command controller, cursor, or arrow pointer 12 is shows fashioning code and the Programmatic texting aspect. FIGS. 28 and 39, 4. FIGS. 35A and 35B. See FIG. 10, part 4/FIG. 28, CPT codes. Previous embodiment in FIGS. 50/51. CPT fields work like diagnosis fields in FIGS. 30/31. Refer to FIGS. 48 and 49. FIGS. 12 through 47 help elaborate upon this simple model demonstrated and described and with a detailed embodiment in FIGS. 1, 2 3 and 4. Wherein Figures in FIGS. 12 through 47 are some screen views. Figures illustrate displayed data of CPT code number descriptions and code letters 4 from various fields accessing the client user's in house customized code using "OV" and as each code subsequently appears in 7 the CPT/Dx housing field. In an alternative, this invention's design will also allow there to be displayed in CPT/Dx field housing each the CPT and or H.C.P.C. as the client user entered each the data points from CPT and or H.C.P.C. command graphic acting as a control and CPT programmed mnemonic texting box(es) to display C.P.T and or H.C.P.C. data in CPT/Dx housing field as in Figures in FIGS. 12 through 47. These screen shots Figures shown in FIGS. 12 through 47, thus, become illustrate ways that the C.P.T and or H.C.P.C. data points will correspond and will display for each the client users' customizable C.P.T and or H.C.P.C. data point for this invention's easier method to record medical related data information for providers of healthcare. These illustrations combine designs described above to produce results thereof data point sets as illustrated by some of these screen views from this invention's application design and utility.

The figures and drawings are displaying screen views are showing embodiment features and advantages. And the figures are showing actions of the invention's application and implementation as demonstrated together using the client's computer and computing device and related to an embodiment of this method related machine program. These and other figures and drawings have been previously filed as "Unpublished" therewith U.S. Library of Congress related documentations.

Figure 33:
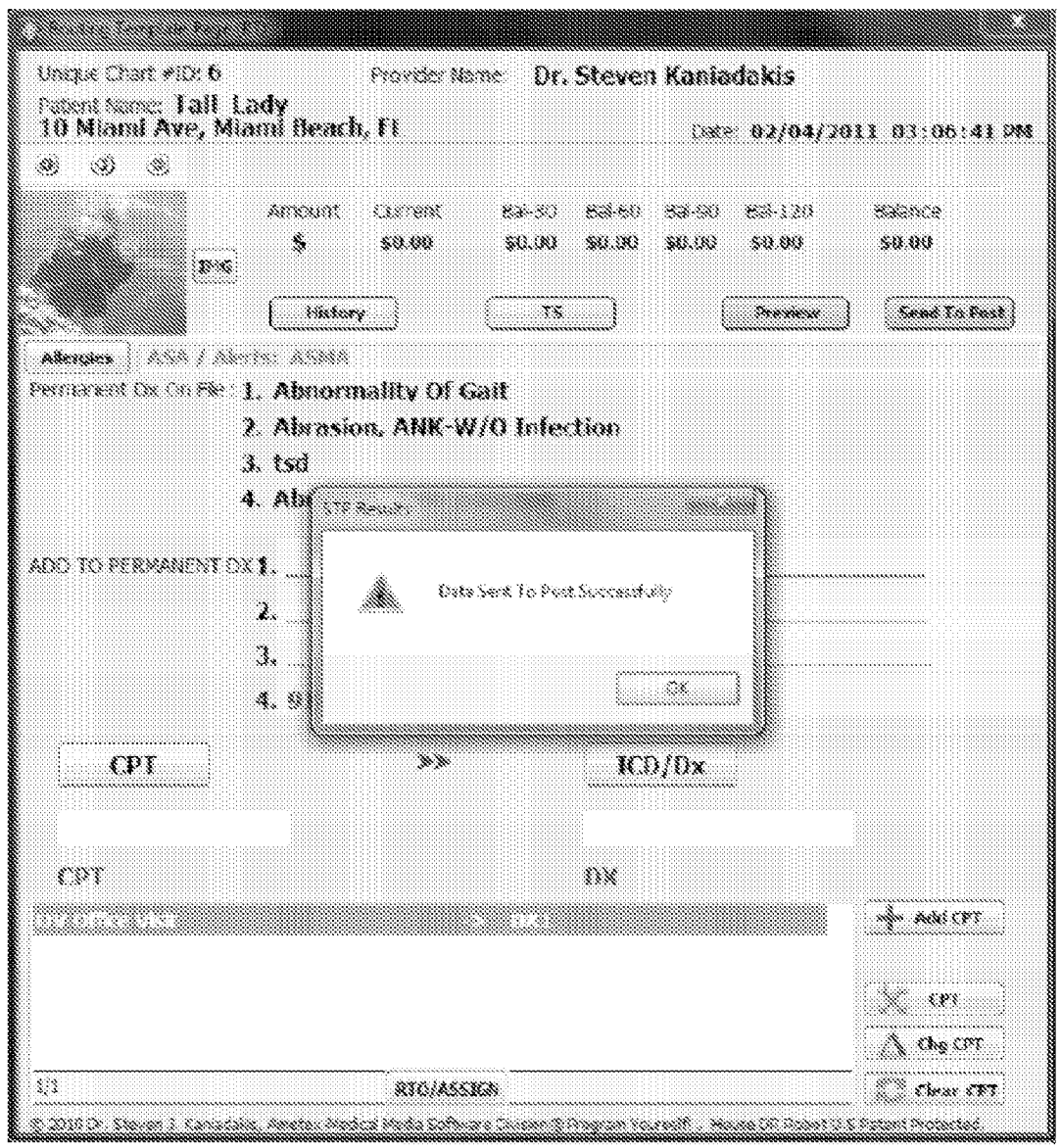
FIG. 33 displays invoking of a Send To Post (STP) command graphic sorts and send data recorded on Routing Template page.

The aforesaid Send To Post or "STP" interactive command graphic located on invention's Routing Template was distinguished from the "STP" interactive command graphic on the scheduler page 5 or main appointment page ("MAP" screen display). Data entry on Routing Template part may become stored or populated to an external program using invention's superior "Send To Post" ("STP") action. This causes data to move from the database tables of this application to populate, synchronizing and bridging, at least one external program and store in application. FIG. 33 displays invoking of a Send To Post (STP) command graphic sorts and send data recorded on Routing Template page to history, external and/or third party programs for integration or migration of data. Pop-up displays. Now ready for new or another day or patient encounter. Also, invoking the Routing Template Send To Post command graphic is causing the data to be moving from "ADD TO Permanente Dx" subsequently to display in "Permanente Dx On File" field. This data displays on the next generated Routing Template on the next encounter or date of service (DOS) at Routing Template part's said "Permanente Dx On File" field. Hence, this invention's art is to allow a quick and easy reference to data present from patient's past and last encounter, namely at least the last four diagnosis entries are posted and located at the embodiment's "Permanente Dx On File" listed at previous visit(s) or so-called on a particular Date Of Service (DOS).

Figure 25:
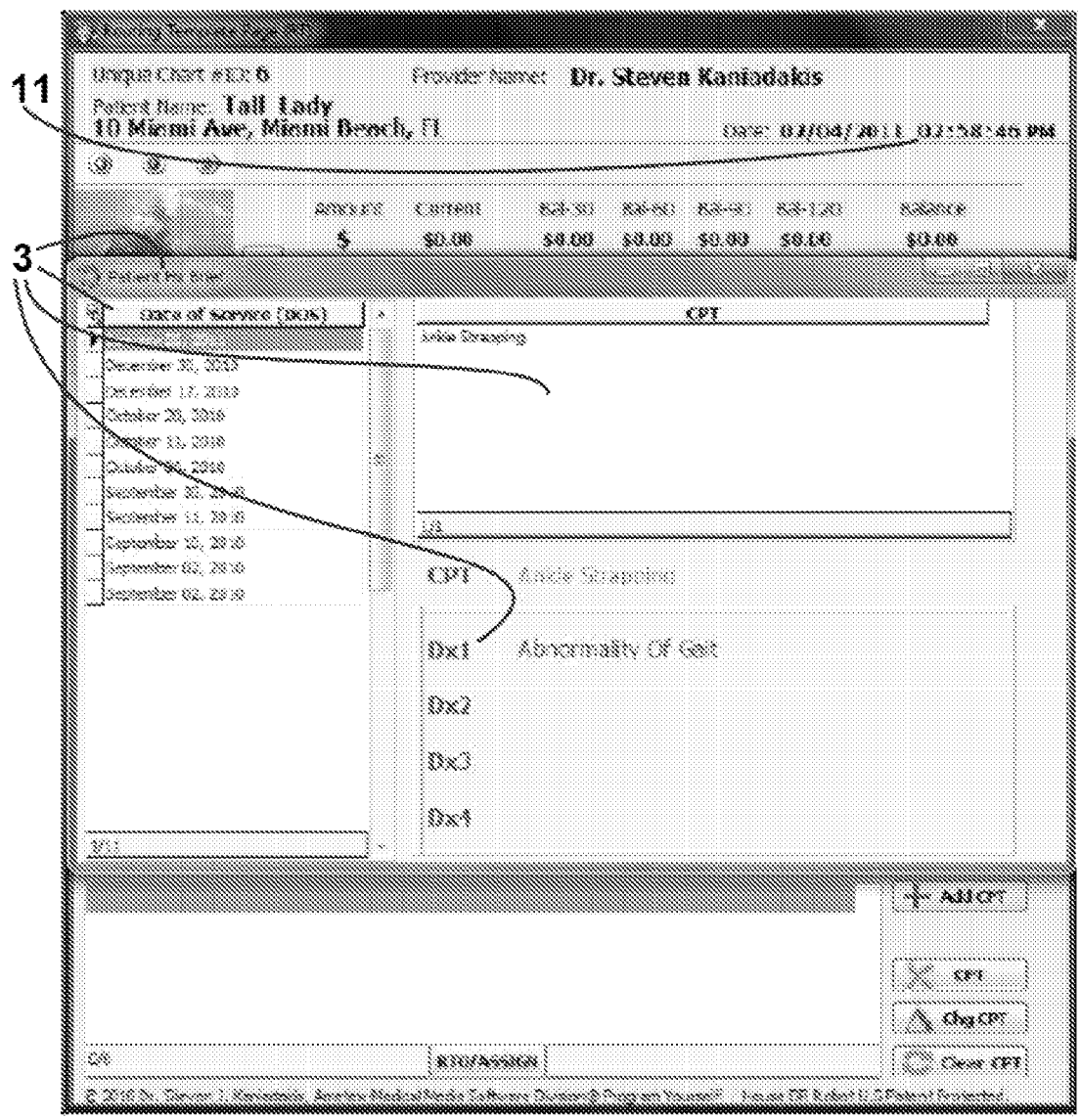
FIG. 25 displays the database 3 invoking of the Patient History (Hx) command graphic (also see FIG. 25) on Routing Template user interface page (background). Command graphic shown in FIG. 1, as one previous embodiment, in FIG. 9 and FIG. 39, as this embodiment. Action of time/date docket 11.

The aforesaid mentioned "History" interactive control command graphic shows "A Patient's Hx (History)". FIG. 25. This window or display shows recorded patient history as reported in this Routing Template. It is an archival system of this application's local database 3. However, data can become populated from external programs in ways as mentioned. Therefore, once invoked, "Permanent Dx" will virtually go "On File" in "History" (populating the client user's local database) to reflect ICD and CPT and or H.C.P.C. from reported Routing Template records stored in the memory providing the computer accessing the embodiment application or resulting therefrom the Routing Template's Sent To Post (STP) action.

Figure 44:
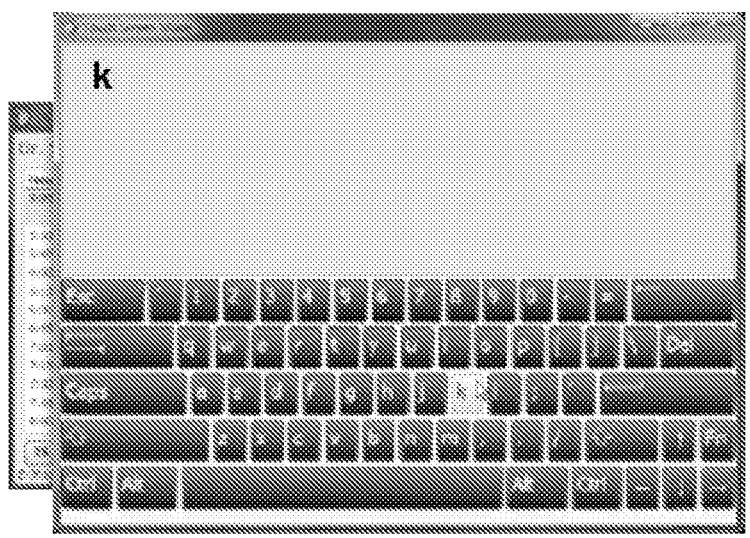
FIGS. 44, 45, 46 shows a previous touch screen mode pops up (foreground) as in FIGS. 14, 22 as with this previous component of the embodiment, FIG. 5. Contrast with FIG. 45.

The aforesaid mentioned "Touch Screen" ("TS") command graphic acting as a button opens another feature 12 anticipating texting data acting as a predictive "dictation/translation function" field, as with Discussion ("Disc" for "Status"), and for progress notes. FIGS. 44 and 45. Thus, a secondary characteristic relates to this implementation of programmed texting feature anticipating the client's text and phrase(s). A form of artificial intelligence predicts and anticipating stored in a computer's memory common (template) expressions and unique expressions that become templates for user/provider. Dictated (voice) 12, text-to-write, and entered notes (expressions) here become translatable. FIGS. 45 and 46. A drop down field allows for the client user a means for choosing results. This is like the "grammar" and "spelling check". The client user can select the rest of a word(s) and phrase(s) in a chart note, progress note, letter or file as the simple "Disc" or "Status" in a method as the programmatic mnemonic texting technique and aspect box works for creating customizable in house code letters. For example, this saves time as a healthcare provider's practice typically will repeat the same dictated expressions for treatments plan(s), procedures and other expressions used in provider's practice documentation. This aspect spares the need to repeat typical words and phrases that the provider will use in practice and documentation. This Programmed mnemonic text becomes essentially a database based upon stored past dates and entered phrases. Including typically dictated prescription doses, return dates, post-operative instructions, op notes (procedures) and other documents. This becomes a significant manner to have confluence and continuity of care.

The aforesaid mentioned "Image" ("IMG") button allows a superior advantage to healthcare providers practice. It has become a typical record to document and to affirm that patient's identity is the same as shown on medical membership cards and things. This is primarily for business office staff. Routing Template on this application displays Images of the particular patient profile, and this offers a distinct advantage to paperless movements. More specifically, such a design allows clinical staff to recognize the particular patient's identity when about to render treatment or evaluation. Thus, this becomes a reinforcement safety cross check and another quick reference at fingertip control of the end user. (To be sure it is the right patient among other things.) IMG button allows, in effect, to "Toggle" command graphic action to switch views or images of a patient's condition to become displayed, radiographs scans, and virtually any other image of file to become summated here in this Image field. It is on all one page as pertinent records are becoming created about patient's encounter or visit. A safety device prevents material from sending electronically. When invoking aforesaid "Send To Post" command graphic function, for example, this record is hidden from others. Hence, an addition means for help communicate information and records from business staff to clinical staff and vise-a-versa as described in particular with regards to very important other records, CPT, H.C.P.C.S and ICD/Dx correlated organized records and medium as performed by this superior application template model.

The aforesaid mentioned "Preview" interactive command graphic acting shows a summarized rendition of information intended to become stored in each the clients' memory providing the computer and accessing a database or Sent To Post. FIG. 4. A "Preview" is allowed only when properly and completed fields are performed in application. Therefore, this is acting as another safety mechanism about this application design, to help prevent incompleteness of records. For example, an event may become alert when a CPT and or H.C.P.C. is not properly matched to an ICD or "Dx" as described in a method above. The "Preview" FIGS. 4 and 32 will also display the rendition therefrom invoking a "Preview" interactive command graphic on the Routing Template and showing Return To Office (RTO) data from tabulated screen (assignments, fee schedule, next visits, surgery date, discussions or next "status" for patient's return) FIG. 4 and FIG. 32 entries stored to sort and filter data as a data bridge for confluence, synchronizing and populating fields of data in respective data tables in this application.

Figure 32:
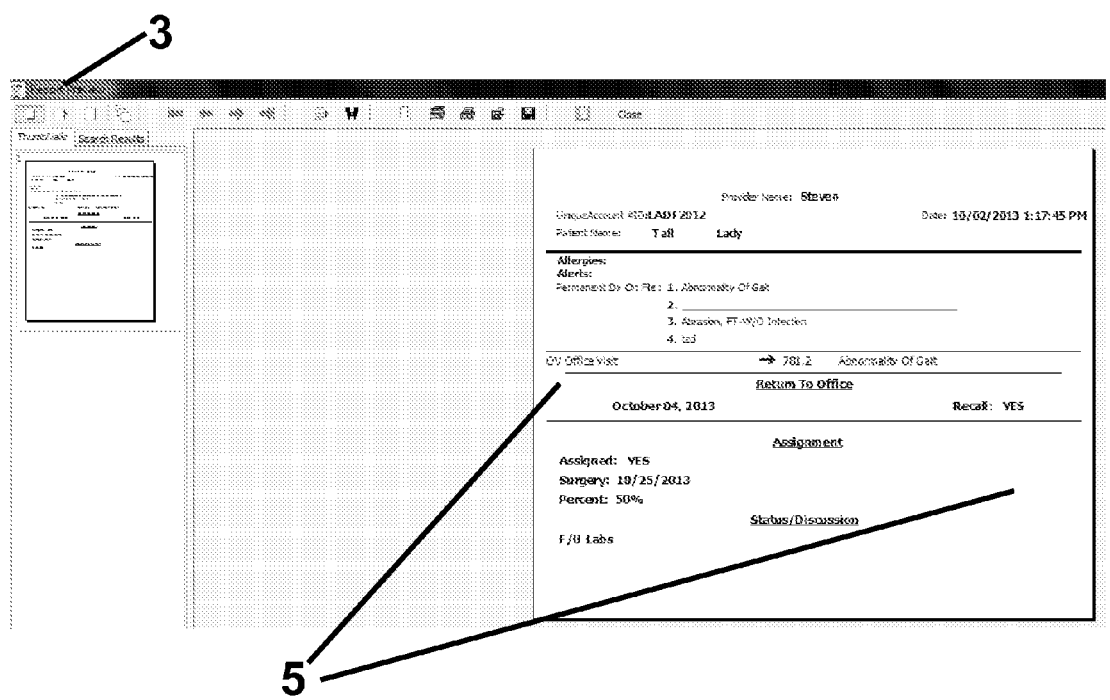
FIG. 32 displays an invoking of a Preview command graphic on Routing Template (RT) screen.

However, Preview is essentially for preview prior to the user invoking the said Send To Post (STP) action located on embodiment of Routing Template display screen. Application sorts these records to be handled separately for intended purposes. Generally, it not acceptable to send balance and fee related records coupled to medical related records. Also, superior invention's design is to sort out reappointment ("RE-APPT") dates 5 to become better equipped for external compatibility and end user's options to run a separated program for co-ordination of patients' appointments. The aforesaid mentioned Return To Office (RTO) 5 related command graphic tabs described are explained with more particularity later. "Preview" essentially freezes time docket 11 reported 11 FIG. 4 and FIG. 32 from lapsing time docket on Routing Template 11 FIG. 16. This is a unique characteristic of this invention. Time docket 10 may become enlisted documentation in order to establish some time record of patient encounter. Although, there is a stored version 3 and a "Sent" version of Routing Template, and the user must consciously choose to utilize this feature for this to be valuable. In certain cases needed this may become vital records. FIG. 4. A sample of "Preview" screen view from invoking "Preview" on FIG. 1. FIG. 32 displays an invoking of a Preview command graphic on Routing Template (RT) screen displays RT information, before send to post is invoked on RT. Displays "Add To" diagnosis moved into permanent fields as appears when posted. Captures date and time to document inventor's inventive "face-to-face encounter counter", if needed to account for time spent (see FIGS. 39, 16 and 4 time docket part, 11) when actually posted by provider FIG. 32.

Figure 26:
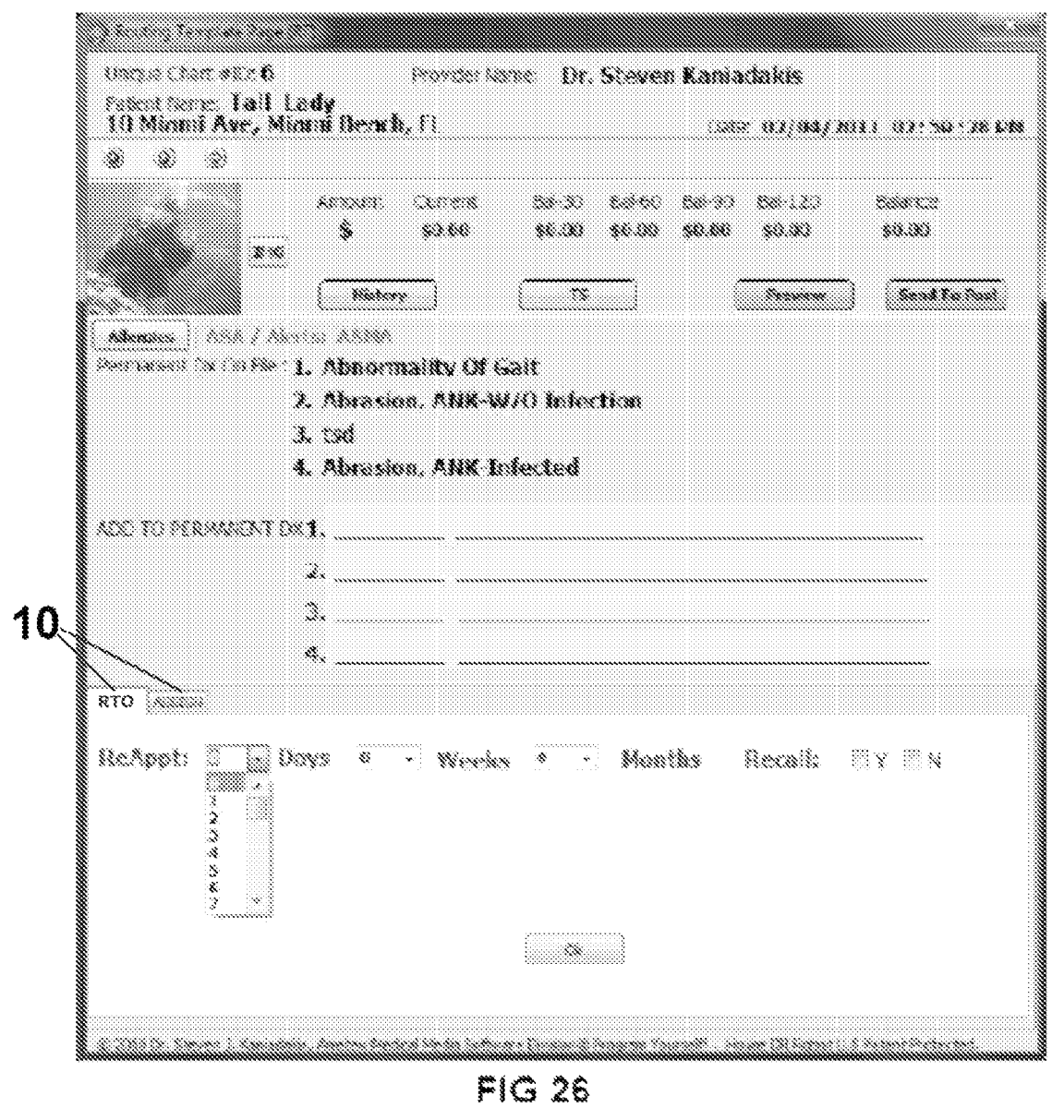
Figure 27:
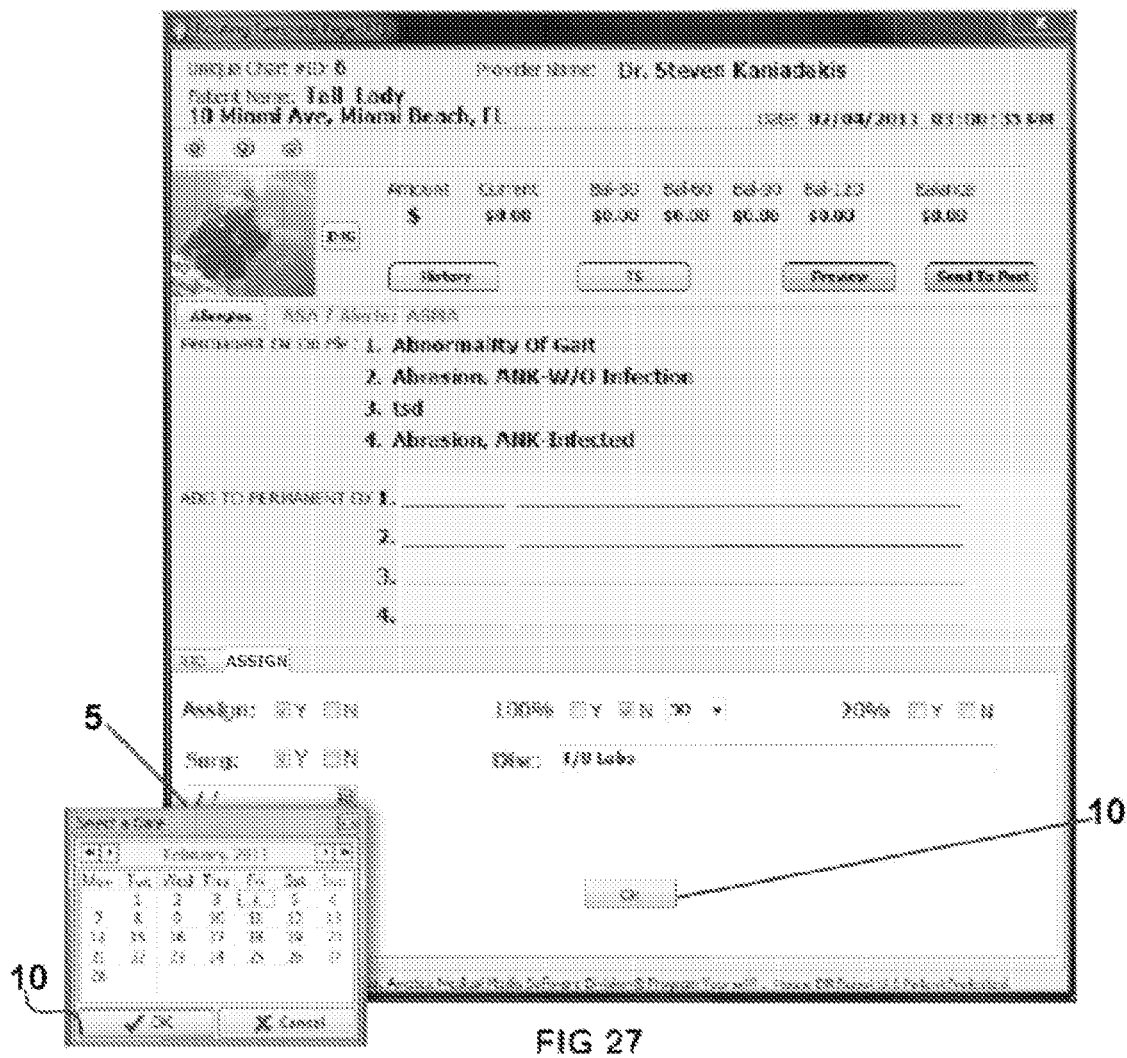
FIG. 27 displays the other command graphic tab from FIG. 26. Discussion field allows patient status to report to appointment book related fields. See status field on FIG. 2. Dates sorted and sent as related in FIG. 26.

Finally, Routing Template near opposing end from its caption is a command graphic text named as, "RTO". "Return To Office (RTO)" switch expands or opens a screen with command graphic tabs to select information about patients' plans and return visit or "re-appointment (REAPPT command graphic text tab). FIG. 26 and FIG. 27. Assignment ("ASSGN") command graphic text tab of RTO related to payments, fees, and assignment of benefits or deferred for from business office to determine. RTO essentially relates to information about patient's departure and anticipated plans for patient's scheduled return to clinical or facility. "OK" causes this data to become stored, and as mentioned above, "Preview" on printable separate screen 9 as well. Therefore, at this aspect of Routing Template there is synchronizing and confluent in a connection to, but not necessarily connected to, a patient scheduling or appointment book program 5 part of this invention FIGS. 11C, D, E, F and FIGS. 35, 36 and 37. It is pointed out in this way, since engaging each the "STP" interactive command graphic functions from application embodiment of the Routing Template and application embodiment of the Scheduler 5 component part are independent movements in practice.

This medical record, as well as other described, will reappear for the next encounter or for each the newly generated Routing Template page. A method for generating another Routing Template may be achieved directly from this invention's scheduling part 5. The Main Appointment Page 5 part of this application is a means to essentially invoke an action to generate a Routing Template page. However, as mentioned previously, this invention's schedule part 5 may become separate from Routing Template. A separate utility or process may indeed become used from external program's schedule program. The aforementioned "Send To Post" which is located on Routing Template page will process by this method and via the computing system processors and memory separate from invention's schedule related data. (Reference will be made to another "Send To Post interactive command graphic pressed/touched from invention's location on a "Main Scheduling Page (MAP)" 5. These actions should be distinguished, in that, these essentially act independently. The sorting and handling of data in this manner is another aspect of this invention's superior art and more specifically described herein. In short, this method of sorting and handling, populating, synchronizing and bridging of the data and data tables, respectively allows for a greater confluence and compatibility design.

At present the inventor believes that this embodiment operates most efficiently, however the other embodiments are also satisfactory. Even though the inventor's disclosure of a dot net framework enables scripting and greater access across computing platforms and operating systems, and the application thereof including internet browser tools, which may be downloadable or simply accessed by the client and running the parts of the application in a temporary directory such as a so called web based application. The inventor feels that scripting language is presently his practical application of the scheduler related parts, and C plus (plus) is a powerful computing language, however the other embodiment has other substantial applications. The fact is that most the people skilled in the healthcare part of the art currently accessing Windows related computing systems. Accordingly, Windows operating system is driving the machine preferred and the most practical one when it comes down to business in most healthcare processing of the material relevant to this part of healthcare related to this invention. The inventor recognizes the various applications of the invention and the variations in the market including healthcare people. Therefore, the inventor is using scripting to access internet browsers and enabling the invention to working in both parts, across platforms and versions or variations in operating systems and the computing devices thereof. The healthcare client's or user patients, by contrast, show greater variations in computing devices. Therefore, the inventor created an advantage accommodating general consumer need to having the advantage of a combination of computer frameworks and languages by way of scripting. The method of the embodiment is less dependent on, even irrelevant to, the technicalities of the known types of computer code implemented to practice the art. Rather, the method is involving a readable medical related code or language for medical related data. Therefore, creating a distinguished relevance of the computer type code from the medical related type code and use by healthcare providers versus access to their patients in this communication. The relatively more practical method is an embodiment enabling the application to operate with local database access, downloadable, or remotely accessing the client's data and client user's data as when the calendar implementation on a server is shared or used independently by or as a standalone application by each user. In short, healthcare medical related data must be able to communicate in compatible methods to others skilled in the art and to their patients. This embodiment including the calendar related implementation one of the more practical instances of this advantage of communication. See flow chart references.

Other Embodiment

Figure 50:
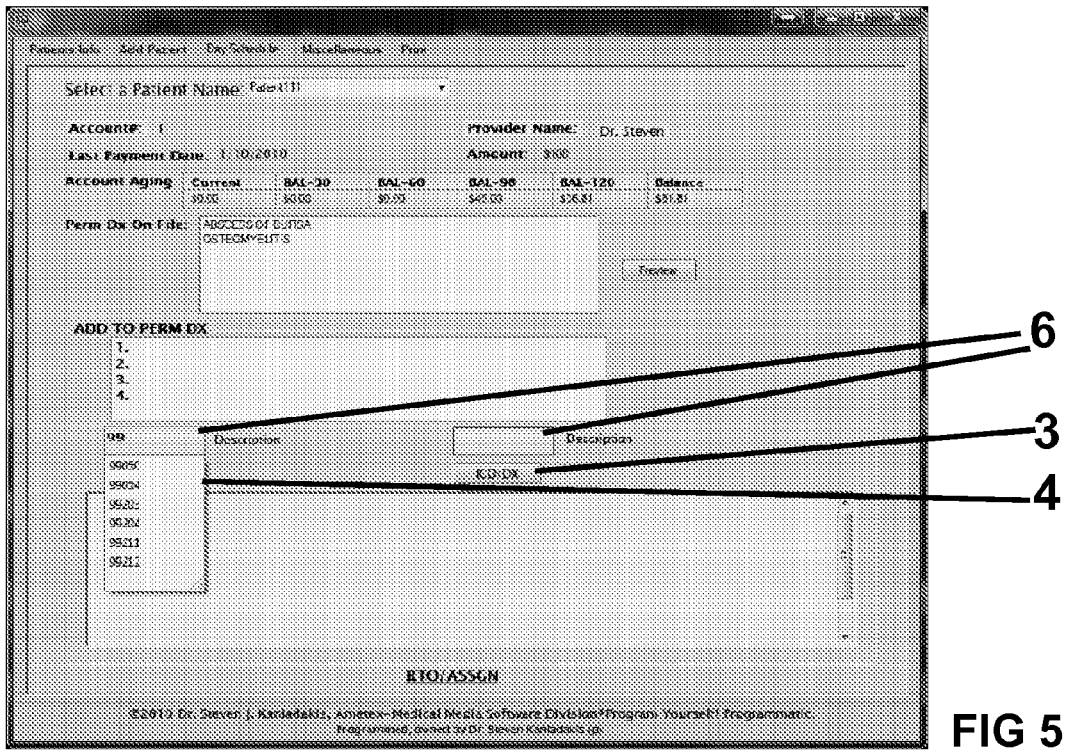
FIG. 50 shows a simple demo/model. Screen view. History of earlier implements and designs in development. Comparable to this embodiment. Another or previous embodiment, adding parts.
Figure 51:
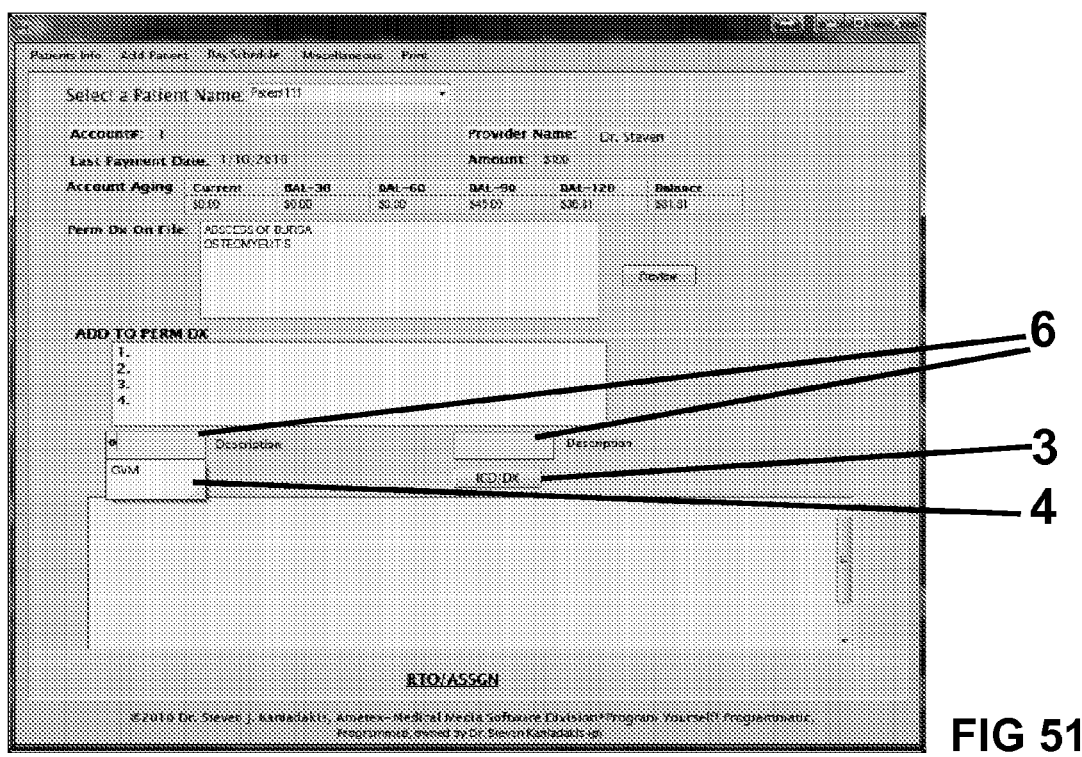
FIG. 51 shows a simple demo/model. Screen view. History of earlier implements and designs in development. Comparable to this embodiment. Another or previous embodiment, with added parts.
Figure 52:
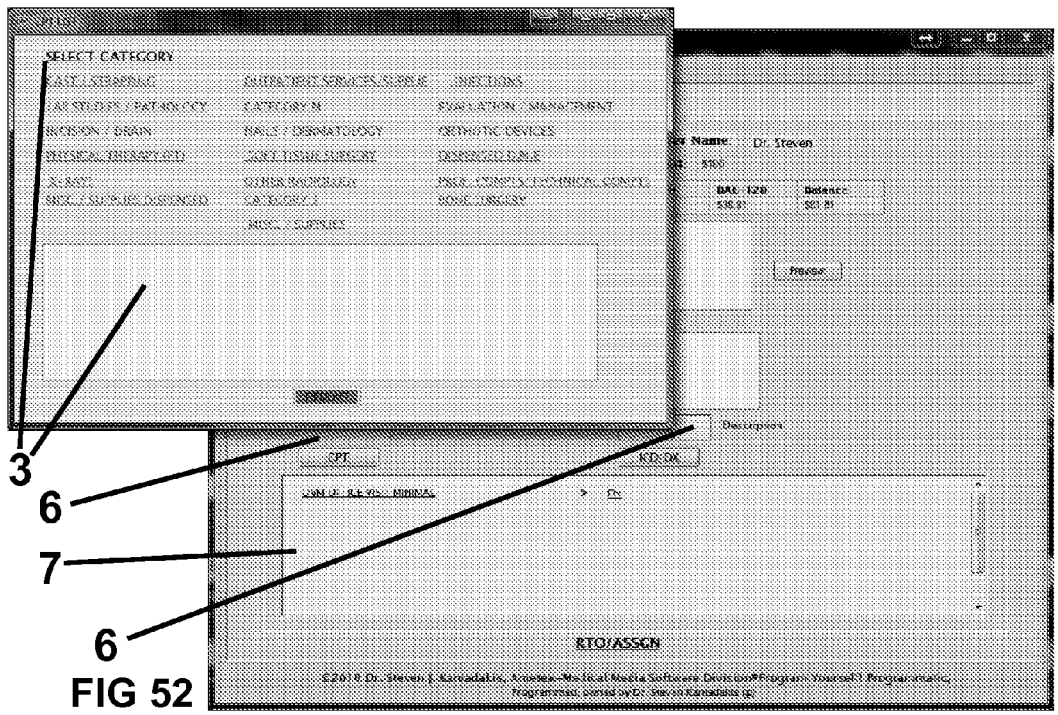
FIG. 52 shows a simple demo/model. Displays a previous embodiment screen view.
Figure 53:
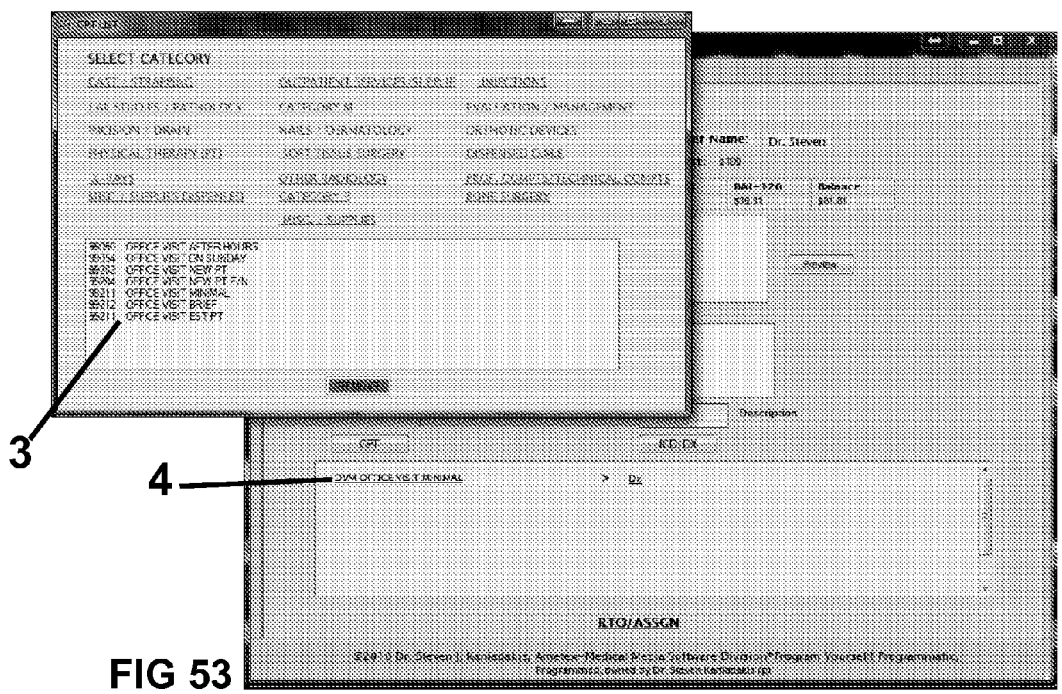
FIG. 53 shows a simple demo/model. Displays a previous embodiment screen view.
Figure 54:
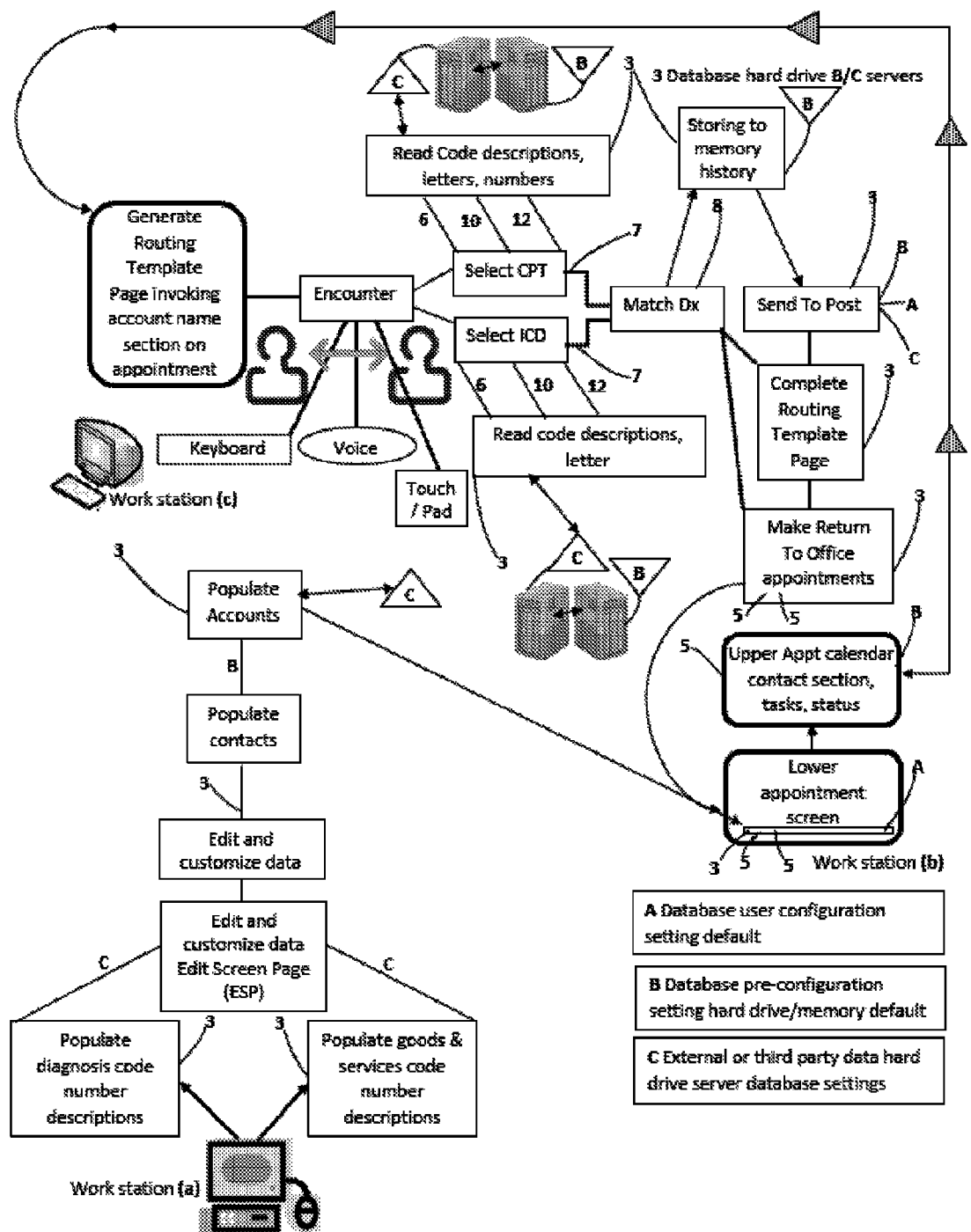
FIG. 54 shows a flow chart 1a including machine relationships to system, detailed embodiment of routing template and calendar related implementation, inter-relationship with servers and database tables.
Figure 55:
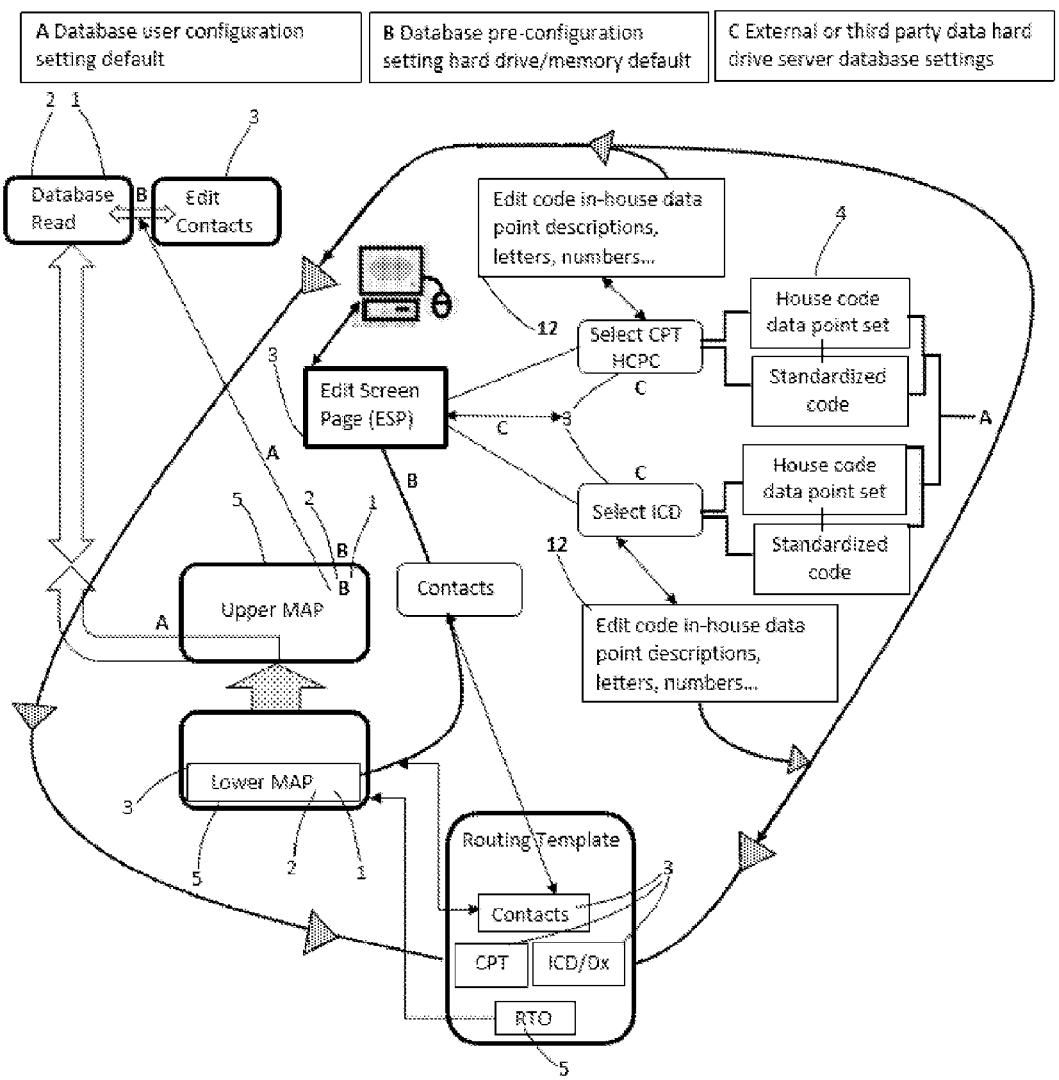
FIG. 55 shows a flow chart 1b including a relationship to detailed embodiment of routing template and calendar related implementation, edit (writing) configuring related database tables.
Figure 56:
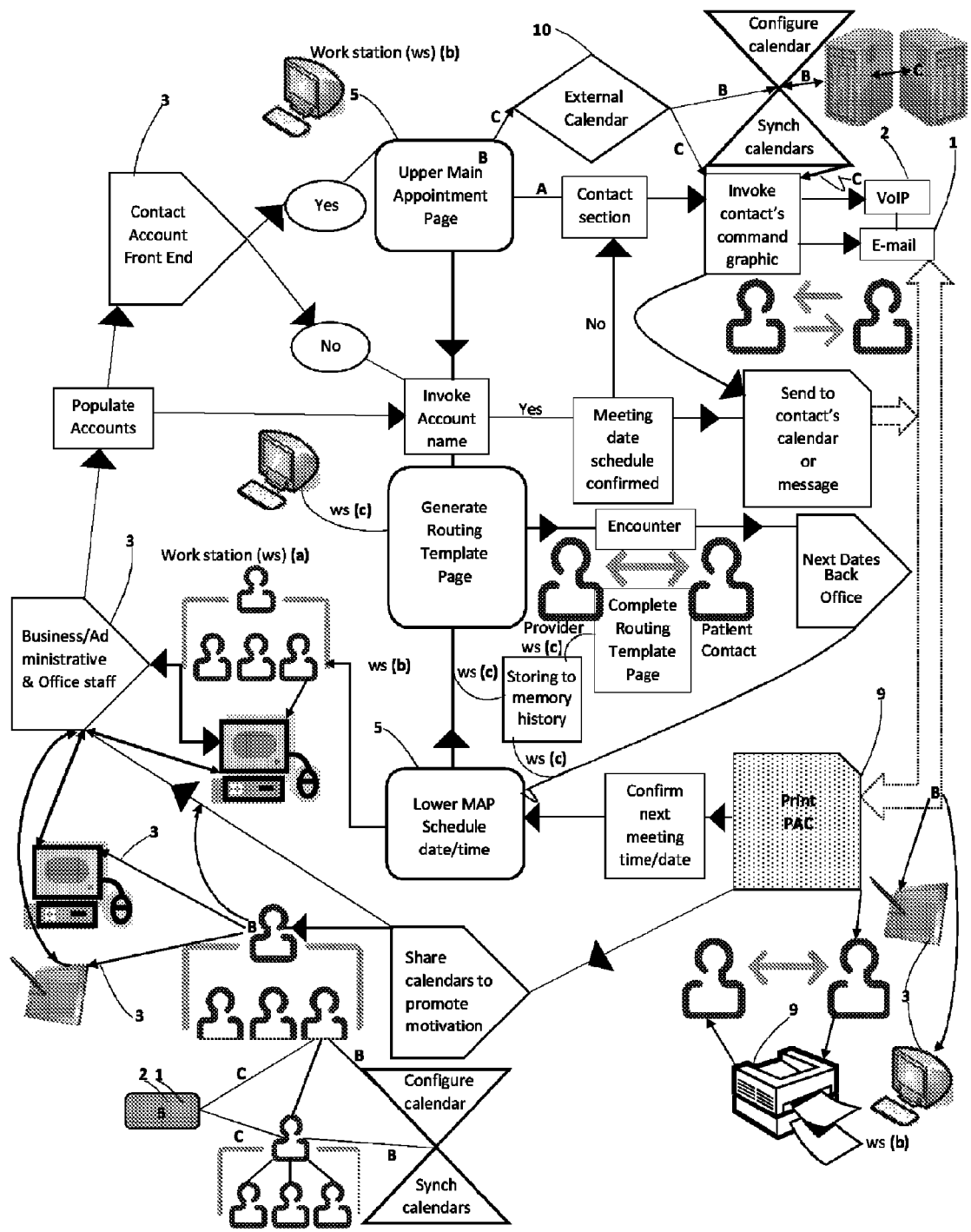
FIG. 56 shows a flow chart 1c including an overall relationship with other hardware and computing system networking taken together using method, machine and flow of data and computing system.

FIGS. 48 and 49 shows a simple demo/model. Displays a screen view of previous embodiments. FIGS. 48 and 49 show essential novelty of inventive art, converting code letters to code numbers and the reverse logic. OVM becomes 99050 and the reverse logic operating method works (or 99211) whatever numbers and/or letters end users port over or input to CPT and or H.C.P.C. data base. Like Morse code or like Windows picture icons, symbols replace complicated code and numbers. FIG. 50 shows a simple demo/model. Screen view. History of earlier implements and designs in development. Comparable to this embodiment. Another or previous embodiment, as in this including a dot net framework. Shows essential novelty of inventive art, converting code letters to code numbers and the reverse logic. OVM becomes 99050 and the reverse logic. The command controller, cursor, or arrow pointer 12 is shows fashioning code and the Programmatic texting aspect. FIG. 51 shows a simple demo/model. Screen view. History of earlier implements and designs in development. Comparable to this embodiment. Another or previous embodiment, as in this including a dot net framework. Shows essential novelty of inventive art, converting code letters to code numbers and the reverse logic. OVM becomes 99050 and the reverse logic. FIGS. 52 and 53 shows a simple demo/model. Displays a screen view. An alternate field is called Recall, FIG. 26 in RTO tab field, FIGS. 4 and 32, and "Recall" works the same as the action is synchronizing with the Make Appointment From RTO command graphic text and fields, lower appointment screen. Embodiment is pre-configured with a component of the previous component, FIG. 8A, and the practical component, FIG. 41, for making a phone call 2 and sending an e-mail 1 from the calendar 5 part when invoked inside the first and practical embodiment. The user can select from other database configuration settings. The embodiment's component part is intended to use other user based permissions and database configuration other settings on each the user's machines. Therefore, the inventor's method is geared for driving the machine in virtually any other application module executing a database configured for making a phone call and sending messages right from the users' selected calendar implementation and the inventive component thereof FIG. 41. Each can be configured for the users, and the idea remains the same created by the inventor. For instance, bridging FIG. 41 with scripting enables the idea to work in other browsers, platforms, and networking computing systems.

Figure 41:
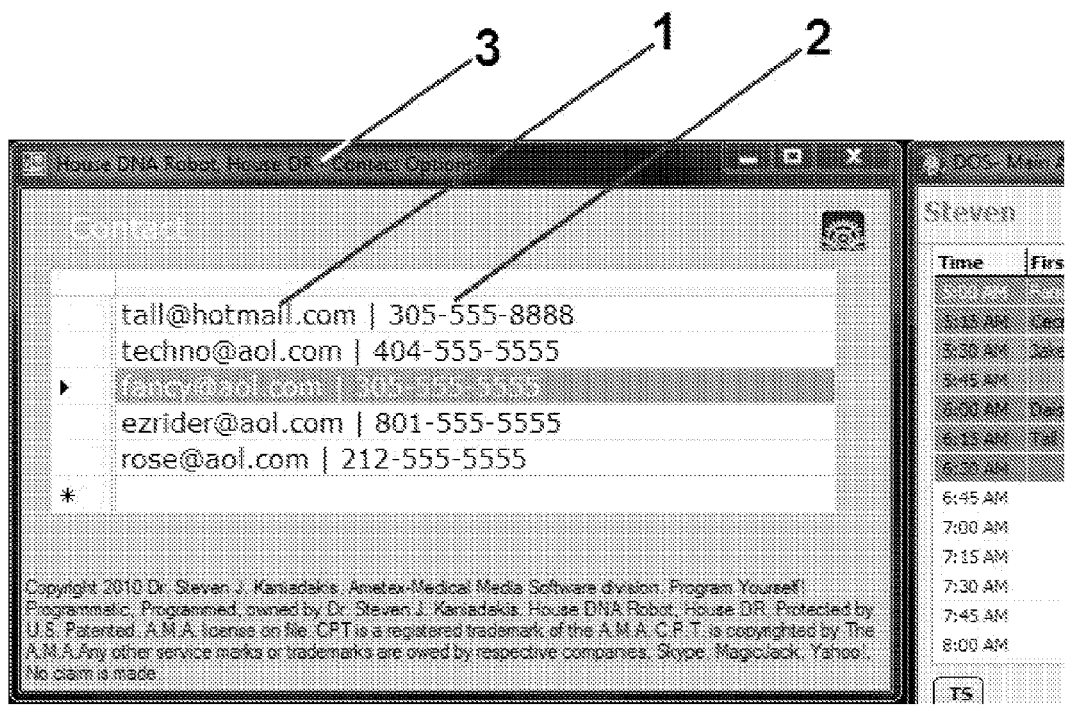
FIG. 41 displays showing contact sections, e-mail 1, phone call 2, messaging features; Configuration settings to select various messaging and/or phone providers.

Therefore, the idea is essentially irrespective of each programming language which can be working with the first embodiment of Main Appointment page to make phone calls and send messages from selected extrinsic and intrinsic calendars. This form of configuration for changing each the calendar's database to implement 2 and 1 can be employed. However, the first embodiment's technique utilizing the component part as with FIG. 41 shall be working optimally by using other scripting, and this has been mentioned in the first embodiment. Other scripting enables other database configuration settings, cross platform, cross browser and computing system applications of the embodiment's module identified in component parts thereof FIGS. 8A and 41, which is essentially driving the engine and machine executing in each computing system's database implementing this invention's interactive phone and messaging method. It does not matter, FIG. 41 is the practical component of the module geared for bridging and executing the database configuration. Regardless of the types of calendar implementation and other scripting techniques. The idea is working on various computing systems and calendars from external or third party programs are customizable. Pre-setting database configurations can be employed by the embodiment and components of FIG. 41 and part 5, and the FIG. 41 element of the routing template embodiment configured to another external calendar implementation with or without the embodiment of elements of the healthcare routing template screens. Enabling users to share this FIG. 41 component. 41 interactive fields and the functional module for reading data and interacting phone and e-mail interactive command graphics on contact section of configured calendar implementation.

A Scheduler Part—Main Appointment Page (MAP)

Figure 7A:
FIGS. 7A and 7B shows upper and lower part of scheduler parts called, Main Appointment Page (MAP screen)
Figure 7B:
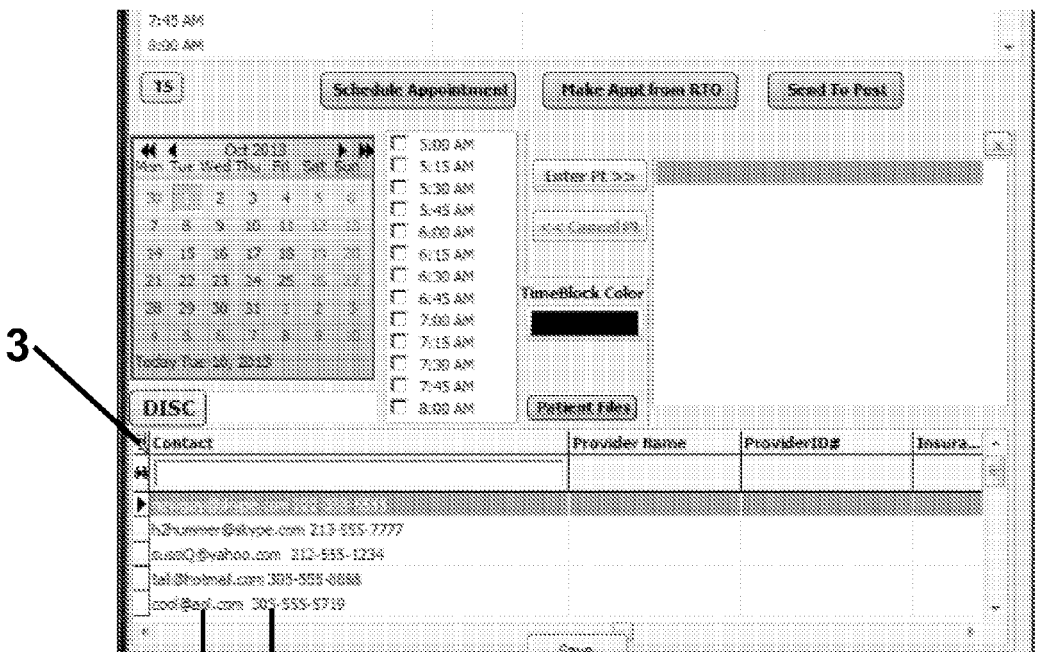

A description essentially from superior to lower screen or page opposing characteristics of a part of this invention is next given. Main Appointment Page (MAP display screen) is another part of this invention. This part assists to sort and handle records related to, but can be separated from, Routing Template. FIGS. 7A and 7B shows upper and lower part of scheduler parts called, Main Appointment Page (MAP screen). Lower part of the MAP also has 1 messaging or phone calling, 2, features therefrom patient data file 3 fields.

The caption displays "Provider", "Provider ID#", in a red color to distinguish treating Provider(s). Wherein embodiment creates a virtual "Appointment Book" that may or may not become unique patients for Provider or shared patients for multiple users of application. This is more fully described with the "Make Appointment From RTO" and a fore mentioned "Recall" field and interactive command graphic.

Next, a Date Of Service (DOS) in red color displays the selected date of the week from a Calendar of day and date the Appointment Book becoming displayed for viewing and for making entries. It becomes distinguished from the adjacent current date/time docket as current date is displayed as well (in black color) as the date and time docket displayed (in black color) corresponds to Routing Template date/time docket.

Figure 6A:
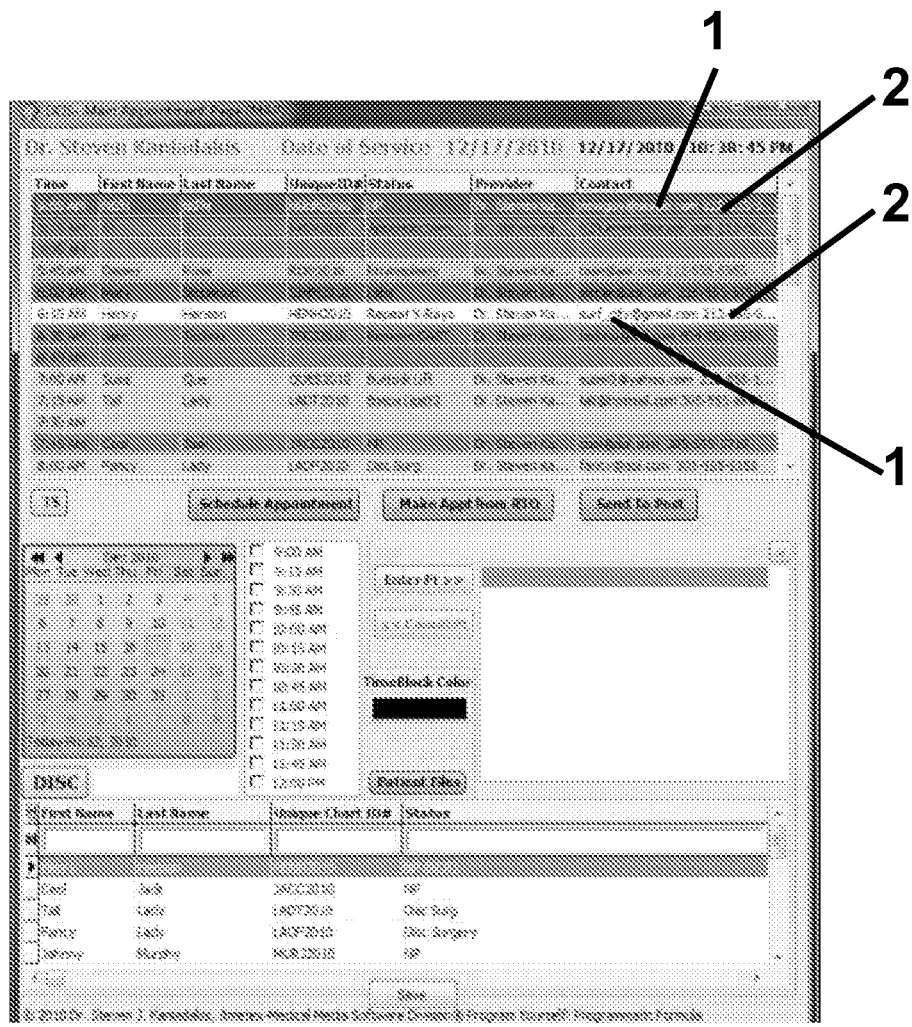
FIG. 6A displays contact sections, invoking actions on screens for e-mail 1, phone call 2, messaging features. See FIGS. 40 through 43.
Figure 8A:
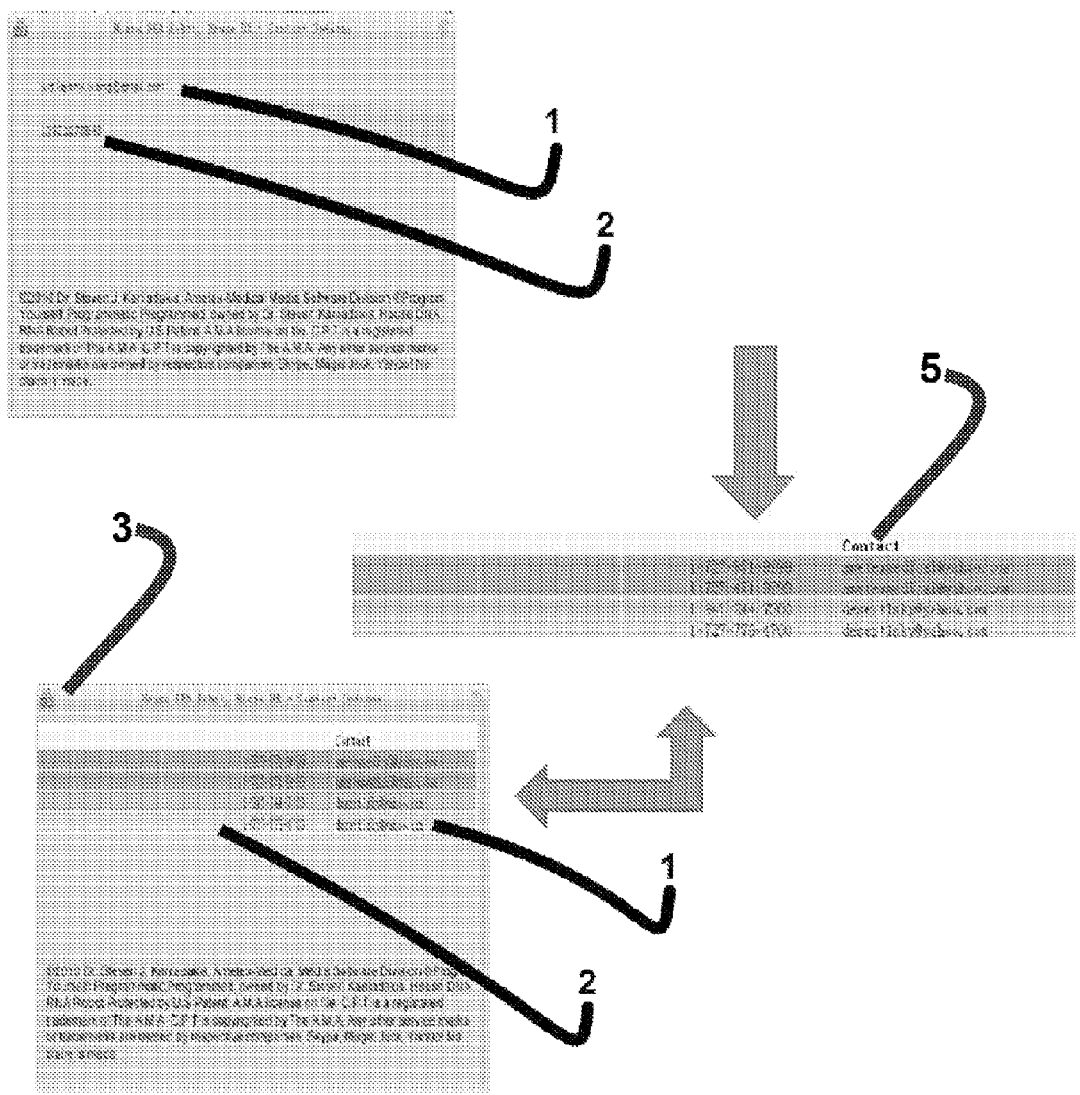
FIG. 8A is an alternative and previous component of the embodiment with configuration settings part, 3, and corresponding link to Main Appointment Page (MAP screen) for novelty contacting, messaging, 1, and phoning, 2, patients. Flow chart and schematic representation.
Figure 8B:
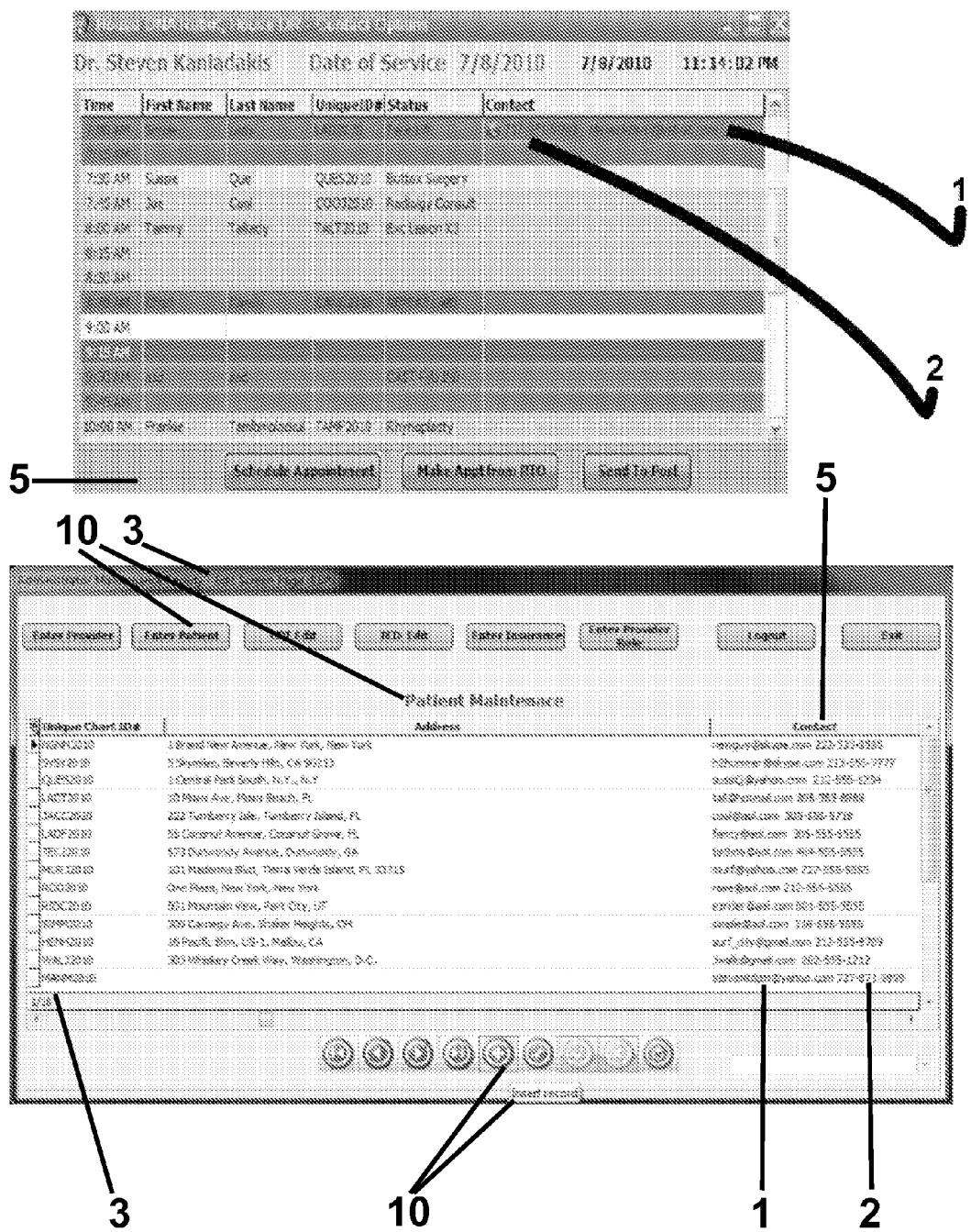
Figure 40:
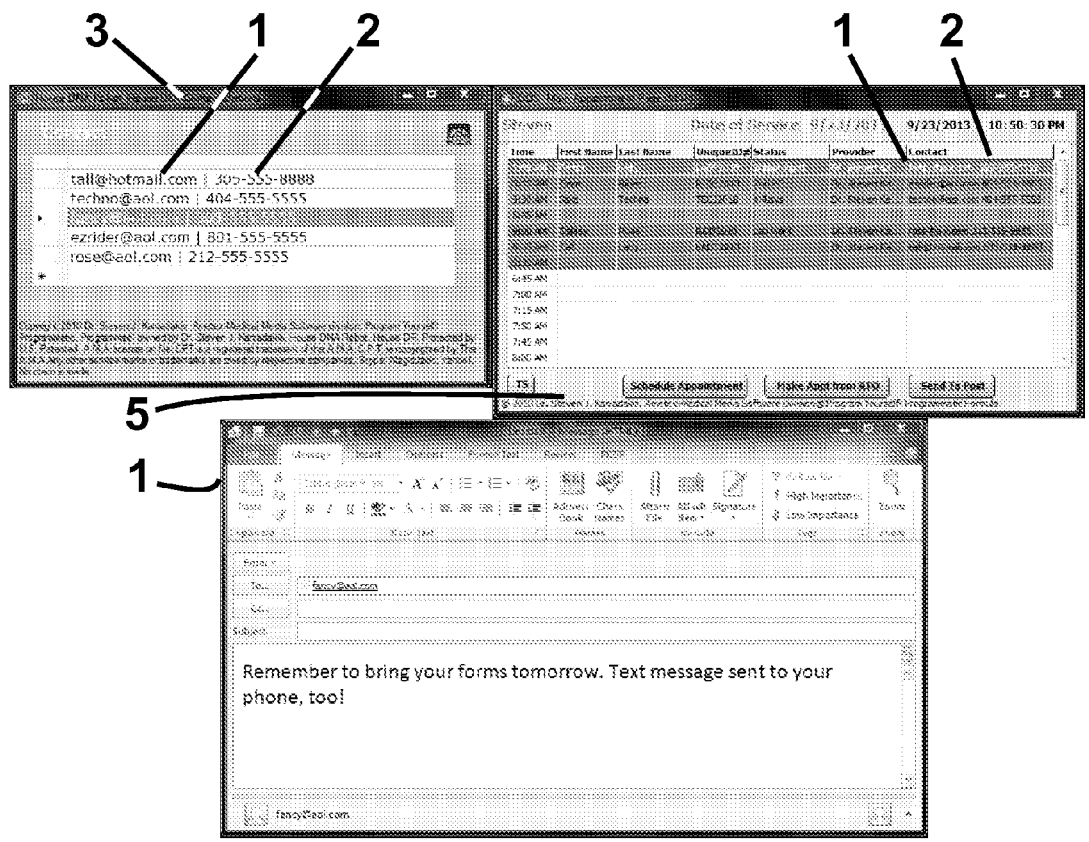
FIG. 40 displays novelty of art showing contact sections, invoking actions on screens for e-mail, phone call, messaging features. See FIGS. 6A and 6B.
Figure 42:
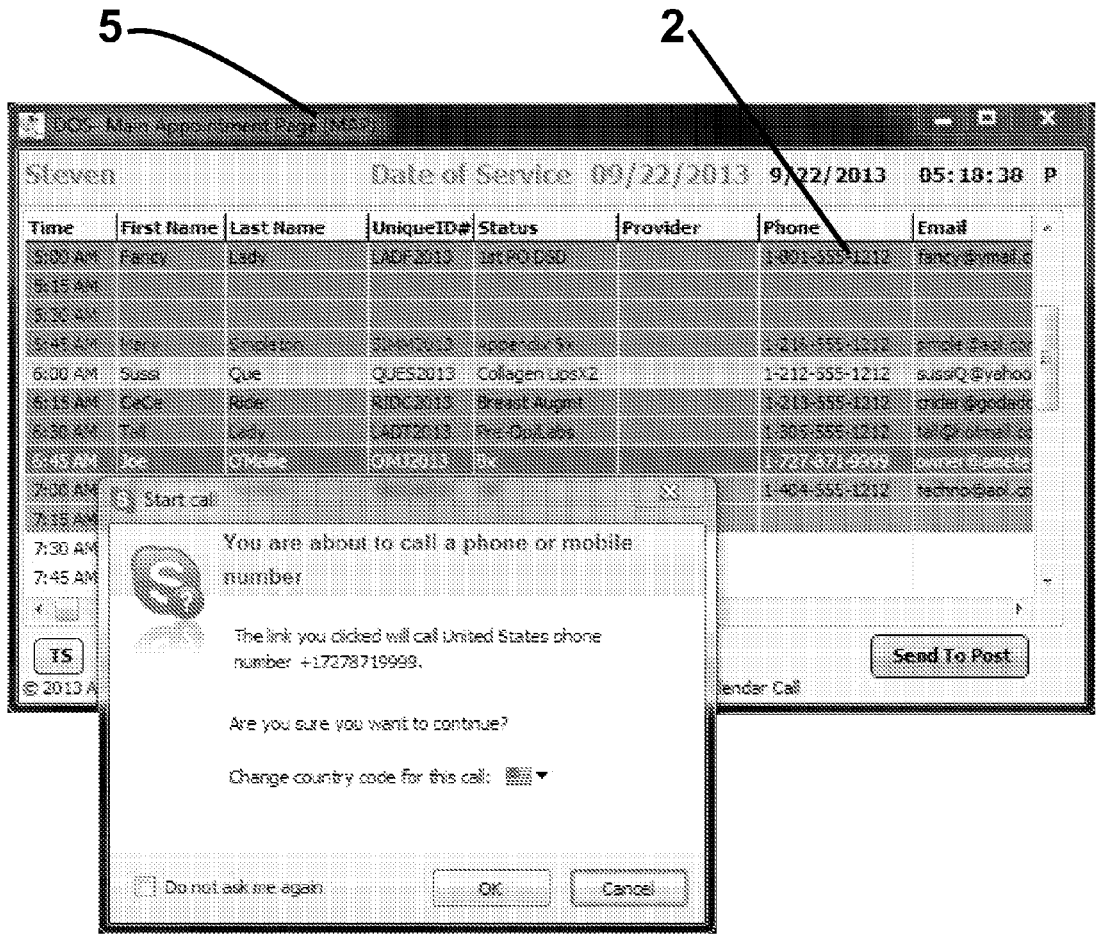
FIG. 42 displays showing contact sections, for e-mail, phone call, messaging features; Making calls 2 directly from computer and invention's machine implementation related 5 calendar method implementations by invoking phone and e-mail interactive command graphics. Collateral section, adjacent to phone and e-mail contact section, are interactive by invoking the routing template page for each corresponding account scheduled.
Figure 43:
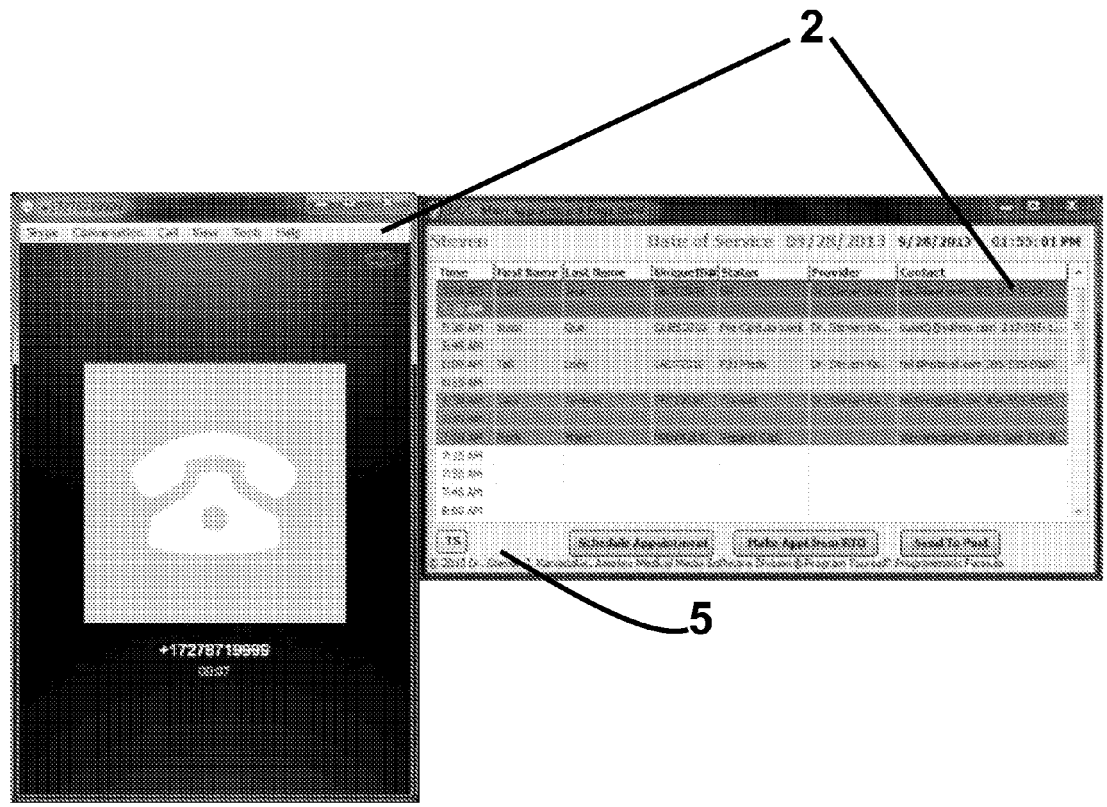
FIG. 43 contact sections, invoking interactive actions on screens for e-mail, phone call 2, messaging features from the selected 5 calendar implementation.

Generally, a part called "Main Appointment Page (MAP)" 5 is divided into an upper screen and a lower screen display, field or page, hereafter referred to as "Page". Refer to FIGS. 2 and 3, respectively. Upper Page of this screen, FIG. 2, is essentially an "Appointment Book" 5. FIG. 13 displays upper part of Main Appointment Page (MAP screen). Scheduled appointments, unique chart identification system, to invoke contact section implementation, to invoke touch screen (TS) implementation, to invoke send to post (STP) information on this related screen to a third part of external program. Make appointment from return to office invokes lower part of MAP to expand or open for return appointments (visits or surgery, for instance). This upper part of main appointment page for the application allows the user to click on the entry containing patient's name, and this action generates the aforesaid Routing Template page or screen (from FIG. 1). Functions are described above about implement of a Routing Template as it may become connected and to this invention with application instrument. This application allows user to touch/click patient's contact information in order to directly contact or notify the particular patient. FIG. 41 is showing contact sections of a calendar, and the inventive art's invoking actions on appointment related screens for sending an e-mail, making a phone call, and related messaging features. Configuration settings are enabling users to select various messaging and/or phone providers. Access is granted via configuration providing a computer, computer scripting code, and other pre-determined known type Voice Over Internet Protocol (VoIP) to make call directly from the appointment book selection, event and scheduling related fields, therefrom the end-user's selected phone provider(s). For instance, the particular patient or the client's contact is notified FIG. 8B by e-mail message 1, or by a pre-scheduled message, telephonic call or instant phone call FIG. 8B 2 directly from the application to another phone or computer able to make "telephone calls". This type of phone calling feature might be referenced as an "Internet Phone System", or known as a form of "Voice Over Internet Protocol, VoIP" system. FIG. 43. For instance, using a known type of VoIP and a form of "Skype" with IM, web camera, and "phone" 2 FIG. 6A or microphone, forms of "Skypay", or "Sky Phone" as other known type programs wherein users may become "subscribers" and when such implementation may become in combination to this present art's embodiment. FIG. 8A is an alternative or previous component part intended to work in combination with the practical embodiment with database and configuration settings part, 3, FIGS. 6B, 8B, 35A and 35B and corresponding link to Main Appointment Page (MAP screen) for novelty contacting, messaging, 1, and phoning, 2, patients. This is the structural and functional part working on calendar related implementation including accessing database tables and invoking the phone call and messaging from the client's database. FIG. 8B, top figure, is an embodiment showing the components of contacting and calling patients from upper part of Main Appointment Page (MAP screen), parts 1, 2, 3. The inventor claims the component parts of the embodiments of these parts working in particular other known type or pre-determined computer and computing device phone and messaging communication systems when in a combination together herewith a described "Appointment Book" 5 and characteristic of "Contact" design. FIGS. 40, 42 and 43.

Figure 5:
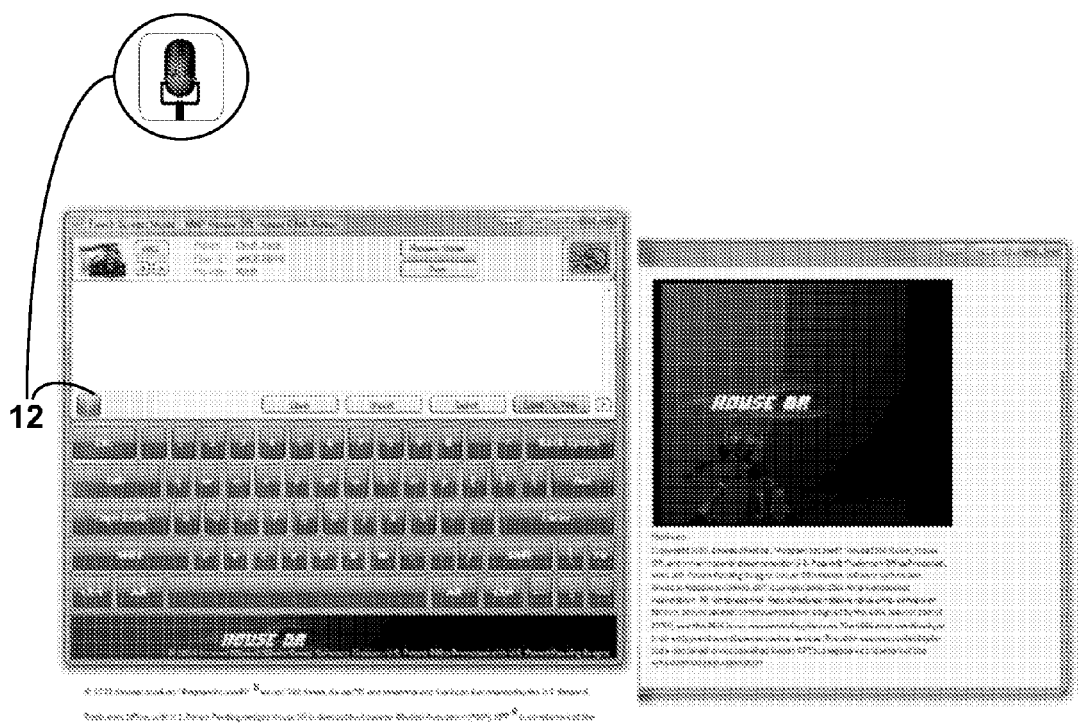
FIG. 5 is an embodiment of touch screen and related operations interactive command controller graphic 12. Compare with FIG. 14. Compare and contrast to FIG. 22. See FIG. 45.
Figure 6B:
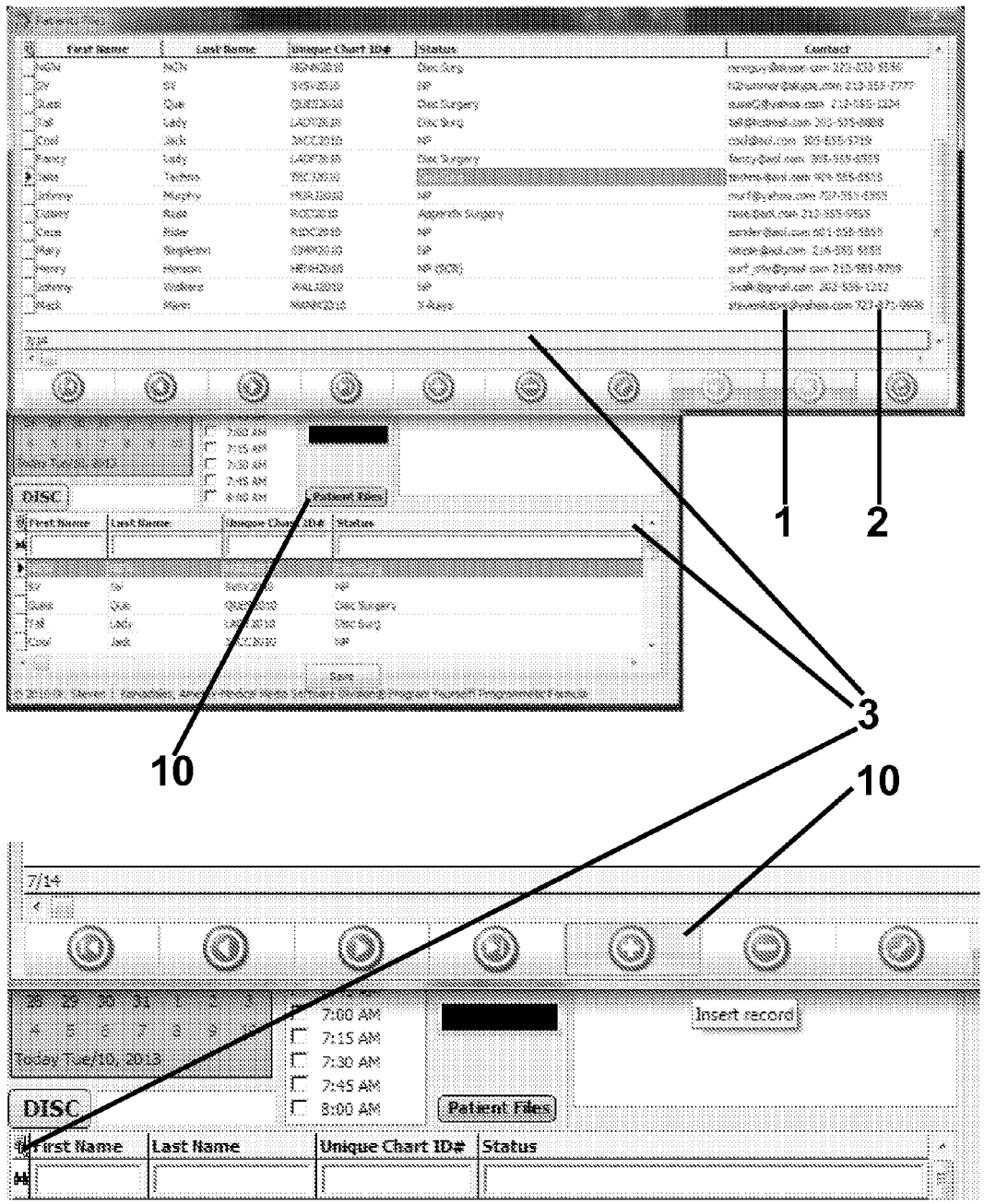
FIG. 6B displays contact sections, invoking actions on screens for e-mail, phone call, messaging features. Configuration settings, 3 (lower illustration). See FIGS. 40 through 43.

FIG. 42 displays another aspect and novelty of art showing contact sections, and invoking actions on display screens for sending e-mail, making a phone call, and related messaging features invoked from interactive command graphics directly from invention's method for calendar related implementations. This implementation and by using other known type voice-over-internet protocol from applications that were, until now, intended to work inside their own confinements of their software, implementation, or method and computer and other computing devices. See FIGS. 6A and 6B. FIG. 40, is showing how to send e-mail (foreground) directly from this embodiment's appointment book (shown in background) and related fields. Just click, press, or say FIG. 5 12 call and phone the client or patient from appointment book related implementations FIG. 6A displays contact sections, invoking interactive command graphic actions on screens for e-mail 1 and for phone call 2, messaging features. See FIGS. 40 through 43. FIG. 6B displays contact sections, invoking interactive command graphic actions on screens for e-mail, and for phone call, messaging features. This also is showing the user configuration settings, 3, whereby the user is selecting various messaging and/or phone providers (lower illustration). See FIGS. 40 to 43.

Figure 16:
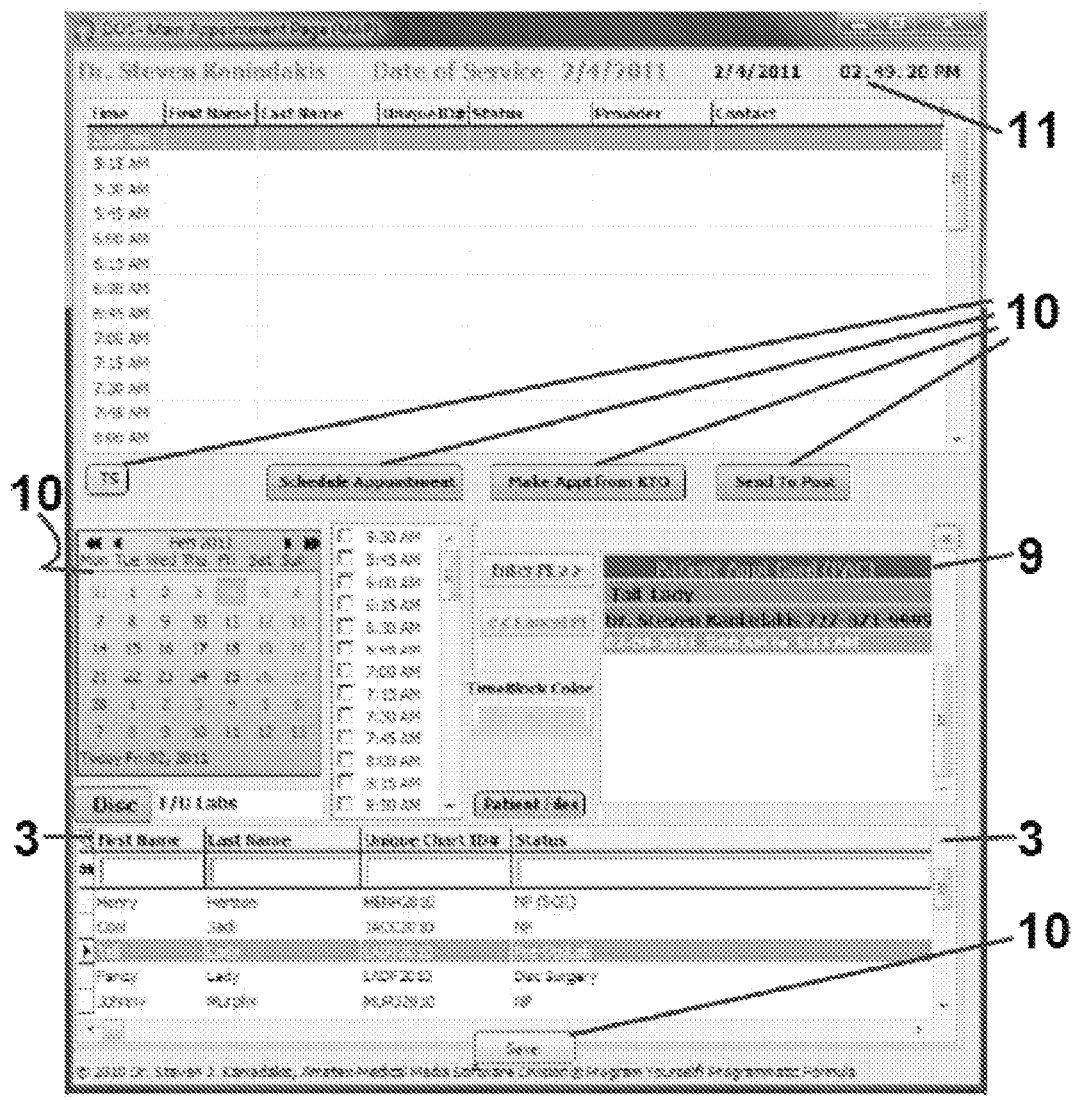
FIG. 16 shows patient Appointment Card (PAC) field is populated. Compare with FIG. 15 and FIG. 3, respectively. Compare with FIG. 7B, e-mail and related contact information implementations, in this lower part and MAP field.
Figure 17:
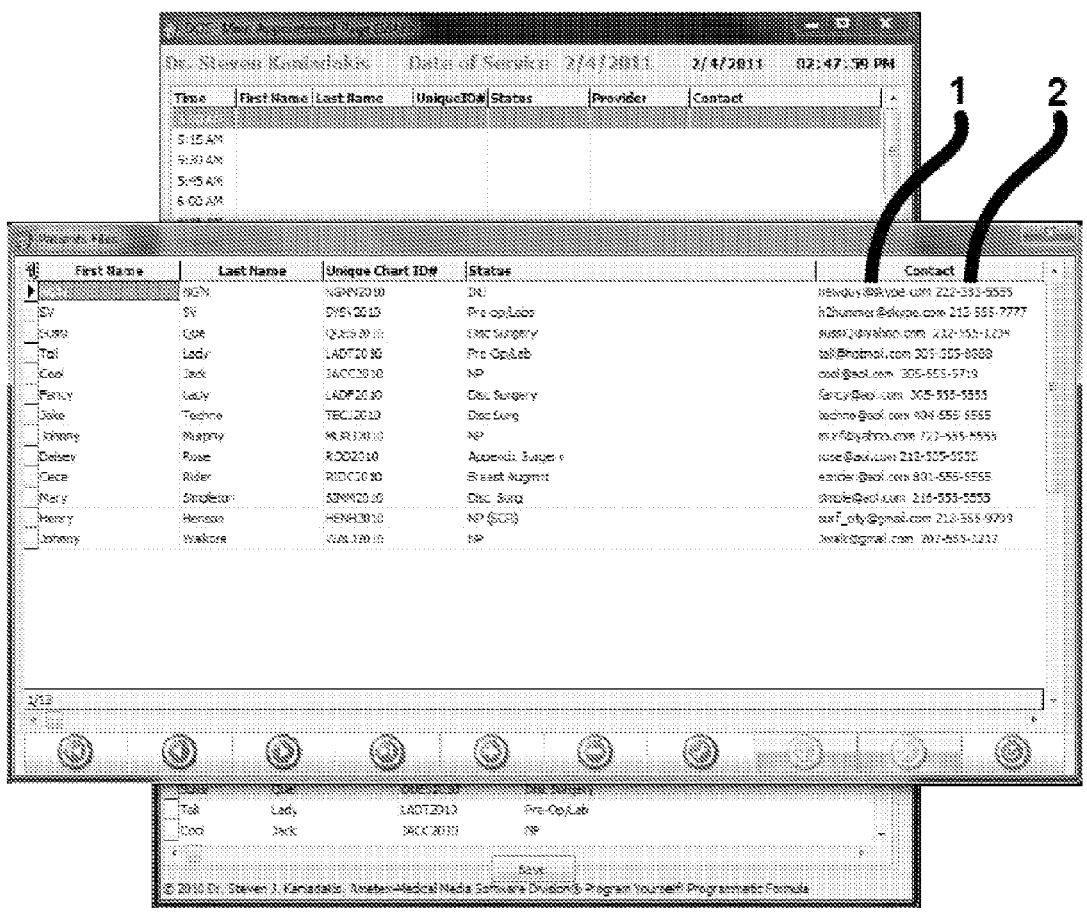
FIG. 17 shows patient files command graphic invokes field with novelty of calling patients using touch of a command graphic and one screen. Also, see FIG. 6B 10. See FIGS. 40 through 43. Compare with calling from appointment book, FIG. 2, novelty of contact section.
Figure 18:
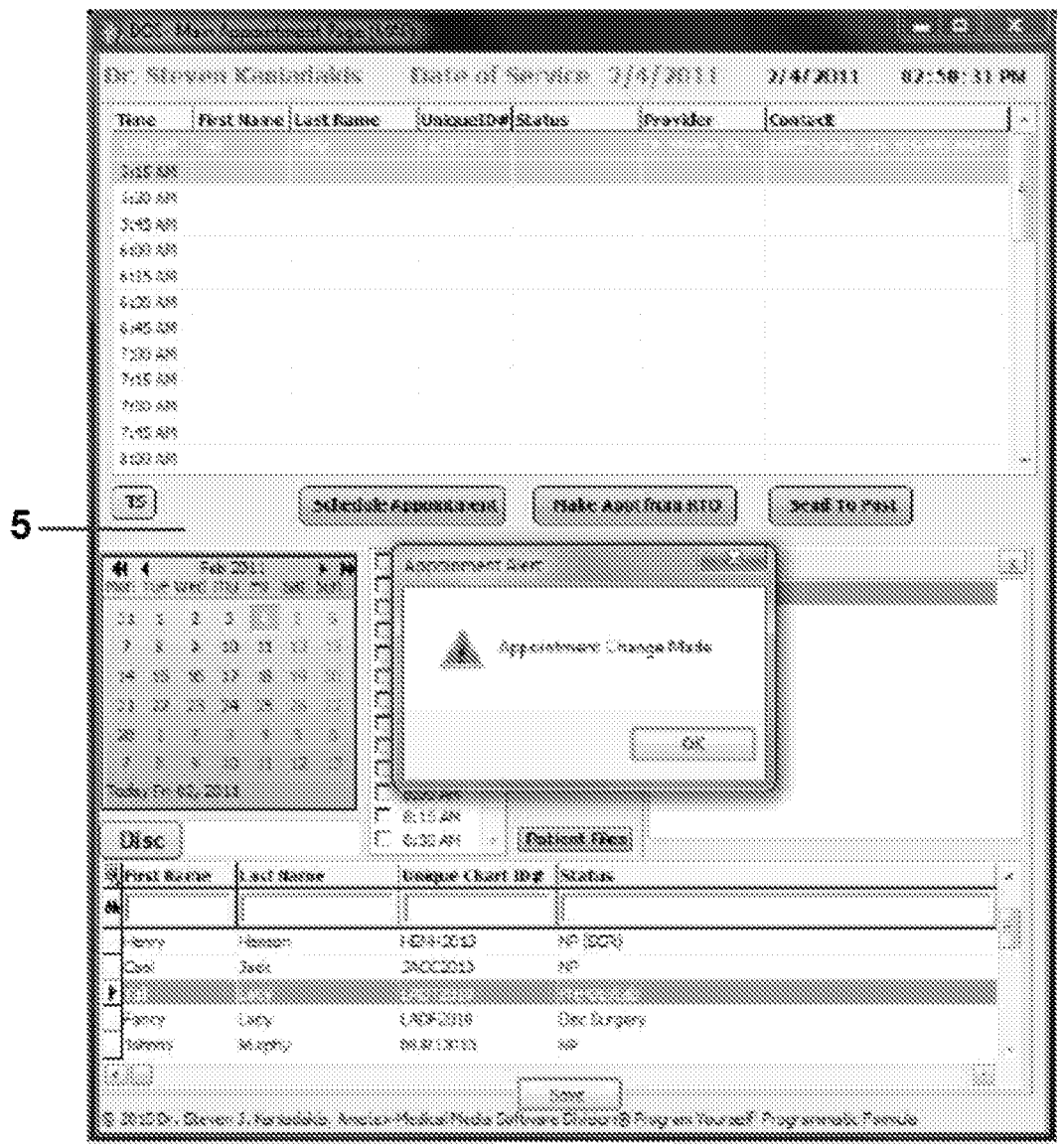
FIG. 18 shows a comparison to 10 FIG. 16, save command graphic acting like a button invokes appointments, shown FIG. 2 and here.
Figure 19:
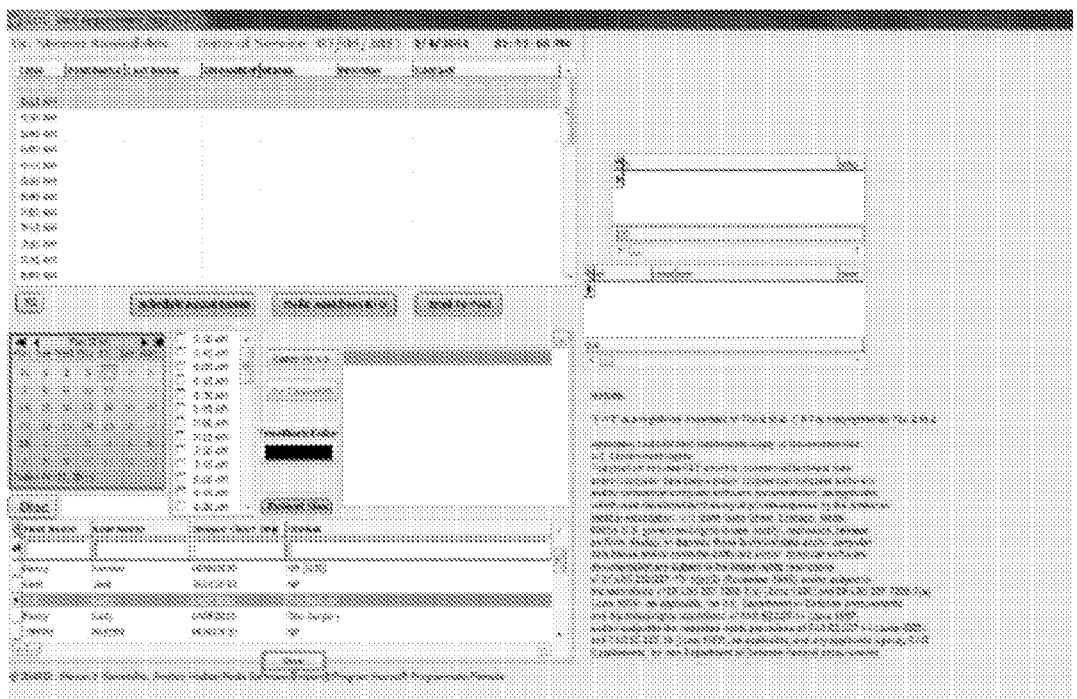
FIG. 19 displays an adjacent screen to the Main Appointment Page (MAP) when expanded. Compare with FIG. 47. Links to other companies, organizations, and their name and logo go here. Compare to FIG. 38.
Figure 36:
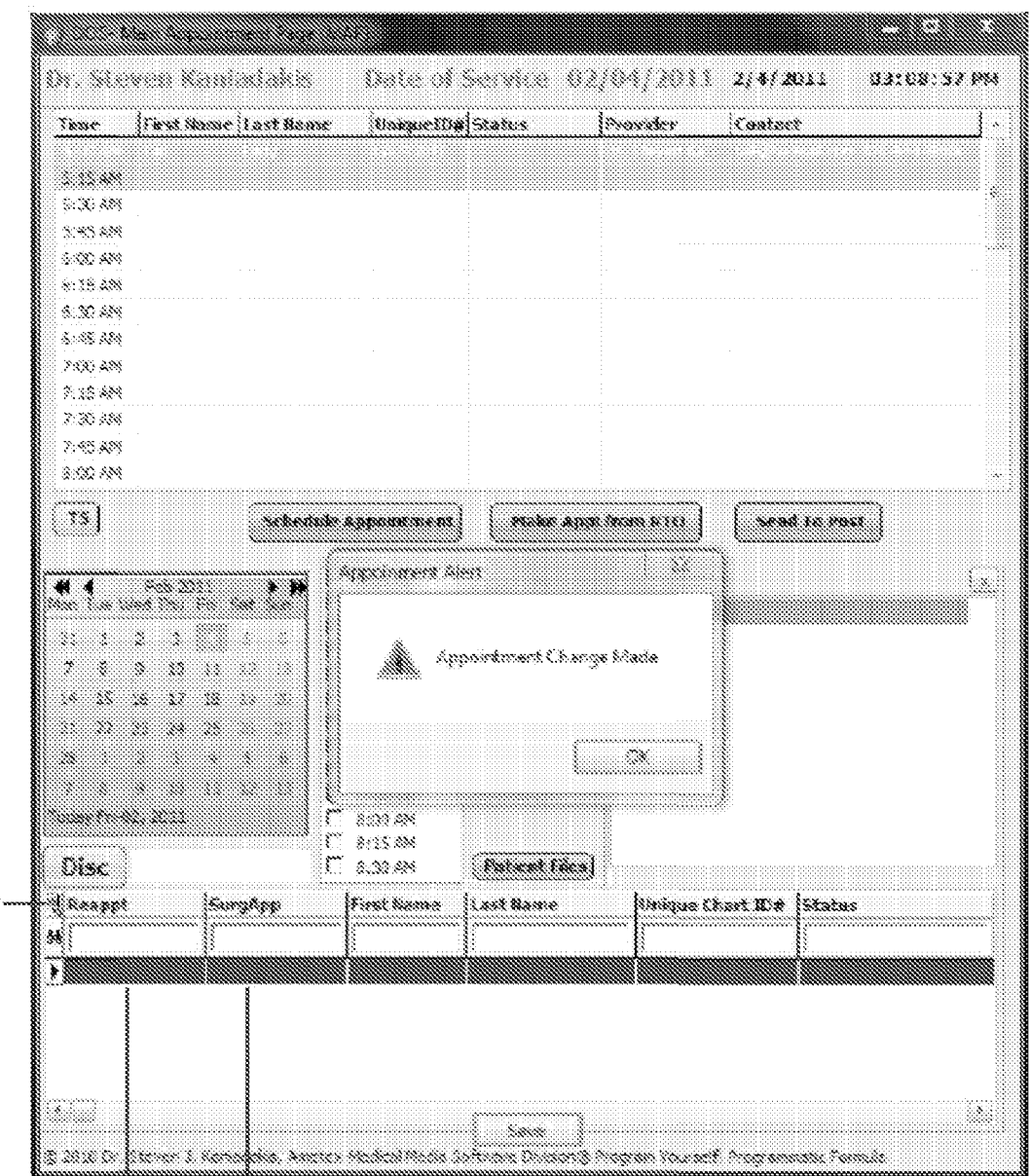
FIG. 36 RTO/ASSIGN "ok" sends appointments only to MAP. See FIG. 34.
Figure 37:
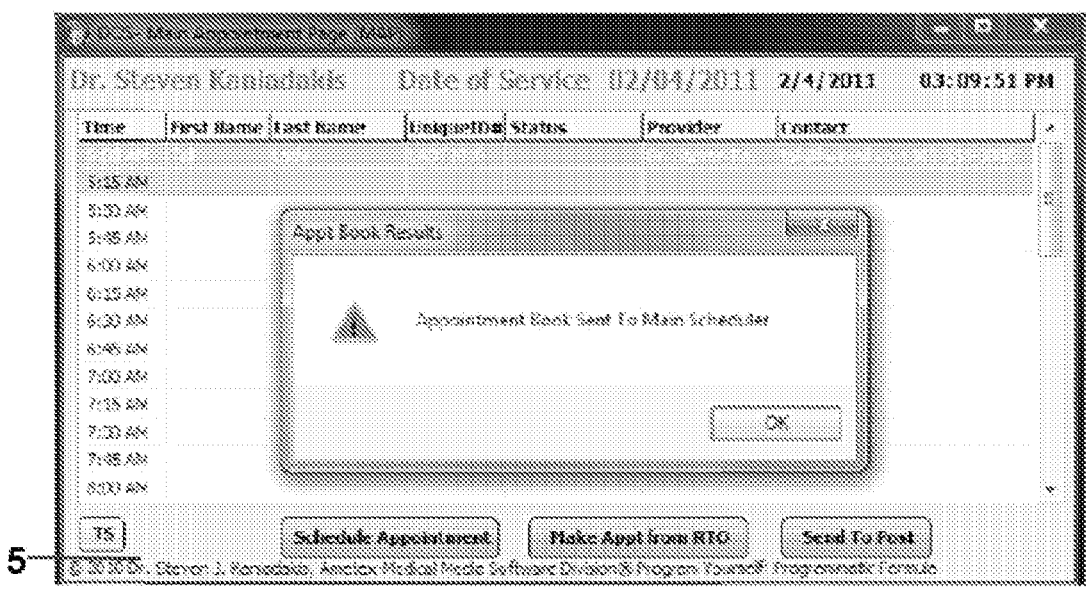
FIG. 37 shows appointments are Sent To Post (STP). Here STP is sending appointment related data to "main scheduler" 5 calendar.

A (large green command graphic is invoked showing text) "Schedule Appointment" command graphic 10 FIG. 16 is invoked for opening or expanding the lower page and fields. FIG. 3. It is designed to allow "back office" clinical staff to view part 10 FIG. 39 more related to Routing Template FIG. 27 parts 10 and 5, and the lower section or screen fields more related to administrative staffers or "front office" 5 FIGS. 35 and 36 FIG. 16 and FIG. 18 FIGS. 11A, B, C, D, F. Hospitals and other facility domains may lock this option, since there is a difference in amount of general flow with encounters between "front" and "back" as in reference to an office settings domain. Another (large green) "Make Appointment From RTO" command graphic 10 FIG. 16 is located on the top Page and adjacent the aforesaid mentioned. This enacts a very special screen displayed in an opposing screen to "Patient Files" field to enter patients and located in the same area replacing "Patient Files" fields. This "Make Appointment From RTO", sometimes referred to as "Recall" field, command graphic is more specifically described herein later. However, the "Make Appointment From RTO" interactive command graphic bridges data and exchanges the "Patient Files" fields of data with special fields stored 3 from "RTO" 5 data on Routing Template once "OK" is selected there from command graphic tabs located on RTO. Adjacent the vertical row of interactive command graphics acting as buttons on top of "MAP" is another "Send To Post (STP)" command graphic, and it is this latter interactive command graphic controller that sends appointment related data to populate via synchronizing and bridging database tables of an external program with only MAP 5 data information. FIG. 36 shows a contrast to FIGS. 33 and 37. FIG. 36 here sends specific appointment made to appointment book. RTO/ASSIGN "ok" sends appointments only to MAP. FIG. 37 sends to post all appointments from MAP to external or third party program, and FIG. 37 sends all RT information to same external or third party program for integration and migration. Again STP posting on MAP screen is distinguished from STP posting on Routing Template page screen, since both act independently. Independently, as the calendar related operation and the healthcare related operation. However, synchronizing operations and populating fields when used together using same application. FIG. 37 shows appointments are Sent To Post (STP). Here STP is sending appointment related data to "main scheduler" 5 calendar. Compare and contrast to FIGS. 35/36. Contrast to FIG. 33. FIG. 33 is the STP only sending Routing Template page screen data, and as shown on Preview, FIG. 32. Date(s) from RT is sorted and moves to this MAP screen, as in FIG. 36, and ready to invoke STP on MAP screen. Therefore, this relationship between routing template, preview, and main appointment screens are working to sort and filter data as a data bridge for confluence, synchronizing and populating fields of data in respective data tables FIG. 4 and FIG. 32, part 5. Also, see "Recall" field on FIG. 26. "Save" command graphic part 10 FIG. 16, FIGS. 34 and 36, sending appointment data to the upper appointment book implement showing message "Appointment Change Made". This should be distinguished from "Appointment Book Sent To main Scheduler" invoking "STP" on upper appointment book display screen.

Data essentially flows from the lower screen to the upper screen on this said "Page". Generally there is a flow from left to right with invention's design and invention's functional organization. At approximately the next middle-third of this Page FIG. 36 displays a "Calendar" field 5, a check off "Time Table" list field, an "Enter Patient" (green color) command graphic control, a "Cancel Patient" (red color) command graphic, a field called a "Patient Appointment Card (PAC)" field 9. FIG. 16 and FIG. 34. Just subjacent and proximal to FIG. 36 said "Calendar" 5 is a field called "Discussion" box (shown as "Disc"). Below the above-described fields is a field to search for and to enter patient data in a rather typical manner when taken a part from this application embodiment. "Enter Patient" causes checked times to become removed from the available Time Table, to prevent double booking or scheduling conflicts. Just subjacent and proximal to said "Time Table" field check list is a command graphic control text entitled as, "Time Block Color" to make an appointment block of time. FIG. 16 shows patient Appointment Card (PAC) field is populated. Compare with FIG. 15 and FIG. 3, respectively. Press on the patient's name and the information populates the fields. Save command graphic control 10 FIG. 16 populates, bridging and synchronizing, the appointment book (upper part). Date on calendar is selected (highlighted) and this date reflective of date of service at superior middle aspect, next to actual date and time documentation. Patient files displayed in a data base inferior aspect, with status and other information. Compare with FIG. 7B, e-mail and related contact information implementations, in this lower part and main appointment page (called the MAP) screen field.

Although presented as rather typical "Calendar", this Calendar 5 is interactive in several ways in combination 5 of invention's structural and functional characteristics. The user can view the "Appointment Book" for a given date selected from either calendar implement synchronized with the Page Calendar 5. The user selects by checking times of day in "Time Table". The user selects "Enter Patient". This data becomes displayed (see FIG. 16) in aforesaid "Patient Appointment Card" 9 (PAC) FIG. 16, hereafter referred to as "PAC" field 9. A unique characteristic of invention is to be able to "Print PAC" 9 invoking an interactive command graphic acting as a button. See FIGS. 11A and 11B. This is to give a patient a convenient list of appointment times/days. As simple as this might sound, advanced software related implementation and machine packages are deficient in this way when combined together with other characteristics of this invention. PAC also serves to identify this record for providers review. PAC also allows a quick review of what is identified in this application embodiment as patient's "Status". An aforesaid "Discussion" or "Disc" box is a field akin to "Disc" in this invention's Return To Office ("RTO") command graphic text tab and there is a synchronizing tabulated (tab) field located at FIG. 26 the "REAAPT" for "Reappointment". "Status" and "Disc" command graphic, and each the respectively named fields, are used interchangeably, since these functions relate to the same action. Thus, "Disc" text field box takes entered data from "RTO" FIGS. 26 and 27 and stores on a "MAP" field FIGS. 11A, 11C, 11D in order to complete next appointment for the patient. This is essentially an Appointment Book short hand note as to the reason of patient's visit on a particular date. It is statement as prepared by provider from Routing Template's "RTO" fields. Therefore, there is created a dynamic and confluent aspect synchronizing calendar related data table fields as well. Also, aforesaid "Disc" box field is located inferior to the MAP calendar, and the Disc and Status field can invoke the same action to make another reminder or notation (task, event) for any date on the Appointment Book. FIG. 16. A method "Disc" information is stored to data tables in relation to "Status", and the method other "Return To Office ("RTO") information becomes sorted and subsequently handled, is more fully described herein. The method is with reference to aforesaid "Make Appointment From RTO" command graphic, and each the related screen fields synchronizing the data, therefrom invoking each named text command graphic text action like a button is discussed hereafter.

Figure 11A:
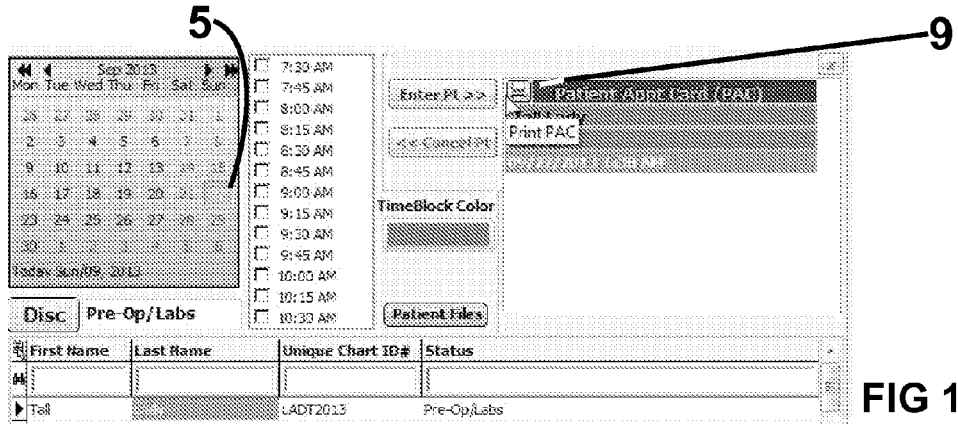
FIG. 11A, B, C, D, E, F shows the logic from screens related to Main Appointment Page (MAP screen) upper and lower parts. Advantages to use of one (touch) screen, instead of need to go to another screen burdensome various screens and fields. Here, the calendar, and related information essentially all in one screen and user interface design with routing template and scheduler; to maintain communication. See FIG. 34. Print Patient Appointment card (PAC) field 9.
Figure 11B:
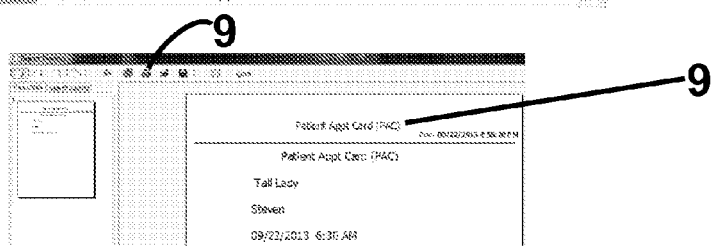
Figure 11C:
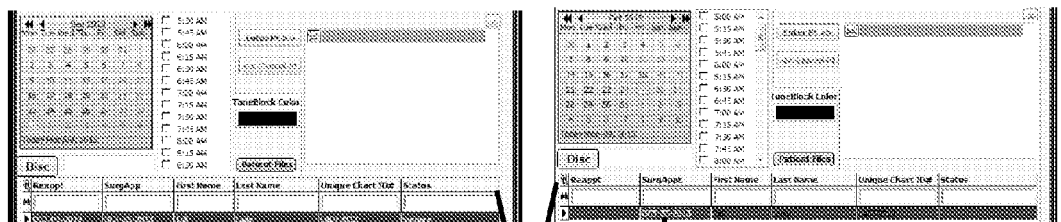
Figure 11D:
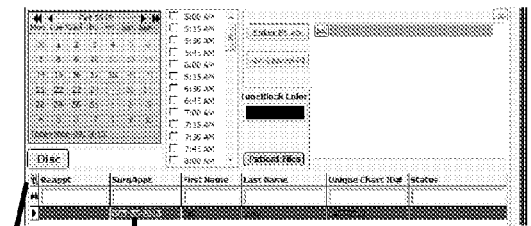
Figure 11E:
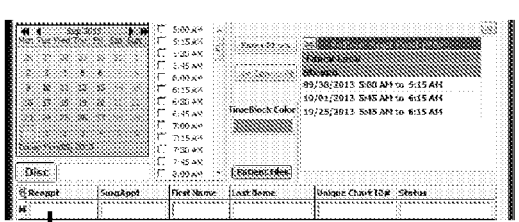
Figure 11F:
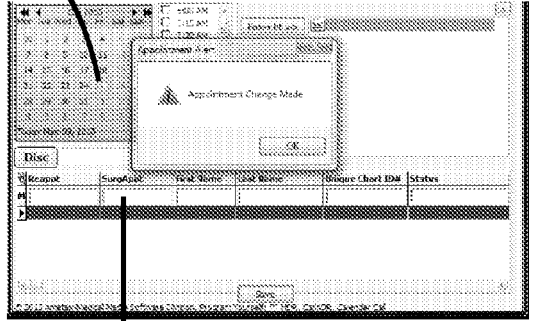

An aforesaid "Make Appointment From RTO", which is sometimes (see FIG. 32) referred to as "Recall" field, command graphic controller is located at the top section of "MAP". Invoking the Make Appointment From RTO command graphic action displays and activates a synchronizing and dynamic field at an area near the bottom aspect of the page. FIGS. 34 and 36, part 5. Therefore, Make Appointment From RTO becomes a synchronizing and dynamic display field that takes data table reports from RTO data tabulated (invoked by the RTO command graphic tab) fields thereby creating the synchronizing and dynamic field corresponding with Routing Template and the bottom of the MAP field. Therefore, this special field will synchronize and show the "Disc" data field from provider data entered comments entered in RTO "Disc" command graphic tab FIGS. 26 and 27. Accommodations are placed in a dynamic and synchronizing field thereby reflecting the same data in the field corresponding here on "MAP" FIGS. 15, 11A, 11C and 11D. Generally, the Routing Template commands the flow of data in this instrument or tool as the Routing Template commands and dictates FIGS. 16, 17, 11A, 11C, 11D a central part of this invention's unique novelties. However, in this instance ancillary staffers can enter and override the Disc and Status remarks as needed as indicated FIGS. 15 and 17 or as ordered (Rx) by provider's policy of conduct. This Disc and Status field further synchronizes in order to replace the Disc and Status data fields located in the "Patient Files" field data tables FIG. 17. Also, see FIG. 6B, 10. The Disc and Status field in the dynamic field of Patient Files data is a field located FIG. 7B virtually at the same location (near the bottom) of "MAP". FIG. 16. A key difference is that this field will also include a field that displays implement's related application calculated Return To Office (RTO) date, as stated from command graphic text tab on "REAPPT" command graphic text tab from RTO 5. Therefore, this date gathers in this alternate screen from action of "Make Appt From RTO" 5. Indeed, this field will show this date in order for secretary to "Make Appt From RTO" date. FIG. 34 shows a scheduler, lower part of Main Appointment Page (MAP screen) shows data sorted and sent from Routing Template (RT) fields of RTO/ASSIGN, shown in FIGS. 26/27. Easy to determine date and reason for return. Again, these features are acting as the data bridge for sorting data into respective data tables. A command graphic control is located in area of this for secretary and scheduler to view "Review-Preview" and "Review-Preview" thumbnail history as displayed from Routing Template. In order to make other appointment related and business related matters. Therefore, this quality is to maintain clinical communication to administrative or office staff. Literally to help make certain that front and back are as the expression goes "on the same page" 5. FIG. 35 shows a scheduler, lower part of Main Appointment Page (MAP screen) shows data sorted and sent from Routing Template (RT) must complete dates for both parts, surgery date and regular appointment date to have entry removed. See FIG. 36. Patient cannot be totally responsible when patient goes to check out to remember Provider's return orders and instructions. This field stores "Disc" annotations and date of patient's next visit data parts 3 and 5 for an easy reference for parties to communicate in a confluent, synchronized, smooth, seamless, flawless manner. At this point front office staff co-ordinate with the patient a mutually accepted day of the week and more particularly a "Time" of day are essentially all that is required. Thus, completing schedule elements and Appointment Book for particular Provider and patient in a more exact and intensive manner. Thus, application shows a very comprehensive communication that is maintained on various levels as demonstrated by this invention's tool or instrument. FIG. 11A, B, C, D, E, F shows the logic from screens related to Main Appointment Page (MAP screen) upper and lower parts. FIG. 11A printing patient 9 appointment card (PAC screen); FIG. 11B is showing a preview of Print PAC providing computing monitor or displaying screen and a computing system. PAC information can be electronically mailed 1 and sent to each contact (to each patient), or invoking the PAC command graphic or sending PAC to printer and to physically hand deliver appointment related card to patient or contact; FIGS. 11C and 11D return (reappointment) date information from Routing Template to 5 lower screen of the Main Appointment Page, e.g. surgery date and/or regular appointment date; FIG. 11E use of one (touch) screen, instead of need to go to another screen burdensome various screens and fields. Here, the calendar, and related information essentially all in one screen and user interface design with 5 routing template and 5 scheduler; FIG. 11F fields clear once (each) appointment(s) task is completed to maintain communication. User interfaces reduce errors and omissions. See FIG. 34. Fields are confluent with 5 routing template page. Print Patient Appointment card (PAC) field 9.

Therefore, near the opposing end from the Main Appointment Page (MAP) part FIG. 16, 11A, 11C, 11D of this application will be fields to store 5, 10 RTO FIGS. 26 and 27 information 5. Also see FIG. 15. The "Patient Files" command graphic controller returns fields to enter and change patient database 3. The "x" command graphic will collapse or close the lower screen on MAP to show only the "Appointment Book" (situated at top part of MAP) 5. FIG. 2.

Thus, this sequence is repeated in order to bring arrangement back as described, upon a patient's return to office visit.

Touch Screen Operation

Figure 14:
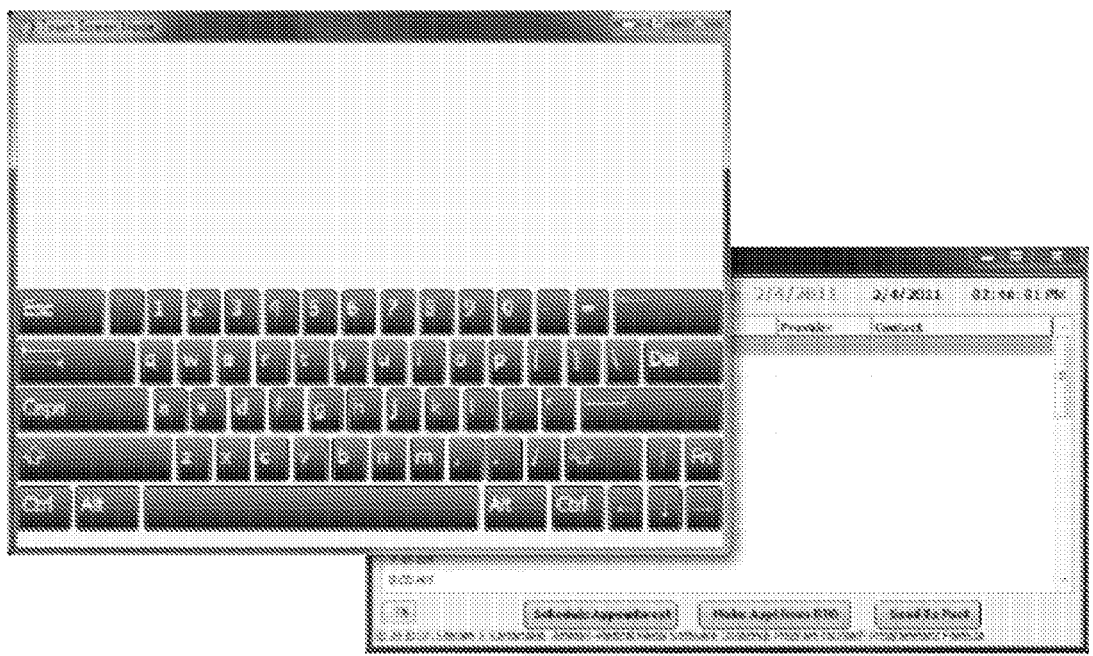
FIG. 14 is a previous embodiment touch screen mode. Compare and contrast to FIG. 22, pops up in routing template implementation.
Figure 15:
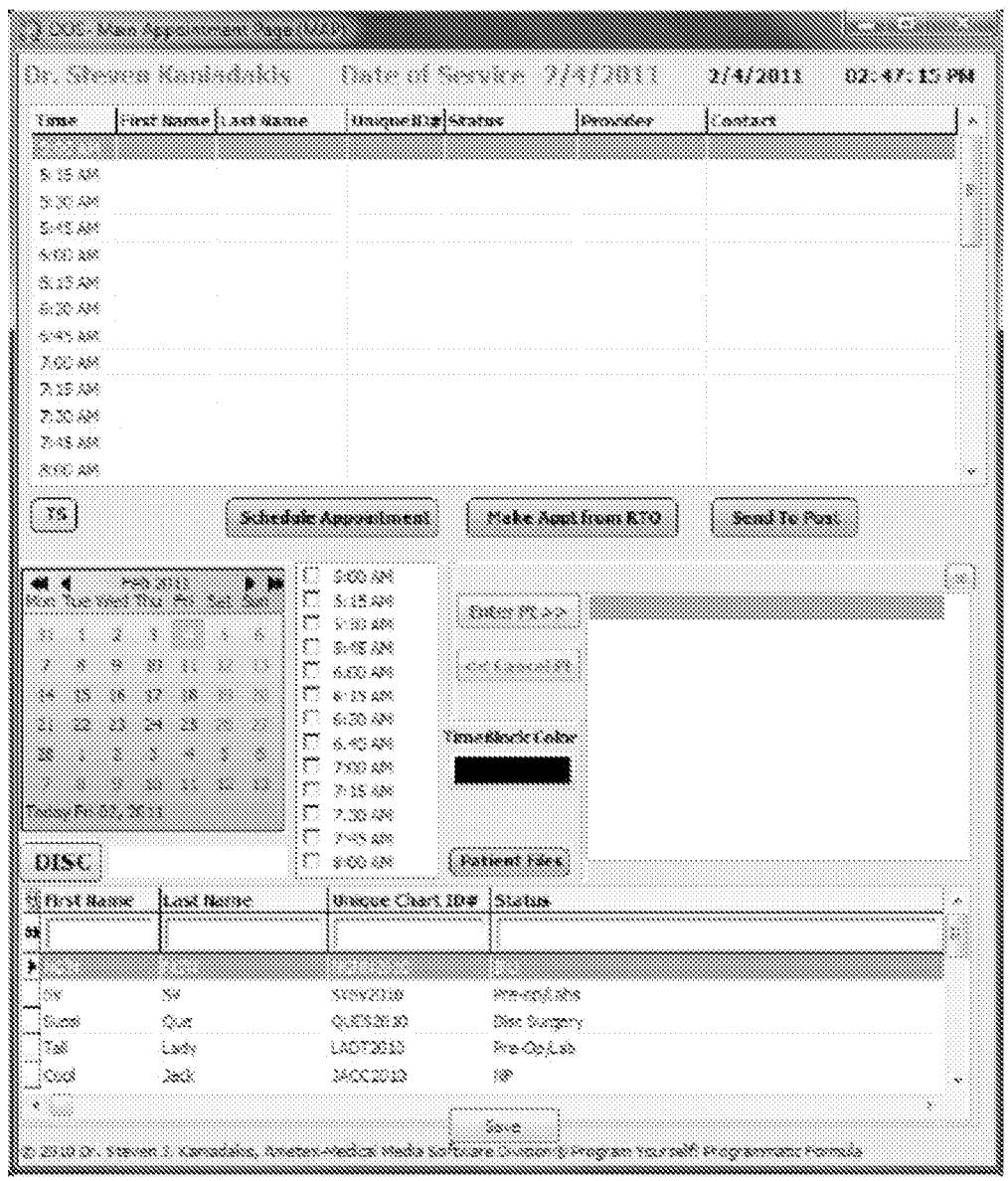
FIG. 15 shows main Appointment Page (MAP) extended, upper and lower screens. Compare with FIG. 16.

Routing template and main appointment page screens described above are in common to a touch screen implementation. FIG. 5. The symbols "TS" 10 FIG. 16 is the interactive command graphic controller that invokes touch screen related 12 FIG. 5 operations. FIG. 5 is an embodiment's of touch screen component and related operations. Touch screen mode opens in this screen or user interface viewed here. Compare with FIG. 14. Compare and contrast to FIG. 22, pops up in routing template implementation. The mnemonic texting feature and each the data sets of extracted code letters, numbers and/or descriptions can be utilized therefrom each the users' customizable database. See FIG. 45. FIG. 14 is a previous embodiment's touch screen component mode. Touch screen (TS) command graphic pops up or opens screen in same user window (view) and the same interface, here background is the Main Appointment Page (MAP screen) user interface opened with touch screen implementation in foreground (over top MAP screen). Compare with FIG. 5, one TS part of the embodiment. Compare and contrast to FIG. 22, pops up in routing template implementation.

Figure 22:
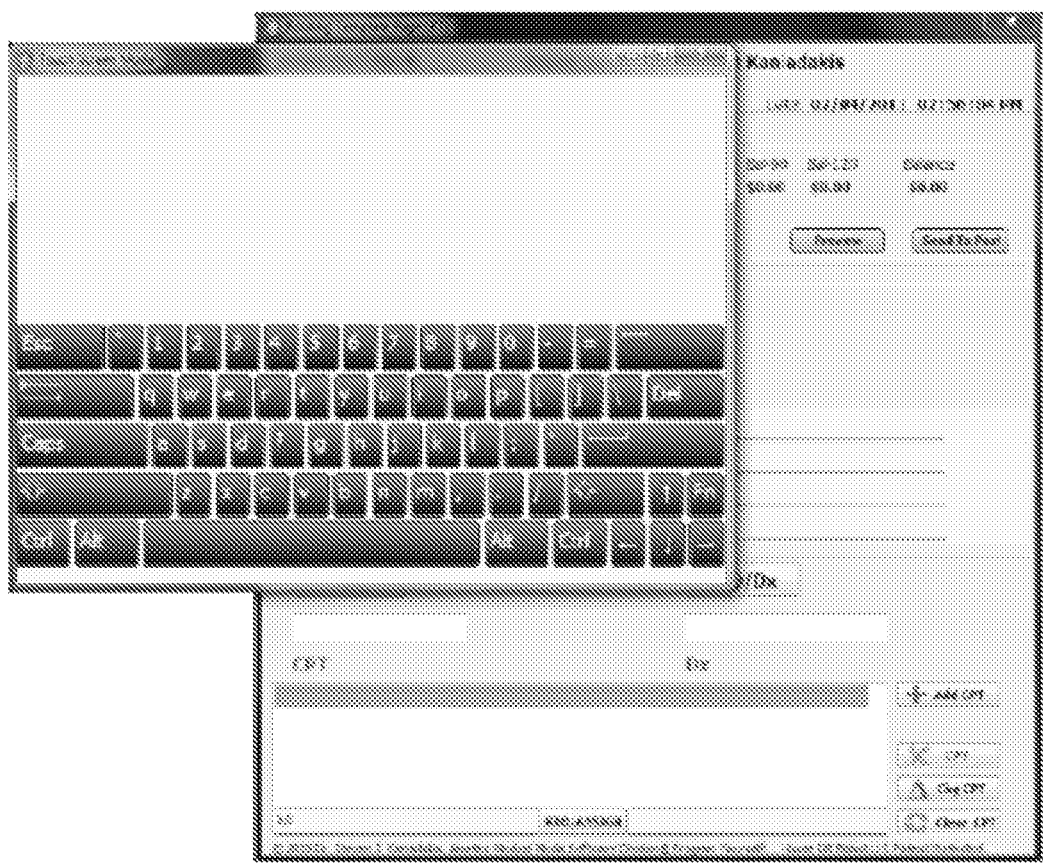
FIG. 22 shows a contrast to FIG. 14, on MAP screen, this is touch screen (foreground) on Routing Template (RT) page (background). This is a previous or other component implement invoked from the first embodiment.
Figure 23:
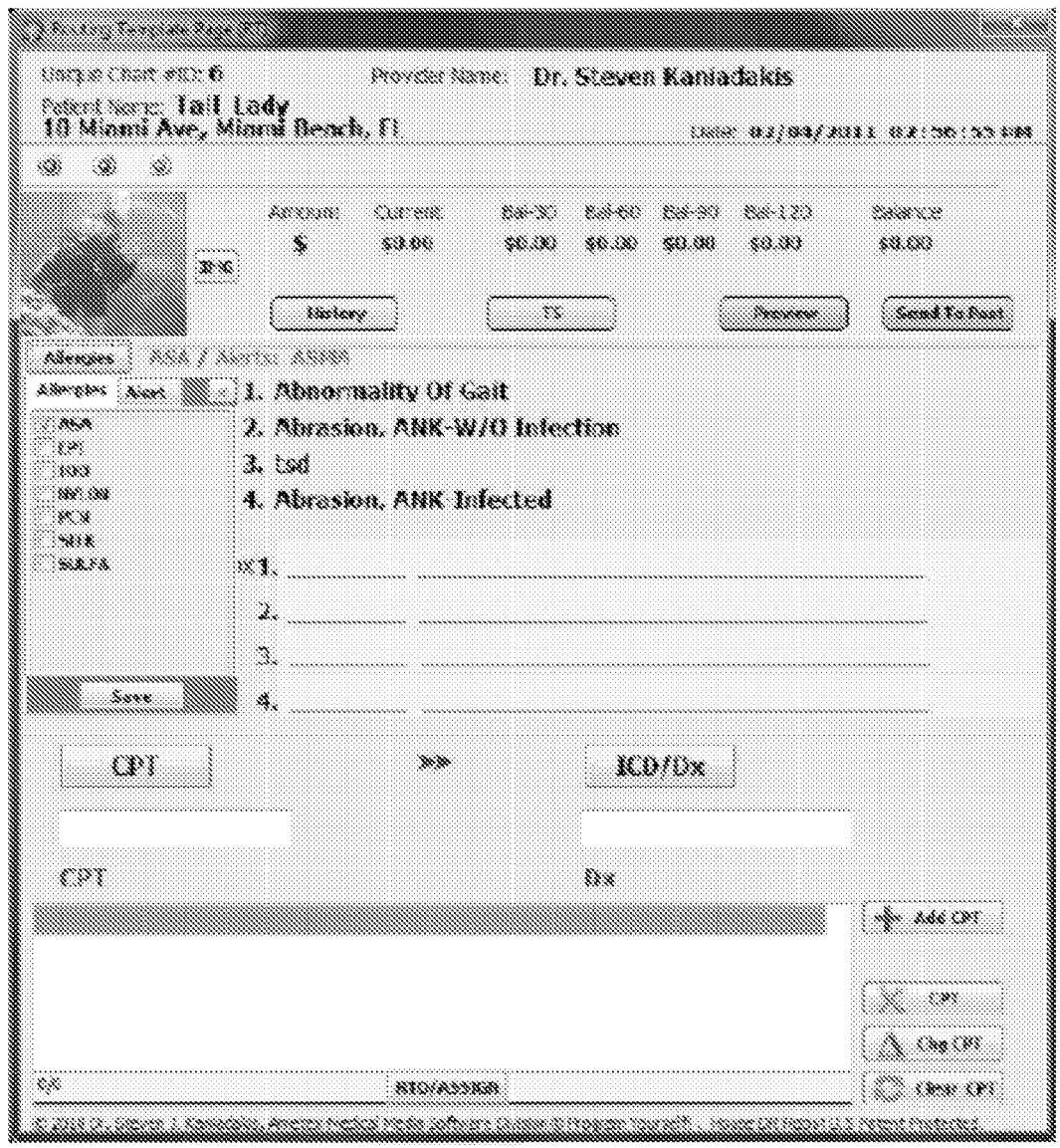
FIG. 23 shows practical embodiment of Routing Template page. Shows drop down options, some "Allergies" selections in command graphic tab, customizable. Contrast to FIG. 24.
Figure 24:
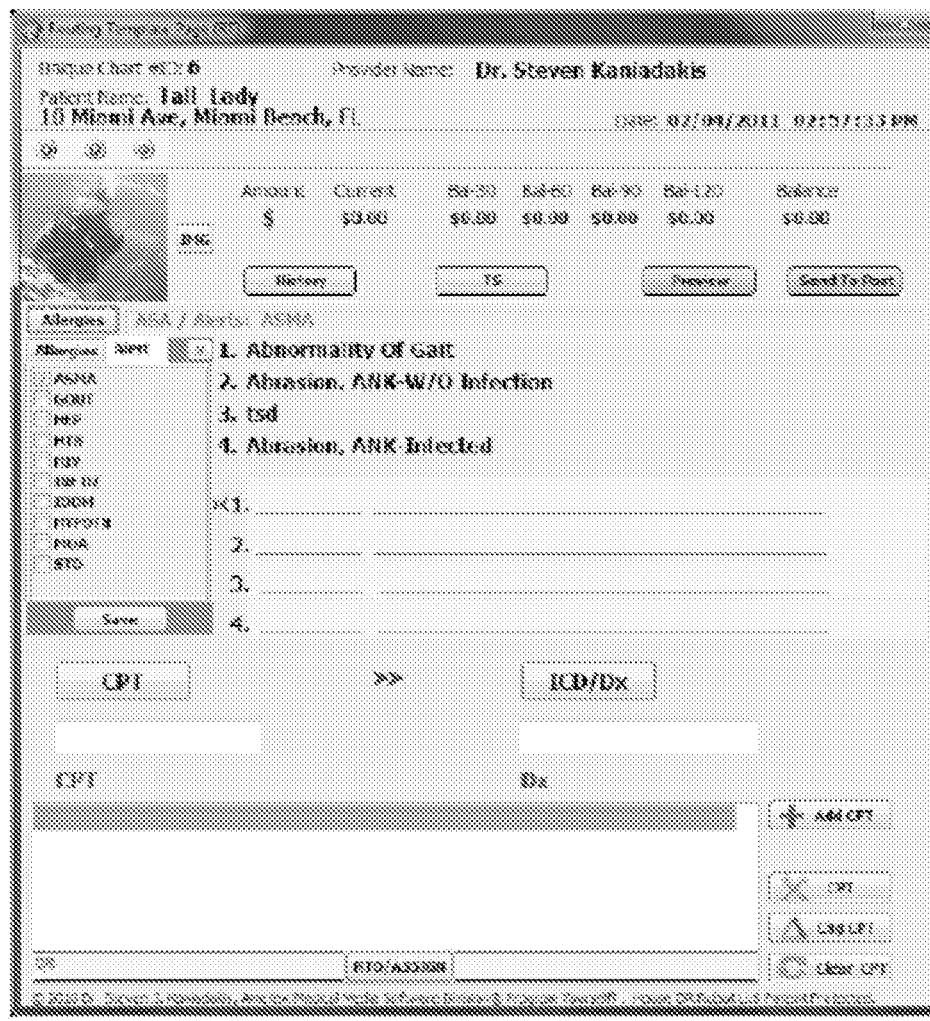
FIG. 24 shows the practical embodiment of Routing Template page. Shows drop down options, some "Alerts" selections in said tab, customizable. Contrast to FIG. 23.

FIGS. 44, 45, 46 shows a previous touch screen mode pops up (foreground) as in FIGS. 14, 22 as with this embodiment, component shows in FIG. 5. Contrast with FIG. 45. FIG. 44 touch key screen and interactive pad. FIGS. 45, 46 takes audio commands, the voice-to-text by saying house code letters "OV" will display on the screen. Clip board hook feature and pointer controller 12 moves via audio commands and speech to invoke field and keys of virtual keyboard. Advanced touch screen design for voice-to-text 12 shows in display to create progress notes. Extraction of code letters, code numbers and code descriptions easily corresponds to material for scanning billing and coding codes. Write-to-text on pointer controller acting like a mouse pad allows hand written conversion to text in display field. Voice, write and touch screen implementation allows security from detected key extraction spiders and spy software and implementations. Text-to-voice, by contrast, is for patients that cannot read progress notes and medical records on in this program (visually impaired). This is essentially a part of same reverse logic as described for implement used herein. Contrast with FIG. 45.

There are essentially two unique characteristics of touch screen and clip board technology that become incorporated in present art's detail. Refer to FIG. 5. First, is a clip board "hook" type design. A "clip board hook" is a term-of-art believed to be used by technology skilled people providing a computing device having a means for this embodiment's command logic that locates and targets the focus of an open field, to populate information or images into the open field or "clip board". Present invention realized that this system in combination works in a special compatible method along therewith the present invention's art namely; touch screen, voice-to-text 12 (Microsoft's® "Speech-to-text") or write-to-text applet part of present invention. FIGS. 45 and 46. Therefore, as a 12 pointer, cursor or arrow, becomes placed into or around a target essentially the proximal most field becomes the focus point, and information (command graphic or image) is inserted or populated into field proximal to the pointer, cursor or arrow of computer, device or apparatus. As with FIGS. 28 and 39, in showing just two instances. This operation is superior to general verbal commands like "next". Whereas, this embodiment combines the advantage of known type voice recognition systems and advantages thereof in using prior art "extraction" (billing code) transcription programs or progress notes when the client uses more elaborate means for voice recognition. This embodiment is superior to move the focus and populate fields, as this present invention's text on command graphics acting as interactive buttons become specific to the location where such data may become placed. This inventive design used as a part of present invention is more specifically described in the following way. Present invention is specific to locate the word or text on the command graphic 10, button or field, to focus population data or entry e.g. audio or 12 verbalized letters as, "OV" data populates a particular field such as the present invention's "CPT" field typically located proximal to the "CPT" command graphic on present invention's routing template page (screen) implementation. Wherein, data or entry will go to target field as focus point, just as analogous to data or image would go to (only) "clip board" field operation implementations.

Second, present invention including a command controller, cursor, or arrow pointer placement and providing this computer action. Here is the design part implementation that works in harmony or sorts with the above said "clip board hook" action. Wherein, present inventor realized that audio, human produced verbal or composite computerized audio (akin to a sound as in musical notes produced by key board strokes), effect voice interactive command controller FIGS. 28 and 39. For instance, the audio (electronic produced) or verbal command will go to focus and target proximal to selected text assigned to a certain interactive command graphic on invention's screen (page). Therefore, to verbally say commands and speech including words like, "Send To Post" (reference is made to command graphic's text), "Review Notes", "Space", "Backspace", "Save", "Import", "Caps Lock", or "Enter" or even generic action and word as, "close", invokes said action as noted or as annotated on command graphic's text in and around the proximity of said field's command graphic. The field or command graphic becomes invoked by (voice) 12 such audio interactive command controller. This action is, in effect, linked to afore said "clip board hook" function or apparatus. Even the inventor's created customized command graphic names like "CPT" or standard text, words or letters (like on keyboard) FIG. 39 become part of this operation. In short, voice using a clip board hook element populates field proximal to cursor or arrow placement. Clip board hook design is part of this invention working in this manner along therewith touch screen. FIG. 5 part 12, 21, 20, 28, 34, 33, 37, 44, 45, 46, showing other instances how clip board hook can work. Touch screen is an advantage to prevent detection of key board strokes FIG. 44 when such security desired. Clip board hook FIGS and audio command create an artificial intelligence. Prior art accounts for human intelligence in present art. Present art's machine method driven and this present art is including a non-transitory computing system readable intelligence as well as for the human intelligence which can become employed. Sounds or "notes" (instrumental notes) are created from key board strokes, whereas sound from audio detectable by human voice in order to create letters and symbols a person can recognize, human readable intelligence. Prior art and history will show that other inventions show the use of digital time wrist watches recorded input of phone numbers, and when end user would hold the watch to the phone, the repeated digitally produced sound of the phone number would electronically enable a call to be made over public phones and other past land line phones. This was typically a "touch tone" implementation. This was typically used by visually impaired persons. Touch screen and/or key board elements are implemented part of creating in-house letters readable by machine and human in translation. FIGS. 44 and 45. "OV" or code numbers 99213 or descriptive words "office visit" FIG. 45 thereby translated into billing codes. Present art enables users to create 4 their own in-house code letters or symbols, system, operation, method, becomes recognizable by human and machine intelligence both. FIGS. 35A and B. Prior art leaves out superior human intelligence as a cross checking language to be implemented in billing codes from progress notes, and other prior art leaves out CPT or ICD codes. Together components of CPT and or H.C.P.C. and of ICD diagnosis codes data point and data point sets, respectively, make a superior design, as with human and machine intelligence design. Present invention "extraction" design includes the involved design essentially with use of code letters equated with code numbers and code descriptions in a way to make a superior "Superbill" implantation for billing codes. Present art for said code letters, descriptions and code numbers to be extracted.

Milestones have been made in electronic world. However, superior design implements have been un-obvious heretofore. This invention's parts described thereof work to create a superior driving machine.

There are instances when more than one "I.C.D" is permitted to become used together with a single "C.P.T" and or H.C.P.C, and appropriately bundled or "unbundled", to send to other healthcare providers. A mechanism was heretofore unavailable. Coded language can become unique, by contrast, to each provider. Without corruption of the traditional code language utilized by a conventional terms-of art, such as "IOV" 4 for "Initial Office Visit" or "99204" code used to describe a level or evaluation in terms of certain healthcare practices. Whereby, use of said other code preserves intent of the original article. The need for a global language in today's global world makes this instrument novel in other domains or arenas.

Figure 12:
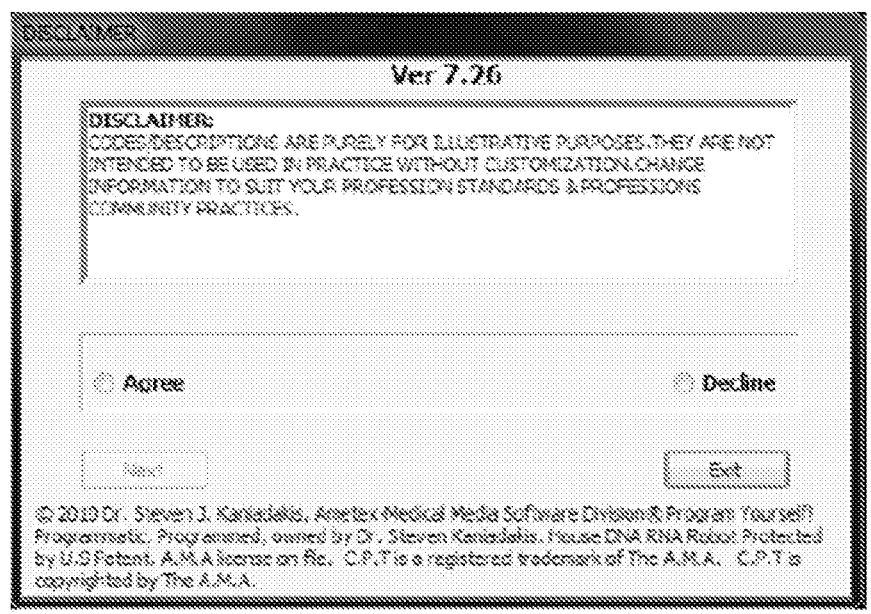
FIG. 12 displays log on/log in and disclaimer screen.
Figure 38:
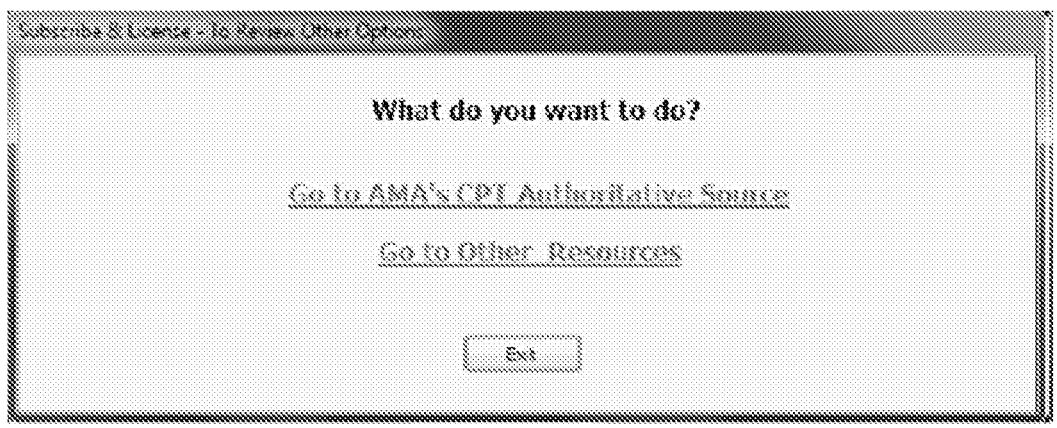
FIG. 38 shows a comparison and contrast to FIGS. 19/47. Specifically, at FIG. 12, the "decline" option implements this linkage to other companies and organizations.

Embodiment is including a computer method and related machine application program providing certain means for accessing computing intrinsic and extrinsic hardware and hereafter referred to as application or this "invention" or "superior" art that is intended to primarily serve as an extension of other medial related programs. Current computer technology terms-of-art describe this invention as a "third-party" application, a "plug-in" application, an "add-on" application among other jargon used for describing a general utility for the purpose of reference for part of this invention's functionality. These terms are obviated by the effect that they are applied in terms when there exists other known type (medical) computer or device methods related machine executions or programs hereafter referred to as "external" and extrinsic programs and including data and database types. Generally, technology describes an adjunct or a dominant program as "external" programs, which this application shall be compatible thereto. The inventor refers to external programs as the "main" program, computer or system. Accordingly, the inventor also refers to external programs and external database table structures 3 as extrinsic, pre-determined or known type existing programs. The inventor refers "device", as with computing device, in terms mentioned above. Since, in today's world as so called smart phones and tablets are not really computers per say, and this related equipment is typically referred to as computing devices. By some contrast, a "mnemonic device" is a term that can be expressed in conjunction. However, in application, and in this instance, the term device has not been mentioned in this manner. Therefore, embodiment's component parts is working with other certain pre-determined or known type data programs and other known type extrinsic program designs in combination therewith providing a computer or computing device and this invention. In fact, other technological terms-of-art, current day jargon or slang may be employed to describe this invention's connection, application, with reference a way this invention is used in practice. These terms are not intended to limit the scope of this superior art. FIG. 12 displays log on/log in and disclaimer screen. See FIG. 38, "decline" option implements linkages to other companies and organizations, e.g. American Medical Association (A.M.A), commercial vendors, suppliers (for code descriptions) billers and coders. FIG. 38 shows a comparison and contrast to FIGS. 19/47. Specifically, at FIG. 12, the "decline" option implements this linkage to other companies and organizations, e.g. American Medical Association (A.M.A), commercial vendors, suppliers (for code descriptions) billers and coders. Like for these connections, the element of the phone and e-mail in the embodiment have pre-configured database for contact settings, main appointment calendar, and including external or third party programs. However, user configuration settings can be allowed and customized within the first embodiment. FIGS. 12 and 38 are distinguished from and contrasted by the external linkages and external programs in reference to the actions invoked by the Sent To Post (STP) command graphics. This invention depends upon external programs in ways more fully discussed with the send to post action (STP) command graphics descriptions earlier and mentioned below. Therefore, this relationship between routing template, preview, and main appointment screens are working to handle, sort and filter, moving data as a data bridge for confluence, synchronizing and populating fields of data in respective data tables as well as an external program's and internal database table structures FIGS. 4 and 34.

This invention can act as a so-called, "standalone" application program to perform functions more specifically described herein. This invention is capable to act as a standalone and demonstrate maintenance of its own database 3. When this present invention is serving as a module this application will perform to receive and to eventually deliver populated FIGS. 15, 16, 17, 20 and 41 data back to the external programs database 3.

Accordingly, when this invention is serving a role as an extension, this invention works as a "module" application program. The flow chart function or logical sequence is essentially the same as when working as a standalone application program.

This invention when serving as an extension or "module" application program becomes a more than simply a superior performance enhancer to main programs currently in public domain. Wherein this invention as a method of application becomes compatible to external computers' or devices' programs to process information in a manner more specifically described herein.

This invention produces readable codes by providing a means for human intelligence creating code letters easy for a person to recognize and to recall the meaning, and with artificial intelligence creating code that in-turn becomes machine readable non-transitory storage. Therefore, this product is superior as this present invention recognizes that human intelligence is very significant in the practice of health care. Whereas, medical records can be readable by "extraction", human input is needed to be able to remain a significant component. Although extraction of code letters from the medical record to generate an engine to make billing codes therefrom, and this is a feature, a primary design feature is simply this process and method that creates an operating system with the implementing prior art of "Superbill" means to make a billing code. By use of code letters from code numbers, and code numbers from code letters read.

Accordingly, this invention is intended to populate an external program, with data, to receive data populated from external programs, and to act as a standalone instrument for information more specifically described herein. These in-house customized code letters are converted back into standardized code numbers acceptable by third party payers, before being sent.

This invention clearly operates by way of a method created mechanism with implementation of parts that move to function and control or drive other processes. This is more than mere manipulation of sequence programmer's code or of that code (e.g., C.P.T and or H.C.P.C. or I.C.D, etc.) used in professional practices and industry that produce similar processes in existing software related implements prior. This invention becomes an instrument.

Applicant's invention can be thought of as a computerized method providing a computer and computing device for assisting medical related data using standardized billing codes for the providers of goods and services. Each embodiment enabling communication of medical data as well as contacting people from the calendar related implementation including patients in their own domain, at work, at home using their own computer, database 3 and calendars 5.

The detailed embodiment has been described. Accordingly, the steps can be performed in any order. Generally the steps with main appointment page (MAP) screen are first and moving from inferior to superior. A patient account is selected from the database located at the lower one third of the MAP, an appointment is made at the middle one third of the MAP screen and after locating an available time on the upper one third of the calendar 5 an appointment is "saved" and the superior one third of the calendar is populated. Next, the movement starts at the upper one third of the MAP screen. The client's staffer invokes the name or patient account on the calendar. This generates the Routing Template (RT) page screen. If the user wants to contact a person or a patient's appointment, then the user invokes the command graphic control to make a call right from the appointment book calendar implementation. Or, the user can send the scheduled person a message by invoking the e-mail or user name in the contact section of the appointment book. Generally, staff needs to populate database related to goods and services performed. Sometimes patient accounts have been populated in the database step performed before populating the medical code database. Generally, the database of medical related data for goods and services is populated first and after provider names and clinical staff have entered their own account log in and information. This method is one that controls a computerized system and changes computer and computing system's database by way of user customization and configuration. Applicant's embodiment can be regarded as a computerized method for healthcare providers and their patients. However, the embodiment can be employed by other healthcare and other businesses and even in calendar implementation by friends, family and business associations. This brings the Routing Template page (screen). The routing template is generally populated from the superior one third to middle one third to distal one third. The embodiment's method description is generally the following steps. However, these steps can be performed by people skilled in the art in any order; the steps, construction and the method have been optimally created for superior feature and performance. Even by people with ordinary skill in the art using the embodiment as. Accordingly, detailed description outlined two general aspects of the invention, therefore, very broad and general outlined steps shall be presented in this following sequence;

Routing Template Part

1. Whereby, providing a computing system the client user is forming each data point and controllably coupling one data point medical code number description converted into each the client controlled customizable code letters which form another data point, and create the data point set.
2. The client user of the routing template is enabling sharing of the embodiment's customized database by more than one user client by sharing the database and the customized code created by at least one user client.
3. The client user's database is creating machine readable data.
4. Whereby, each data point in the client's database tables is controllably coupled with one data point medical code number description and converted into each the client controlled customizable code letters which form another data point, and the client creates the data point set.

Calendar Implementation Scheduler Part;
Method Also Includes the Following Embodiment and Implementation Component Part 5. Whereby, the phone call is controllably coupled right from the client's said calendar, appointment book, scheduling and event implementations by the invoked voice-over-internet-protocol implementation on the one screen using the object program code with the calendar.
6. Whereby, the scheduling event implementation is controllably coupled therewith the voice-over-internet-protocol types implementation and further includes the electronic mail message implementation on one screen in the combination thereof object target programs. The client is selecting each target program including each the user clients' preferences for calendar and telephonic phone call implementation.
7. Whereby, includes the plurality of the people the new method for with the phone call and sends and receives the messages right from the appointment book related screens, and connected to the known electronic device applications in the connection, web site pages screens, internet browser pages and screens and the electronic related devices.

Returning to the Routing Template Part Linking to the Scheduler Part (MAP Features)

8. Whereby, the interface includes one compact interface for the medical-related data point sets displayed which is in communication via the display screen part with another screen and produces this confluent synchronized flow of the data method with the appointment fields.
9. The Routing Template page (screen) is also a part having the features of the invention's programmatic feature. Whereby, extraction of the data and provides the pathway for the intrinsic extraction and the extrinsic extraction to the object program to at least one computer the standardized data point sets, to form the data set, further includes the patient account information, processed and non-processed medical related data.

10. Turning back to the linking features including the Routing Template page and the MAP screen scheduler and calendar related implementation wherein a command graphic invokes the actions of populating the display fields of the confluent synchronized flow and a dynamic appointment field implement on a screen. Whereby, the interface dynamic fields populate the dynamic calendar appointment book related displays, the display screen provides the confluent synchronized flow method with the appointment information.

11. The client user is using the linking features to the Routing Template and Main Appointment Page are calendar related appointment information.

12. Turning back to the Routing Template part wherein the user is selecting another third party known type object target program application when said other known type target object program is used in a combination with this inventor's object application program. Whereby, provides the embodiment of the object program is providing applications and the user invokes actions on the-interface using command graphics by keys on the keyboard and with pointer or pointer control devices.

13. The Routing Template part is listing of at least one of past four (4) diagnosis (abbreviated as, Dx) code numbers and descriptions. Whereby, the client directing attention to the fields for international classification of disease diagnosis (ICD fields) and the client user populates each the indicated fields on the clients interface and lists at least one standardized international classification of diseases (ICD) diagnosis at said four provided line numbered indicated fields.

14. The above mentioned Routing Template part wherein is using at least one command graphic and controlling each field listing of each the international classification of diseases diagnosis (ICD) adding with an add or removing with a remove command graphic each ICD.

15. Routing Template part the client user is using at least one diagnosis data point set as the client is assigned to each the abbreviated diagnosis designation number (an ascending Dx) and each adjacent the single the particular current procedural code terminology (CPT) or the particular healthcare common procedural coding system (HCPCS) code number description with the first abbreviated diagnosis designation number (Dx number, Dx 1, 2, 3, 4) in the housing being the prioritized position over each of the following adjacent three each displays displaying in the housing and the embodiment is designed in a moving line of action horizontally in the housing field and coupled with each of one or more of the abbreviated diagnosis designation number pop-up displaying (Dx) command graphics and each correlating thereto each the international classification of diseases (ICD) diagnosis and each list posted to each account of the particular patient unique chart identification, which each the users are selecting from their shared or not shared database accounts.

16. In the Routing Template part the inventor's is using special design and the inventor's previously registered U.S. Trademark Office including the mnemonic texting aspect and the Programmed texting, wherein the user is accessing at least one of the inventor's proprietary system and the inventor's embodiment including the Programmatic text field of Programmatic text logic as the user is anticipating and predicting the next letter, descriptor, character, number, word said data points and data point sets stored proximal to each respective data said command graphic and used in a combination with client user's interface, 17. Therefore, the Routing Template part and the Scheduler part is linked in a novel and superior method for matching with particularity certain known type standardized code number descriptions and the linking inventor's calendar related aspects as the user client is invoking a calendar command graphic, accessing and changing the client's selection of calendar object target program calendar related preferences from intrinsic appointment book related implementation of inventor's said appointment book related displays to selecting by the calendar command graphic at least one of an extrinsic known type calendar related implementation, further including accessing local, remote and external database computing in performing the client's appointment book related operations providing the computing and the components described in the detailed embodiment.

Therefore, the above steps are selected parts from the embodiment and these are more fully described in the detailed embodiment and the steps are not to limit the claim parts, only to give a broad outline thereof. Likewise, the numbers given above do not represent particular claim numbers, steps, parts or sequence.

Note that the print appointment card (PAC) has been linked to the embodiment, and linked subsequent linking claims, including the Routing Template page (RT screen) part. However, the Main Appointment Page (MAP screen) is showing the print patient appointment card, the embodiment is linking via Return To Office (RTO) command graphic controller therewith calendar and scheduling related aspects with medical screen for medical related reimbursement billing and coding aspects when used together.

A United States Patent should be granted to this submitted invention and recognize the inventor Dr. Steven J. Kaniadakis, the distinguished inventor of material that is original and in fact superior to prior art that U.S Patent records might reflect. Whereas, Dr. Steven J. Kaniadakis belief that he is in fact entitled to such award, and that his invention is indeed superior to prior art, and claims are all those of preserved by Dr. Steven J. Kaniadakis as related to descriptions and material by evidence submitted hereto.

What is claimed is:

1. A method of converting predetermined medical code numbers to and or from client specific information for medical-related data, including a software graphical user interface accessing one or more processors in using a computing device including a computer system, program codes stored in a memory of said computer system to cause said computer system to perform operations, the operations comprising:
   (a) generating at least one said interface and connecting to at least one database, and accessing said memory connected to the database from a hard drive storing data correlating the client specific data as a set of code letters, descriptors, symbolic code characters to data including the medical code numbers of dispensed goods and services rendered in the memory and data residing the database populating said graphical user interface,
   (b) accessing the database to store data as a sequential series of said code letters, descriptors or characters, as a data point and corresponding the data point to a particular data point including the known type medical code and either current procedural terminology or healthcare common medical procedural coding system code number series and description in the memory and the database,
   (c) inputting data adjacent to the data point series, forming a data point set including either said current procedural terminology code and description or said healthcare common procedural coding system to and or from corresponding said code letters, descriptors or characters,
(d) storing said data point set created by the client in said memory,
(e) generating at least one display field, and reading the data point as the data point set,
(f) directing a pointer or a command controller using said fields and enabling editing for writing operations including the data point stored in at least one other database table location, further fashioning and creating any customized input of the clients specific data,
(g) outputting for an operator readable edited data as the data point and the data point set populating the system's memory and the hard drive of a non-transitory computer readable storage medium and a machine reading data point set determined as said code letters, descriptors or character series,
(h) displaying a programmatic mnemonic texting aspect including said fields enabling the programmed texting of the next letter, descriptor, character, number, word including anticipating the medical code sequence series and description stored in the memory or stored in said subsequent database table location, and extracting the client's data in the database further including any of the data point and the data point set,
(i) mapping and further repopulating current procedural terminology or healthcare common procedural coding system providing a transitional in-house medical code description,
(j) repeating steps (a) through (i) producing and reproducing the same exacting and the client specific outcome parsing results including the data point being presented in an object target program.

2. The method of claim 1, wherein said interface accessing said computing system's artificial intelligence and each said data point set created by the client, further including a second client using the same machine and conveying the same database of the client and the second client and enabling editing for the second client operator and still further including customizing the first clients data.

3. The method of claim 1, wherein said interface accessing said computing system's artificial intelligence and said data point set is created by the client said storage by said second client and, further including reciprocating each of the client's dataset.

4. The method of claim 1, wherein said data point conversions created by said client's computing system's artificial intelligence said data point and data point set is producing the machine computer readable said storage thereof said code letters which are converted back to said medical code numbers in each selected said data point set and the client and the second client thus restoring the medical code numbers forming the data points using a system restore command graphic located on the interface.

5. The method of claim 1, wherein including to create a patient appointment card, showing pertinent appointment information using at least one calendar and a main appointment display screen and field, further including saving, storing and sending the appointment card information electronically, and further including said appointment card is reproducible using the computing device,
(a) inputting data in at least one field in said interface data related to appointment related information populating and synchronizing at least one said display screen,
(b) producing a tangible reproduction of said appointment related information via accessing a printer, and sending said appointment related data to an electronic file in said computing devices and storing said appointment related data, and sending the same to said printer device configured for printing the same as a hardcopy by invoking the interface framework and the devices printing command graphics, and further including the client customizing the reproduction with the clients identifying information including company name, logo and contact information.

6. The method of claim 5, wherein a command graphic invokes populating fields of the confluent synchronized flow and a dynamic appointment field implement on a screen, electronically communicating the fields and the interface with the appointment related information from a clinical treating type healthcare provider electronically to another client as an administrative business staff, further including a time schedule table member, tabulating each relevant patient, and creating a dynamic calendar and appointment fields,
whereby, said interface dynamic fields populate the dynamic calendar appointment book related displays, the display screen provides the confluent synchronized flow method with said appointment information.

7. The method of claim 5, further including that the appointment information posted may be sent electronically to the relevant patient, providing said computer, the computing devices or phone, and a patients hardware respectively, sending electronically and reproducing said appointment providing a tangible hardcopy a data record, and the date and time period to the patient and the client, respectively.

8. The method of claim 1, wherein converting medical code related descriptions in a medical record back to said medical code numbers and in combination with a known object target program using an extraction implementation, providing a pathway and further including the client providing and accessing at least one of a known type of an extrinsic database, a server side database tables, a remote database, and synchronizing at least one clients database locally and intrinsic to the memory and to the hard drive on the client's side of the computer therewith the extrinsic database tables forming a dataset, further including each international classification of disease code representative of a standardized code number description matching a customized international classification disease code number description by the client using the graphical user interface,
(a) posting data to and from the extrinsic data tables said medical-related records, progress notes, operation reports, billing code data,
(b) processing and corresponding each said in house medical code description therewith each the data between said known extraction object target program to said memory and to each the database tables, the client parsing the data, and filtering the data from said extraction for populating the tables in the clients said local hard drive database,
(c) importing data for populating at least one said interface of object program and each said computer and the memory with raw data non-processed data points, including current procedural terminology, healthcare common procedural coding system and international classification of diseases, a set of patient accounts,
(d) exporting data from said computer processed data including said raw data as said non-processed data points, including each the interface database storage and memory.

9. The method of claim 1, wherein a use of another third party known type object target program application when said other known type target object program is used in a combination with this inventor's object application program and further including, (a) accessing by configuration a known type voice-to-text, by a command wherein the operator commands speech for a means for controllably directing and invoking said pointer and invoking said command causing each action on said interface, further including the client making medical dictations including progress notes, (b) accessing by configuration another known type object target program enabling write-to text via invoking a pointer controller pad on said computer and the pointer controller pad providing an external pad or touch screen sensitive to inputting hand writing to the display, (c) accessing by configuration audio commands, said audio input populating said fields, (d) accessing by configuration the computing devices voice recognition and training audio commands and perfecting the clients text input to the display fields from the voice-to-text implementation, (e) accessing by configuration a clipboard hook so the clients voice commanding and prompting are invoking the clients particular text commands and prompts, respectively on each said command graphic text for said interface causing the clipboard hook moving action of said pointer to each the field and invoking each action without touching and clicking on said interface, (f) accessing by the configuration the known type voice-to-text further including a command graphic enabling an interactive touch sensitive monitor invoking said actions on a virtual keyboard on the computer eliminating key stroke audio sound detection using the computing device including a monitor providing touch screen.

10. The method of claim 1, wherein the interface shape has at least four fields provided in superior to inferior order each positioned approximately subjacent and located at proximal aspects to one and another and the fields of the interface are positioned further including fields which are constructed for a listing of at least one of past four (4) diagnosis code numbers and descriptions and, (a) inputting each said diagnosis code number with an adjacent and corresponding said diagnosis code description, as said diagnosis data point set, (b) outputting each said field with one said diagnosis data point set thereto and said listing as an ascending list of designation positions listing each field as a number and populating each the designated field indicated in the list, (c) invoking a save command graphic, and saving to send for posting said diagnosis data point set, at least one of a back-up database location as being processed type data, accessing said client's memory and said clients database, storing said diagnosis data point set, (d) accessing of said diagnosis data point sets as non-processed raw data or as said processed databases in said clients memory and populating at least one said indicated field number, (e) placing into said memory said diagnosis data point set on a particular said field line number an international classification of disease diagnosis data point, (f) repeating steps or parts (a) through (e) for adding and removing the clients said known international classification of diseases diagnosis medical code number description sets, whereby, said fields for international classification of disease diagnosis said indicated fields populates said clients interface and lists at least one standardized international classification of diseases diagnosis at said four provided line numbered indicated fields.

11. The method of claim 10, wherein at least one command graphic controlling each field of said listing of each the international classification of diseases diagnosis further including, (a) adding with an add command graphic said international classification of diseases diagnosis data point set to any respective said indicated field, the add command graphic and said listing and each the field thereof located at a subjacent aspect to a permanent diagnosis field, and displaying on said interface previously from said memory, (b) removing with a remove command graphic said international classification of diseases diagnosis data point set in said field or by replacing the permanent diagnosis field entry by invoking said add and a save command graphic and at a subsequent step substituting with another international classification of diseases diagnosis data point.

12. The method of claim 10, wherein and further including designating each said diagnosis data point set as yet another designation point, (a) selecting from a drop down selection pop up command graphic field a designation, abbreviating each as diagnosis one or two or three or four, (b) prioritizing each the drop down pop up command graphic by an ascending position each selected said abbreviated diagnosis designation number in connection to an international classification of disease diagnosis code number description, (c) enabling at least one of the abbreviated diagnosis designation in a housing field for further correlating with a single said known medical code including said known type current procedural terminology or said healthcare common code procedural coding system code number description and each can be further including said code letter series forming said data point set and, (d) populating and programmatically assembling said medical-related data furthermore in the housing field at distal third of said interface said data point set entered adjacent as each the abbreviated diagnosis designation pop up command graphic field box invoked, (e) invoking each said command graphic on said interface producing and storing the non-transitory computer readable medium storage with the readable non-processed raw data as said data point set stored and assembling the medical related data in the housing field, (f) repeating parts, (a) through (e) and to list at least one said abbreviated diagnosis, further forming and defining a data point set for processing as the processed data point set, and further including the connection to a particular patient unique chart identification account in the housing field table, and said housing field holding an unlimited list of sets for processing data and displaying as a vertical assembly line listing the data for each said patient account and an encounter, (g) saving or sending to post via a command graphic invoking said save command graphic or the send to post command graphic respectively for storing, and at this step the data is stored as the processed data point sets to said database tables and said backup data storage history in said memory of each the encounter, further including data point sets, thereof adding a patient demographic data accounts, including third party payers, providers, the client log in access, permissions, parsing the non-processed type data raw data including the data point sets and said client specific patient account into the processed type data, whereby, at least one diagnosis data point set is assigned to each said abbreviated diagnosis designation number and each adjacent the single said particular current procedural code terminology or particular healthcare common procedural coding system code number description displaying in the housing.

13. The method of claim 1, the mnemonic texting aspect and the programmed texting, wherein at least one of said programmatic text field of said programmatic text logic is anticipating and predicting the next letter, descriptor, character, number, word part of said data points and data point sets stored proximal to each respective data said command graphic and used in a combination with said client interface,
   (a) accessing said programmatic text field for performing said extraction using said programmatic text search type feature for the data and the data point set of said non-processed raw data for populating said client interface and using a template design from the client customized data tables,
   (b) accessing said extraction, performing said programmatic search type feature of said data and the data point sets, further including the patient account, said status discussion and given each the patient demographics in the clients memory,
   (c) invoking at least one command graphic, causing selected medical related data to populate said housing display for each current procedural code terminology or each healthcare common procedural coding system and at least one said international classification of diseases diagnosis,
   (d) invoking said add command graphic text which is invoking resultant selection either from said programmatic field, and shifting each the selected medical related data to populate and to add each to distal housing in the vertical and horizontal method.

14. The method of claim 1 for matching with particularity certain said known type code number description according to claim 1 wherein,
   (a) invoking a calendar command graphic,
   (b) changing the client's selection of calendar object target program calendar related preferences from intrinsic appointment book related implementation of inventor's said appointment book related displays to selecting by said calendar command graphic at least one of an extrinsic known type calendar related implementation, further including accessing local, remote and external database computing in performing the said appointment book related operations.

15. A method for a client using a plurality of known voice-over-internet-protocol in contacting and communicating with a plurality of people said voice-over-internet-protocol implementation when utilized in a combination a plurality of known type object target programs, the client using a new program computer code scripting, performing, executing, by accessing one or more processors in using a computing device, a computer system, program codes accessing the new program stored in a memory and a hard drive of a non-transitory computer readable storage medium of said computer system causing the computer system to perform operations, the operations comprising:
   (a) accessing said memory and the screen display on said computer displaying the object target program interface using said computing devices,
   (b) changing the memory and the computer database of the client via the new program a configuration accessing the database of the clients computing device enabling the known voice-over-internet-protocol on the object target program including appointment book related screens, calendar, schedulers of event chronology implementations, the new program further including and enabling said voice-over-internet-protocol including as an extension, add-on and plug-in for the database on the computer,
   (c) converting via the new program a listing of phone numbers into interactive electronic commands or a command graphic therefrom the scripting and displaying on the object target program interface,
   (d) providing by the configuration via the computing device of the phone numbers on the screen in effect executing the voice-over-internet-protocol in said object target program code and related the computer code on the client's side in the database program code, further causing the listing of phone numbers as interactive phone numbers wherein creating the new use of the client's screens including said voice-over-internet-protocol therewith said calendar related implementation,
   (e) invoking the command graphic for making each telephonic call by the client in the configuration,
   (f) repeating (a) through (e) for making changeable to another known type voice-over-internet-protocol using the combination with different types of the object target program making each telephonic call on the appointment book calendar via changing the database and using the computer or the computing device.

16. The method of claim 15, wherein said voice-over-internet-protocol further including a means for providing a known type of computerized system for connecting a telephonic phone call and including controllably coupling and further including known instant messaging add-on, plug-in, and extension contacting and communicating with said plurality of people using the instant messaging as an object target program code when the instant messaging said object target program implementation becomes used in a new combination with the means of sending and receiving messages from the plurality of said object target programs on said appointment book related screens.

17. The method of claim 15, wherein means for controllably coupling the plurality of each said voice-over-internet-protocol to a plurality of each electronic mail application as an object target program in contacting and communicating with a plurality of people used in a combination with the interface for sending and for receiving messages, with each the plurality of object target programs interface including the plurality of said appointment book related screens further comprising,
   (a) accessing the memory and changing said database enabling the electronic mail on said object target program on said computer,
   (b) converting electronic mail addresses into interactive electronic command graphics which are displaying in said object target program including said appointment related book screens,
   (c) clicking or touching and invoking said interactive electronic mail address on said display in said object program on said appointment book related screens so said interactive electronic mail address is sending, receiving, said electronic messages,
   (d) changing said electronic mail implementation to another said known type electronic messaging implementation, client making changes to said client database using preference command graphics with the computing devices controls and settings, enabling use of the each other type electronic mail, without effectuating the object target programs codes the voice-over-internetprotocol nor to the database configuration of the selected for the appointment book related screens, calendar, scheduler, event planner implementation, (e) repeating parts or steps (a) through (d) for un-installing and installing the known type electronic mail client applications.

18. The method of claim 15, wherein the method is including other known type object target programs other than the health care implementations including a plurality of each object programs and in said combination with the appointment book related screens for forming a method to contact people in a virtually world wide web site as a domain further networking and forming a system.

* * * * *